(12) United States Patent
Meehan et al.

(10) Patent No.: US 10,503,756 B2
(45) Date of Patent: Dec. 10, 2019

(54) CLUSTER PROCESSING AND RANKING METHODS INCLUDING METHODS APPLICABLE TO CLUSTERS DEVELOPED THROUGH DENSITY BASED MERGING

(71) Applicant: THE BOARD OF TRUSTEES OF THE LELAND STANFORD JUNIOR UNIVERSITY, Palo Alto, CA (US)

(72) Inventors: Stephen W. Meehan, West Lafayette, IN (US); Wayne A. Moore, San Francisco, CA (US); Guenther Walther, Mountain View, CA (US); Darya Orlova, Menlo Park, CA (US); Connor G. W. Meehan, Pasadena, CA (US); David R. Parks, San Francisco, CA (US); Leonore A. Herzenberg, San Francisco, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 1045 days.

(21) Appl. No.: 14/691,044

(22) Filed: Apr. 20, 2015

(65) Prior Publication Data
US 2015/0293992 A1 Oct. 15, 2015

Related U.S. Application Data

(63) Continuation-in-part of application No. 13/342,722, filed on Jan. 3, 2012.

(Continued)

(51) Int. Cl.
*G06F 16/28* (2019.01)
*G06F 16/22* (2019.01)
(Continued)

(52) U.S. Cl.
CPC ........ *G06F 16/285* (2019.01); *G06F 16/2237* (2019.01); *G06F 16/2246* (2019.01);
(Continued)

(58) Field of Classification Search
CPC ....... G01N 15/1459; G01N 2015/1402; G01N 2015/1477; G06K 9/627; G06F 16/285; G06F 16/2246; G06F 17/18
(Continued)

(56) References Cited

U.S. PATENT DOCUMENTS 8,473,215 B2 6/2013 Walther et al.
2003/0219150 A1* 11/2003 Niles ................. G06K 9/00
382/128

(Continued)

OTHER PUBLICATIONS

Bagwell, C. "A journey through flow cytometric immunofluorescence analyses—Finding accurate and robust algorithms that estimate positive fraction distributions", Clin. Immunol. Newsletter. 1996; pp. 33-37.

(Continued)

*Primary Examiner* — Eman A Alkafawi
(74) *Attorney, Agent, or Firm* — McCarter & English, LLP; Beverly W. Lubit

(57) ABSTRACT

The described invention provides a method and/or system for analyzing data using population clustering through density based merging, and a method for guiding clustering strategy through entropy-based ranking score.

24 Claims, 40 Drawing Sheets

Related U.S. Application Data

(60) Provisional application No. 61/981,422, filed on Apr. 18, 2014, provisional application No. 61/429,355, filed on Jan. 3, 2011.

(51) Int. Cl.
| | |
|---|---|
| *G06F 17/18* | (2006.01) |
| *G06K 9/00* | (2006.01) |
| *G06K 9/62* | (2006.01) |
| *G01N 15/14* | (2006.01) |

(52) U.S. Cl.
CPC ......... *G06F 17/18* (2013.01); *G06K 9/00147* (2013.01); *G06K 9/627* (2013.01); *G01N 15/1459* (2013.01); *G01N 2015/1402* (2013.01); *G01N 2015/1477* (2013.01); *G01N 2015/1488* (2013.01)

(58) Field of Classification Search
USPC .............................. 702/155, 19, 21; 250/251
See application file for complete search history.

(56) References Cited

U.S. PATENT DOCUMENTS

| | | | |
|---|---|---|---|
| 2005/0246105 A1 | 11/2005 | Faber et al. | |
| 2006/0020597 A1 | 1/2006 | Keating et al. | |
| 2006/0183141 A1* | 8/2006 | Chang | C12Q 1/6886 435/6.14 |
| 2007/0118297 A1* | 5/2007 | Thayer | G06K 9/00147 702/21 |
| 2008/0243398 A1* | 10/2008 | Rabinowitz | G06F 19/18 702/20 |
| 2009/0204637 A1 | 8/2009 | Li et al. | |
| 2010/0112628 A1 | 5/2010 | Gernez et al. | |
| 2012/0273664 A1* | 11/2012 | Grier | B01L 3/502761 250/251 |
| 2013/0226469 A1 | 8/2013 | Robinson et al. | |

OTHER PUBLICATIONS

Bakker, T. C. et al., "Cluster analysis of flow cytometric list mode data on a personal computer", Cytometry. 1993; vol. 14(6), pp. 649-659.

Boedigheimer, M. J. et al. "Mixture modeling approach to flow cytometry data", Cytometry. 2008; vol. 73(5), pp. 421-429.

Demers, S. et al. "Analyzing multivariate flow cytometric data in aquatic sciences", Cytometry. 1992; vol. 13(3), pp. 291-298.

Finch, P.D. et al. "Substantive difference and the analysis of histograms from very large samples", J Histochem Cytochem. 1979; vol. 27(3), pp. 800.

Gentleman, Ret al. "Bioconductor: open software development for computational biology and bioinformatics", Genome Biology. 2004; vol. 5(10), pp. 1-16.

Godtliebsen, F. et al., "Significance in scale space for bivariate density estimation", 1999, pp. 1-18.

Guibas et al., the earth mover's distance, multi-dimensional scaling, and colour based image retrieval, 1997, IEEE, p. 1-8.

Hitchcock, F. L "The distribution of a product from several sources to numerous localities", J Math. Phys. 1941; vol. 20, 224-230.

Lampariello, F. "Evaluation of the number of positive cells from flow cytometric immunoassays by mathematical modeling of cellular autofluorescence", Cytometry. 1994; vol. 15(4), pp. 294-301.

Lampariello, F. et al., "Complete mathematical modeling method for the analysis of immunofluorescence distributions composed of negative and weakly positive cells", Cytometry.1998; vol. 32, pp. 241-254.

Levina, E. et al., "The earth mover's distance is the mallows distance:some insights from statistics", 2001, IEEE, all pages.

Lo, K. et al."Automated gating of flow cytometry data via robust model-based clustering", Cytometry. 2008; vol. 73(4), pp. 321-332.

Murphy, R F. et al., "Automated identification of subpopulations in flow cytometric list mode data using cluster analysis", Cytometry. 1985; vol. 6(4), pp. 302-309.

Overton, W.R. "Modified histogram subtraction technique for analysis of flow cytometry data", Cytometry. 1988; vol. 9(6), pp. 619-626.

Roederer, M. et al. "Probability binning comparison: a metric for quantitating univariate distribution differences", Cytometry. 2001; vol. 45(1), pp. 37-46.

Rogers, W.T. et al., "FlowFP: A Bioconductor Package for Fingerprinting Flow Cytometric Data", Adv Bioinformatics,2009; vol. 2009, pp. 1-11.

Rubner, Y. et al., "A metric for distributions with applications to image databases", Proceedings of the 1998 IEEE International Conference on Computer vision. 1998, pp. 59-66.

Rubner, Y. et al., "The earth mover's distance, multi-dimensional scaling and color-based image retrieval", DARPA IUW, 1997, all pages.

Walther, G. et al. "Automatic clustering of flow cytometry data with density-based merging", Adv Bioinformatics. 2009, pp. 1-7.

Young, I.T. "Proof without prejudice: use of the Kolmogorov-Smirnov test for the analysis of histograms from flow systems and other sources", J Histochem Cytochem. 1977; vol. 25(7), pp. 935-941.

\* cited by examiner

| | ForSc | OrthS c | <Fluo r> | <Phy Ery> | <Cy5 PE> | <TexR ed> | <A1P hCy> | <Cy7 APC> | <Cy7P E> | <Cas Blu> | <Cy5 5PE> | <Cy5 5AP> |
|---|---|---|---|---|---|---|---|---|---|---|---|---|
| 1 | 352 | 6.65 | 0.26 | 16.6 | 0.56 | 0.79 | 8.71 | 0.82 | 17.6 | 1.45 | 7.92 | 0.1 |
| 2 | 228 | 7.06 | 0.31 | 14.7 | 0.1 | 6.57 | 6.88 | 0.97 | 24.6 | 1.38 | 27.8 | 1.32 |
| 3 | 238 | 6.76 | 0.56 | 21.2 | 1.05 | 0.33 | 16.7 | 0.1 | 0.1 | 1.51 | 9.08 | 0.22 |
| 4 | 240 | 9.86 | 0.1 | 6.32 | 0.1 | 26.3 | 5.28 | 0.1 | 849 | 1.67 | 19.6 | 0.1 |
| 5 | 234 | 6.13 | 0.39 | 14.1 | 1.07 | 7.85 | 8.57 | 0.62 | 0.1 | 2.01 | 20.2 | 1.86 |
| 6 | 395 | 6.62 | 0.13 | 14.2 | 0.63 | 7.46 | 0.1 | 1.99 | 2.43 | 1.85 | 19.5 | 0.1 |
| 7 | 237 | 6.95 | 0.36 | 10.1 | 0.63 | 0.12 | 3.07 | 1.73 | 31.7 | 0.42 | 12.7 | 0.1 |
| 8 | 337 | 6.21 | 0.2 | 12.9 | 0.27 | 7.09 | 2.28 | 0.1 | 80.3 | 1.45 | 16.7 | 0.4 |
| 9 | 254 | 11 | 0.22 | 17.2 | 1.41 | 12.1 | 7.11 | 1.58 | 24.1 | 1.22 | 12.9 | 0.17 |
| 10 | 326 | 4.88 | 0.58 | 23.8 | 0.44 | 1.96 | 88.7 | 2.49 | 5.5 | 0.32 | 10.5 | 30.5 |
| 11 | 236 | 12.8 | 0.51 | 18.6 | 0.84 | 15.1 | 1.12 | 0.1 | 214 | 1.38 | 28.7 | 2.45 |
| 12 | 311 | 8.93 | 0.63 | 4.62 | 0.37 | 1.52 | 8.49 | 0.62 | 4.85 | 0.39 | 11.3 | 1 |
| 13 | 250 | 10.8 | 0.33 | 19.9 | 0.17 | 4.18 | 4.24 | 1.62 | 75.5 | 1.97 | 15 | 0.1 |
| 14 | 336 | 9.79 | 0.6 | 13.5 | 2.46 | 10.9 | 105 | 1.37 | 0.1 | 1.75 | 21.4 | 5.45 |
| 15 | 280 | 6.6 | 0.8 | 18.6 | 0.37 | 1.86 | 9.03 | 0.66 | 19.4 | 1.89 | 8.14 | 0.79 |
| 16 | 286 | 7.58 | 0.41 | 13.8 | 0.1 | 0.47 | 6.09 | 1.52 | 14.2 | 1.81 | 18 | 0.1 |
| 17 | 262 | 5.75 | 0.44 | 12.8 | 0.1 | 0.56 | 6.74 | 2.23 | 2.93 | 1.85 | 13.7 | 0.41 |
| ... | | | | | | | | | | | | |
| 9510 | 247 | 8.09 | 0.41 | 18.2 | 0.53 | 0.1 | 22.7 | 0.39 | 7.8 | 0.79 | 16.5 | 0.68 |
| 9511 | 432 | 9.37 | 0.71 | 17.4 | 0.45 | 9.14 | 5.18 | 1.46 | 51.5 | 1.08 | 13.9 | 0.89 |
| 9512 | 448 | 10.3 | 0.52 | 18.5 | 0.1 | 9.09 | 4.78 | 1.07 | 7.92 | 1.45 | 32.5 | 0.5 |
| 9513 | 214 | 7.74 | 0.34 | 15.9 | 1.16 | 6.8 | 1.28 | 1.19 | 1.68 | 1.75 | 14.6 | 0.9 |
| 9514 | 314 | 10.1 | 0.51 | 12.4 | 0.17 | 4.02 | 0.46 | 2.47 | 85.9 | 1.31 | 25.4 | 0.51 |
| 9515 | 234 | 7.53 | 0.44 | 9.98 | 0.1 | 5.01 | 0.43 | 0.3 | 53.5 | 0.99 | 19.9 | 0.1 |
| 9516 | 213 | 7.21 | 0.48 | 7.41 | 0.21 | 3.69 | 0.12 | 0.42 | 3.38 | 0.66 | 8.55 | 0.43 |
| 9517 | 216 | 8.24 | 0.35 | 8.03 | 0.66 | 5.42 | 7.53 | 0.1 | 83.5 | 1.52 | 20.1 | 2.17 |
| 9518 | 307 | 6.96 | 0.36 | 17.9 | 0.12 | 7.24 | 4.93 | 0.1 | 0.31 | 0.66 | 13.5 | 0.51 |
| 9519 | 214 | 8.22 | 0.41 | 19.4 | 0.12 | 1.6 | 6.73 | 0.1 | 57.9 | 1.93 | 16.4 | 1.95 |
| 9520 | 173 | 5.27 | 0.31 | 18 | 0.1 | 2.5 | 9.18 | 0.91 | 0.69 | 1.61 | 7.55 | 1.19 |
| 9521 | 392 | 9.5 | 0.31 | 18.1 | 0.67 | 2.23 | 7.53 | 1.88 | 0.1 | 2.01 | 12.6 | 0.1 |
| 9522 | 429 | 5.43 | 0.65 | 17.1 | 1.86 | 7.11 | 10.9 | 1.85 | 3.01 | 1.26 | 8.11 | 0.1 |
| 9523 | 308 | 8.85 | 0.64 | 29.3 | 1.96 | 4 | 6.68 | 0.8 | 3.54 | 1.96 | 23.1 | 0.91 |
| 9524 | 296 | 8.59 | 0.56 | 20.4 | 0.44 | 6.11 | 8.09 | 0.67 | 3.79 | 1.54 | 28.6 | 1.19 |
| 9525 | 354 | 9.25 | 0.65 | 16.7 | 0.1 | 12.6 | 0.1 | 0.65 | 102 | 1.88 | 34.4 | 0.1 |
| 9526 | 260 | 7.78 | 0.4 | 21.4 | 0.94 | 2.21 | 7.8 | 0.33 | 0.1 | 1.5 | 16 | 1.35 |
| 9527 | 300 | 7.71 | 0.57 | 36.8 | 1.18 | 1.25 | 121 | 2.38 | 3.84 | 0.79 | 7.57 | 24.9 |
| 9528 | 172 | 7.14 | 0.46 | 11.4 | 0.44 | 0.75 | 8.47 | 0.84 | 5.15 | 1.26 | 15.8 | 0.1 |
| 9529 | 265 | 5.66 | 0.18 | 5.17 | 0.1 | 233 | 1.68 | 0.1 | 0.1 | 0.45 | 9.03 | 4.75 |
| 9530 | 378 | 9.73 | 0.67 | 16 | 0.1 | 12.6 | 2.13 | 0.1 | 278 | 1.6 | 32.5 | 0.46 |
| 9531 | 222 | 7.03 | 0.36 | 16.8 | 0.1 | 17.9 | 6.28 | 0.1 | 6.93 | 1.62 | 23.1 | 1.42 |
| 9532 | 419 | 9.93 | 0.64 | 18.9 | 0.31 | 7.81 | 3.37 | 0.37 | 111 | 1.13 | 23.9 | 0.1 |
| 9533 | 353 | 7 | 0.58 | 13.4 | 0.25 | 20.2 | 0.1 | 0.84 | 0.96 | 1.63 | 15.5 | 0.1 |

*FIG. 1*

5% trim

9% trim

Widening outliers alpha=.09 %

Matching a given plot's clusters

- Essential to automating gating is determining which clusters are the same as those seen with a previous sample for each plot in a sequence of plots

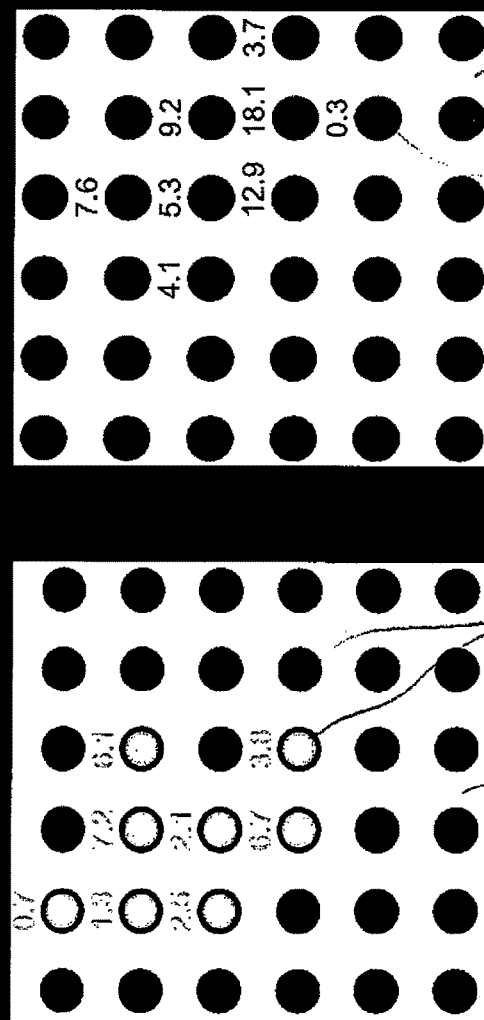

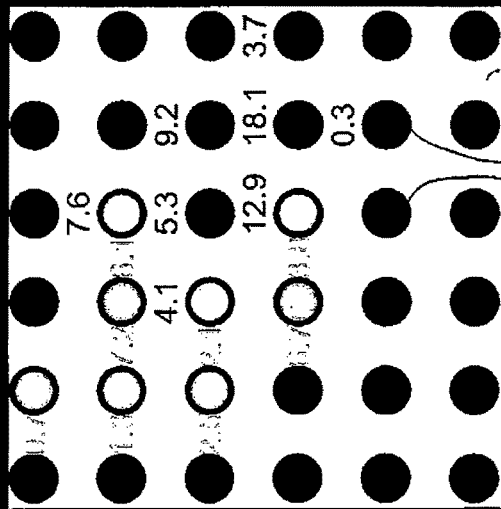

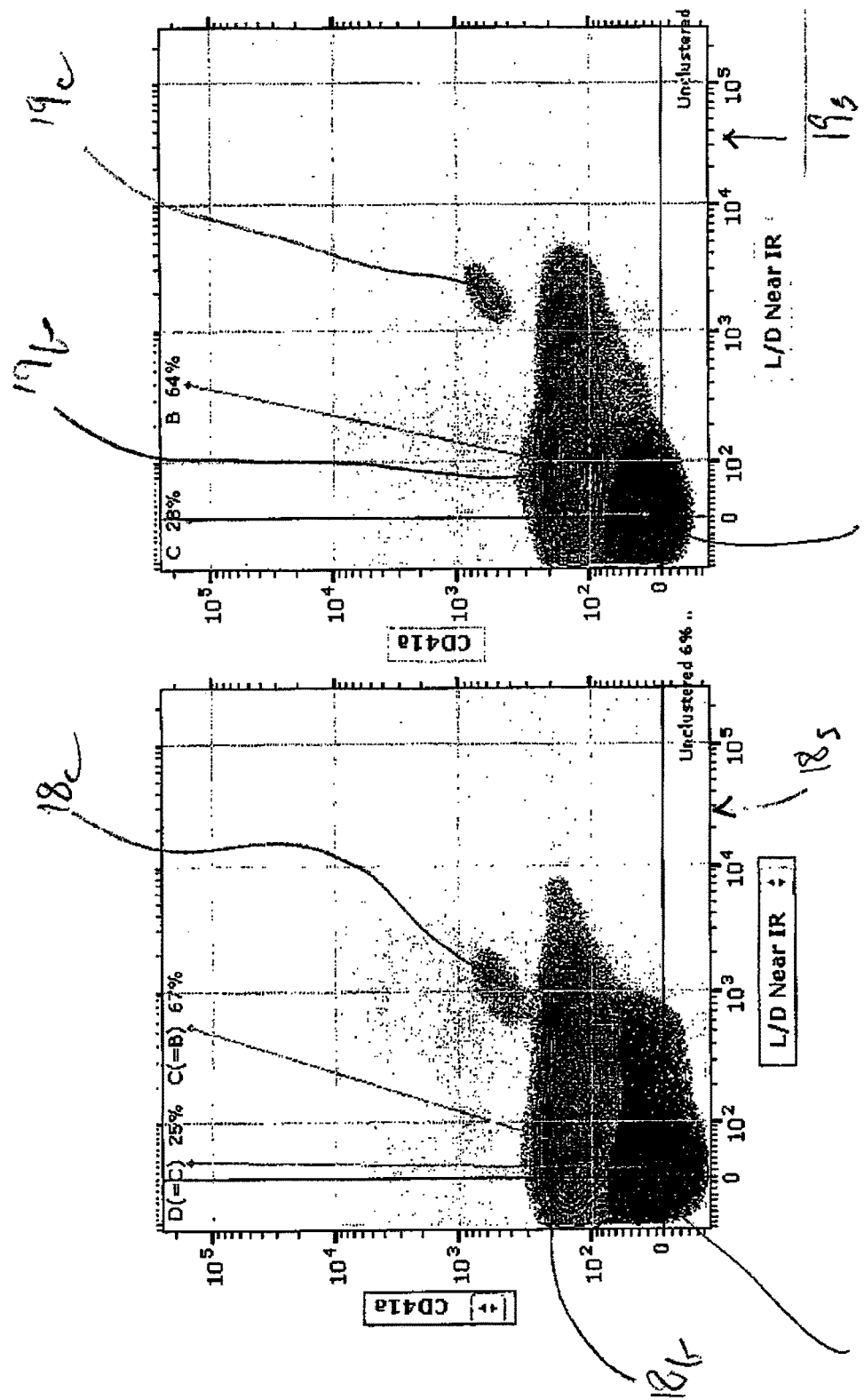

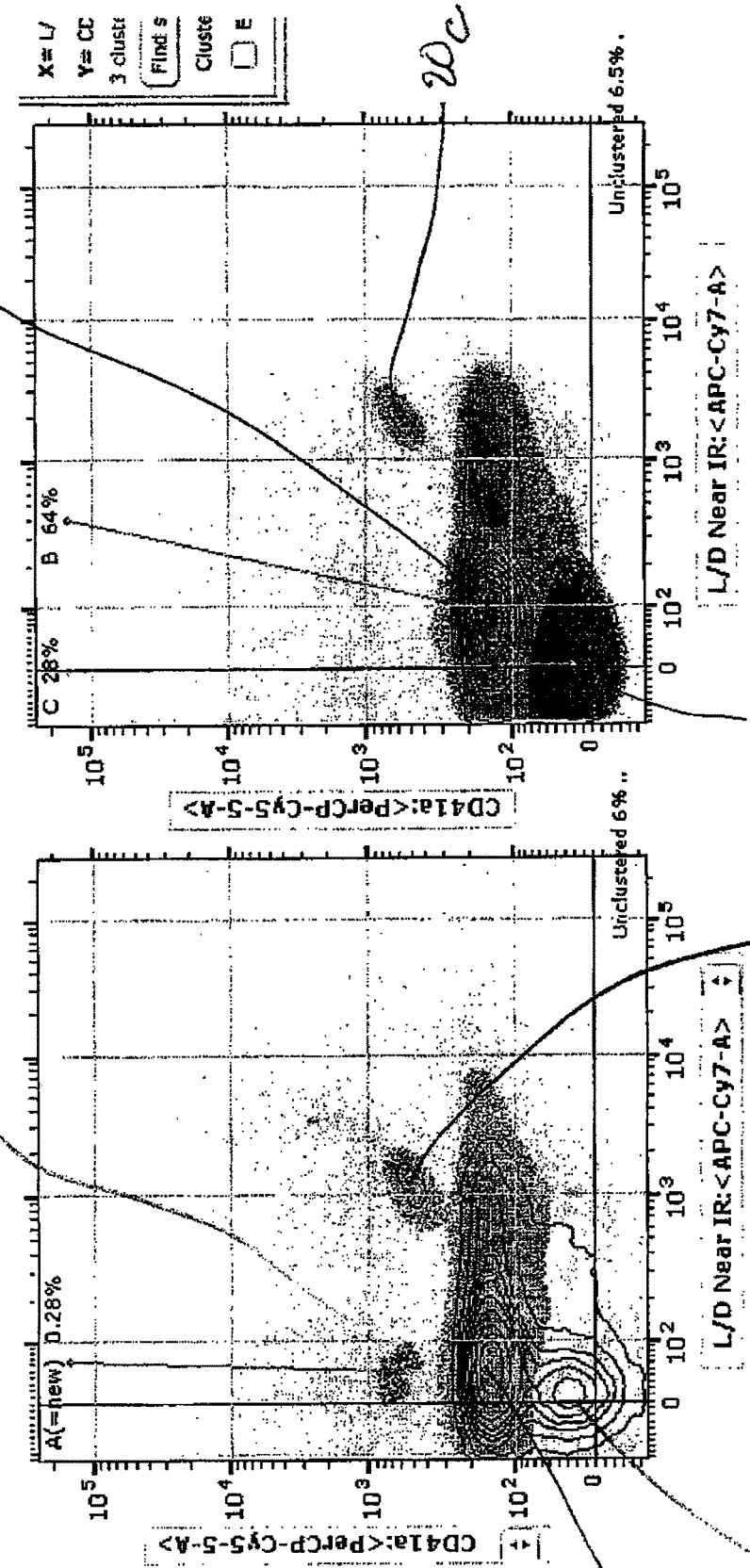

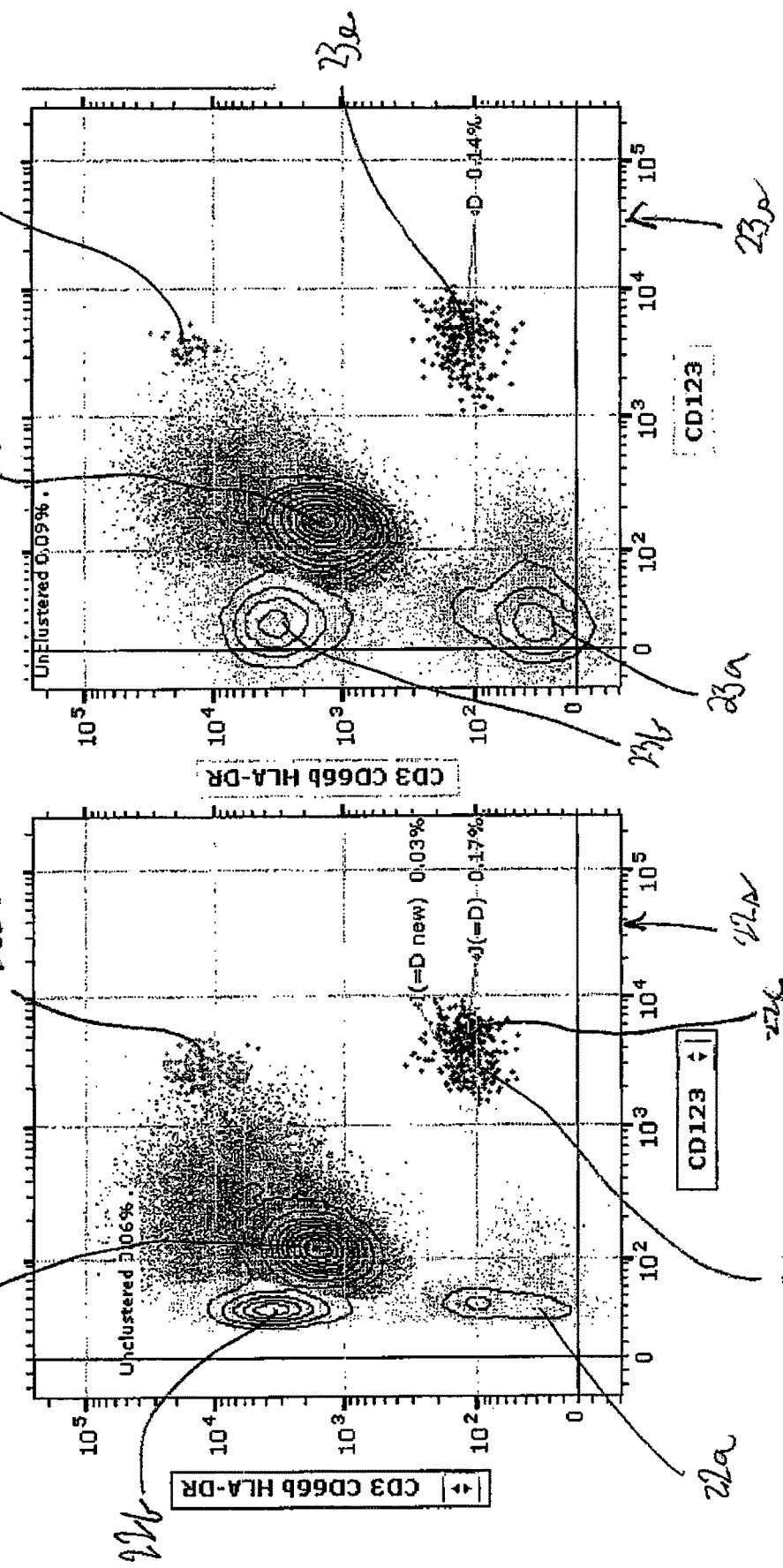

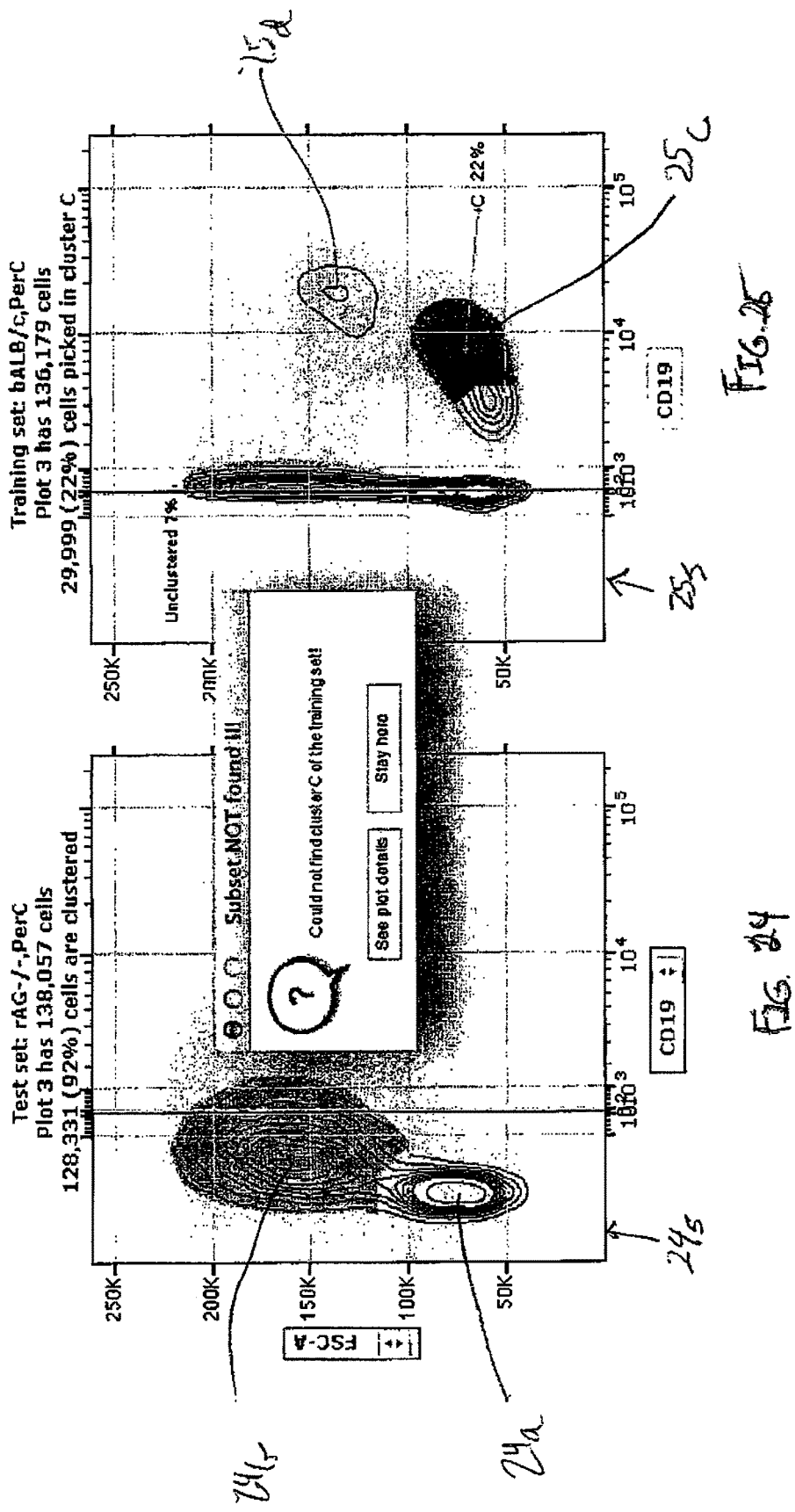

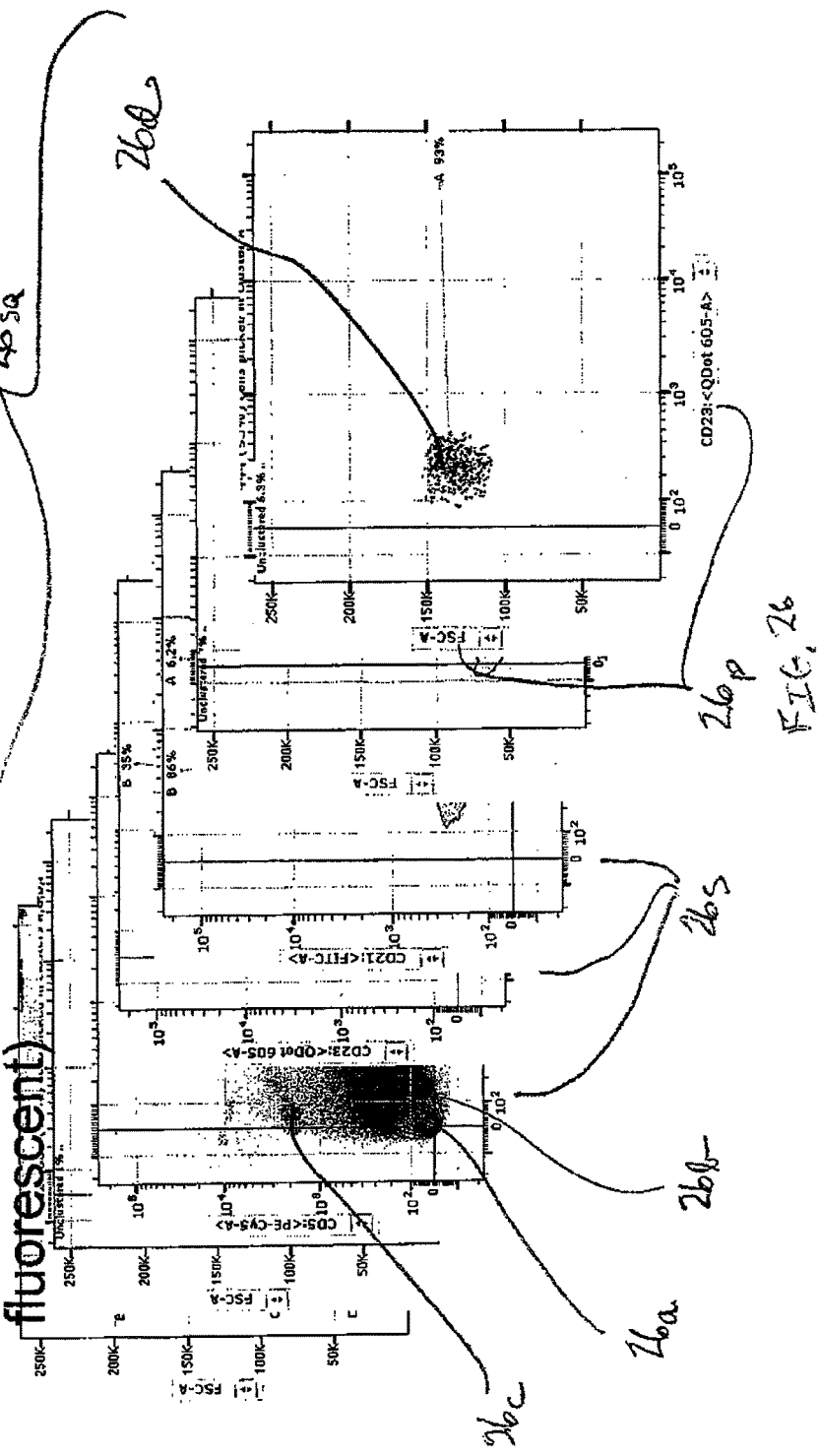

FIG. 30

AutoGate: Define controls & labels for "Stain set #1"

Please review the following associations, make changes if required

| Include | Instrument detector | Single-stained sample | Fluorophor/dye | Marker | Unstained sample |
|---|---|---|---|---|---|
| ▼ | FITC-A | FITC Stained Cont... ▼ | Fluorescein (FITC) ▼ | CD 43 ▼ | Unstained Co... ▼ |
| ▼ | PerCP-Cy5-5-A | PerCP-Cy5-5 Stai... ▼ | PerCP-Cy5.5 ▼ | IgM ▼ | Unstained Co... ▼ |
| ▼ | Pacific Blue-A | Pacific Blue Staine... ▼ | Pacific Blue ▼ | Dump ▼ | Unstained Co... ▼ |
| ▼ | Aqua Amine-A | Aqua Amine Stain... ▼ | Aqua Amine ▼ | L/D ▼ | Unstained Co... ▼ |
| ▼ | Pacific Orange-A | Pacific Orange St... ▼ | Pacific Orange ▼ | CD45 ▼ | Unstained Co... ▼ |
| ▼ | QDot 605-A | QDot 605 Stained ... ▼ | Qdot 605 ▼ | IgLambda ▼ | Unstained Co... ▼ |
| ▼ | APC-A | APC Stained Cont... ▼ | APC ▼ | IgE ▼ | Unstained Co... ▼ |
| ▼ | APC-Cy5-5-A | APC-Cy5-5 Staine... ▼ | APC-Cy5.5 ▼ | CD19 ▼ | Unstained Co... ▼ |
| ▼ | APC-Cy7-A | APC-Cy7 Stained ... ▼ | APC-Cy7 ▼ | CD27 ▼ | Unstained Co... ▼ |
| ▼ | PE-A | PE Stained Control ▼ | PE ▼ | IgD ▼ | Unstained Co... ▼ |

Save | X Cancel

FIG. 31

AutoGate: Associate stain sets with samples

| Multi-stained sample | Stain set for compensating | Stain set used by the sample |
|---|---|---|
| Dump+ Nasal CRS 2/6/2014, Specimen_002 | Stain set #1 | Stain set #1 |
| Nasal Full CRSsNP 2/06/14, Specimen_002 | Stain set #1 | Stain set #1 |
| Nasal Fulll CRSsNP 2/4/14, Specimen_002 | Stain set #1 | Stain set #1 |
| Nasal IgE FMO CRSsNP 2/4/14, Specimen_002 | Stain set #1 | Stain set #1 |
| Nasal IgM FMO CRSsNP 2/4/14, Specimen_002 | Stain set #1 | Stain set #1 |
| PBMC Full CRSsNP 2/06/14, Specimen_002 | Stain set #1 | Stain set #1 |
| PBMC Full CRSsNP 2/04/14, Specimen_002 | Stain set #1 | Stain set #1 |
| PBMC IgE FMO CRSsNP 2/4, Specimen_002 | Stain set #1 | Stain set #1 |
| PBMC IgM FMO CRSDsNP 2/6/14, Specimen_002 | Stain set #1 | Stain set #1 |
| PBMC IgM FMO CRSsNP 2/4/14, Specimen_002 | Stain set #1 | Stain set #1 |
| PPBMC IgE FMO CRSsNP 2/6/14, Specimen_002 | Stain set #1 | Stain set #1 |
| US Nasal CRS 2/6/2014, Specimen_002 | Stain set #1 | Stain set #1 |
| US PBMC CRS 2/6/2014, Specimen_002 | Stain set #1 | Stain set #1 |

Save    X Cancel

FIG. 32

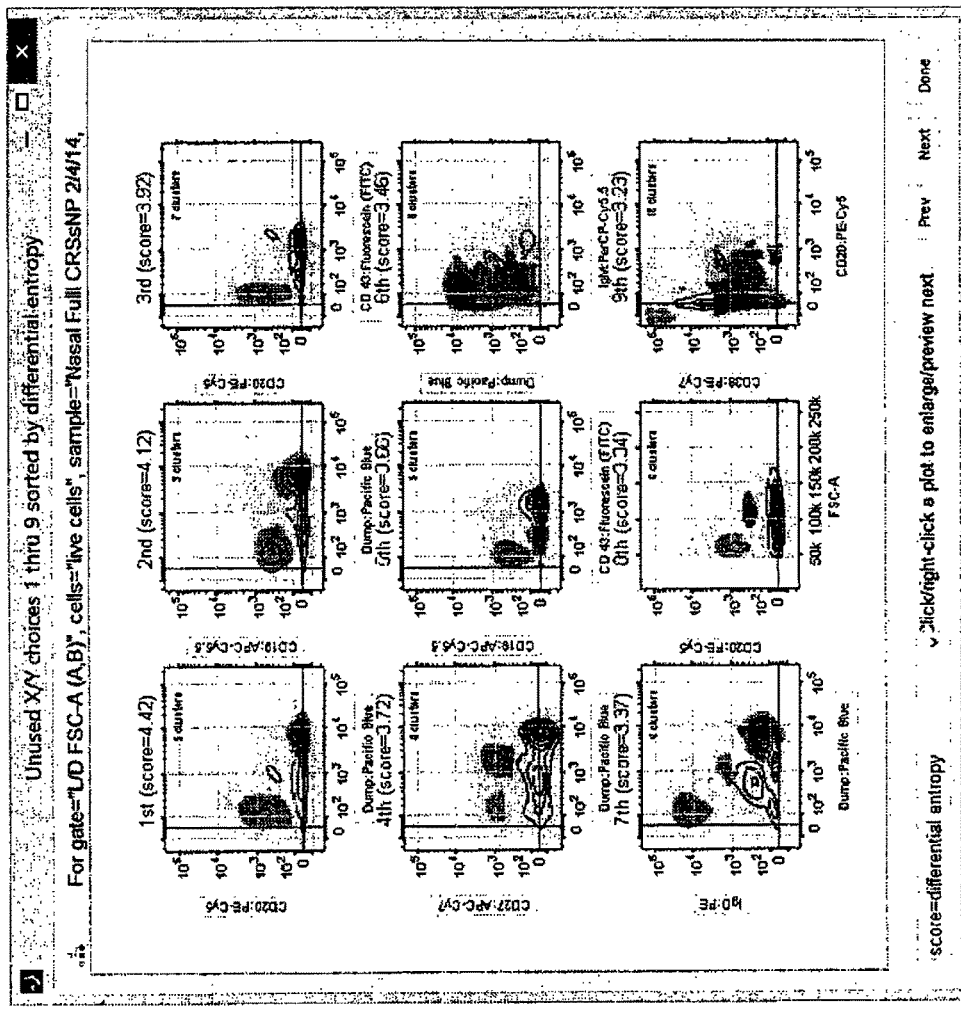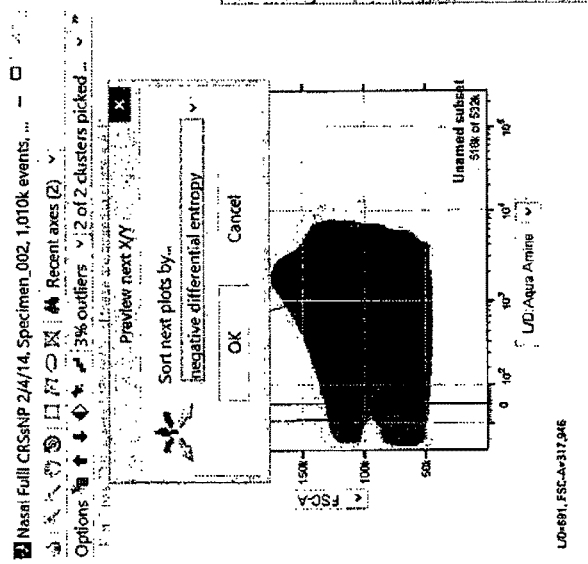
FIG. 38

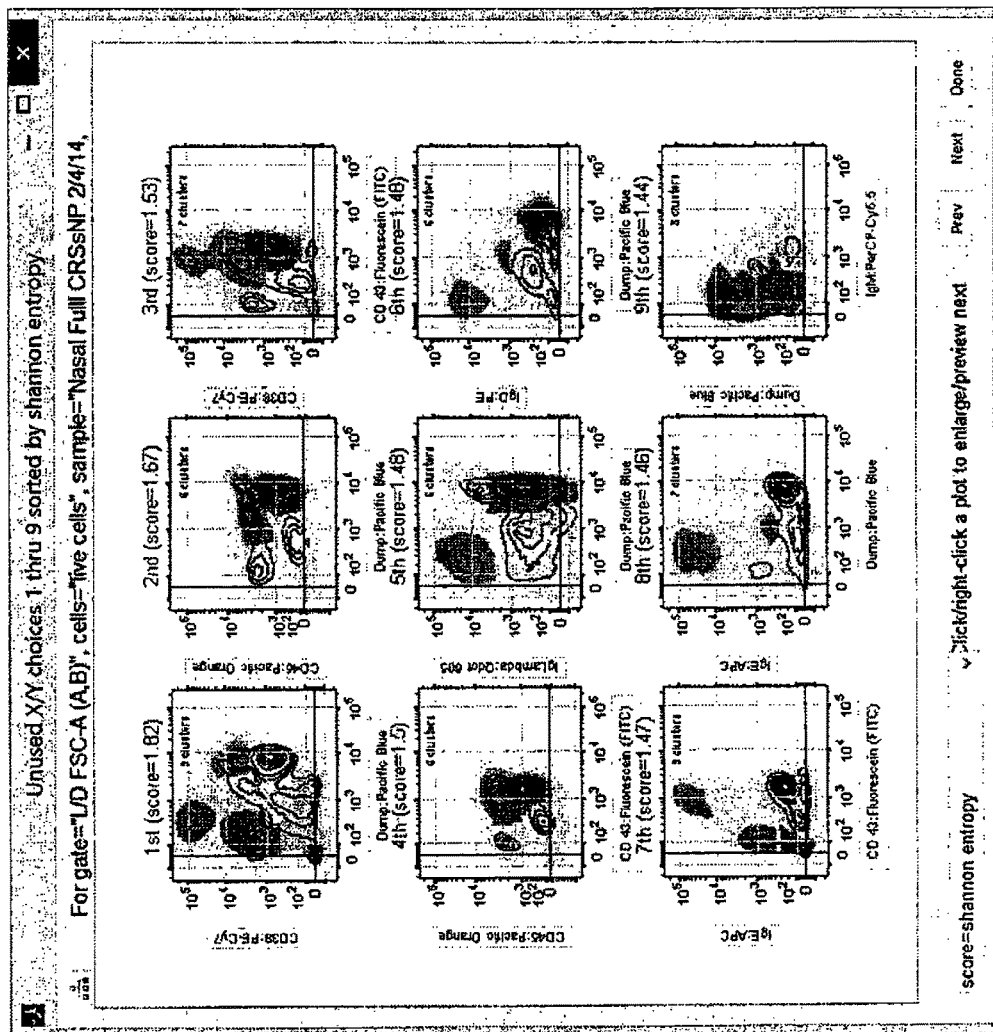
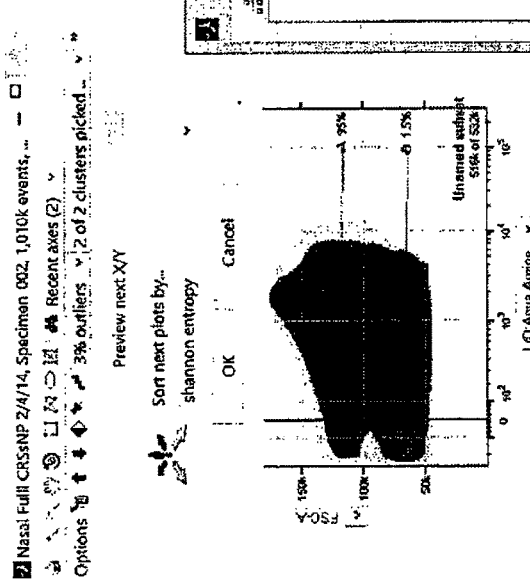
FIG. 39

CLUSTER PROCESSING AND RANKING METHODS INCLUDING METHODS APPLICABLE TO CLUSTERS DEVELOPED THROUGH DENSITY BASED MERGING

CROSS REFERENCE TO RELATED APPLICATIONS

This application claims priority to U.S. provisional application No. 61/981,422, filed 18 Apr. 2014, and is a continuation in part of U.S. application Ser. No. 13/342,722, filed 3 Jan. 2012, entitled, Quantitative Comparison of Sample Populations Using Earth Mover's Distance, which claims priority to U.S. provisional patent application No. 61/429,355, filed 3 Jan. 2011, the contents of which are incorporated by reference herein in their entirety.

STATEMENT OF GOVERNMENT FUNDING

This invention was made with Government support under contract HL068522 and LM007033 awarded by the National Institutes of Health. The Government has certain rights in this invention.

FIELD OF THE INVENTION

The present invention relates to the field of data analysis. More specifically, the invention relates to methods for clustering data associated with individual members of a population, such as when analyzing a large number of cells, e.g., using FACS, or in analyzing market or other data sets.

BACKGROUND OF THE INVENTION

In many different industrial, medical, biological, business, research and/or other settings, it is desirable to study large populations of individuals, where each individual has multiple measurable properties (dimensions). For example, a blood sample may contain a population of different cells in the $4^{th}$ or $5^{th}$ order of magnitude in number with a variety of different types of cells, each cell type having a substantial number of different measurable properties and with variations among individual cells due, e.g., to responses to environmental stimuli, developmental state, etc. For example, the cells may have a variety of different morphologies, substructures, cell surface molecules, different dimensions, different optical properties when illuminated by light, etc. In studying and testing the cells of a given sample, it may be desirable to identify, count and sort the cells of different types in the sample. One way of accomplishing those ends would be to employ the apparatus and techniques associated with the field of flow cytometry, wherein, inter alia, each of a population of cells is tested by exposure to light, e.g., a laser with a given frequency, magnitude and direction, and the response, e.g., fluorescence, absorption, reflection in a given direction and at a given magnitude, etc. is noted. This may be conducted in conjunction with a procedure for pre-conditioning the cells, e.g., by staining or subjecting them to a stimulus, such as an allergen. The light response data may be interpreted to identify sub-populations (sub-sets) in the sample, e.g., to count them and/or to physically separate them, e.g., for further examination, viz., based upon their responsive property when exposed to the light stimulus.

There are many other instances where large populations of individuals may be constructively analyzed by gathering data concerning the individuals and their measurable properties/attributes, which may be used to sort/characterize, group and/or count them. For example, in the area of marketing, a segment of the population of a country or many countries may be under consideration. Each of these persons may have multiple relevant or potentially relevant attributes that may contribute to their predisposition to purchase a given product or service or to do or refrain from a certain act. In addition, there may be numerous other properties of the individuals of a given population that are not relevant to any given propensity, such as a predisposition to buy a particular product. In addition, a given predisposition to buy may be indicated by the convergence of a plurality or even a multiplicity of properties of an individual and/or the absence of other properties. In the area of science, advancements have led to an explosion of available data, which is sometimes referred to as "Big Data" and apparatus and methods to harness and use this data are needed. See, "Drowning In Data," Chemical & Engineering News Feb. 18, 2013, Page 40.

Because the volume of data to be considered in these diverse instances is sometimes large, it remains desirable to develop systems that can automatically aid in the analysis of data pertaining to large populations of individuals or other entities, e.g., blood cells, with multiple measurable properties (dimensions).

SUMMARY

According to one aspect, the described invention provides a computer implemented method of identifying clusters of data items, wherein a data item is associated with one or more values using an information system comprising: defining a plurality of lattice points in a data space able to contain some of the data items of interest, the lattice points spaced according to a lattice rule; calculating weights for the lattice points using one or more of the data items according to a weighting rule; determining a density at the lattice points relating a weight at a lattice point to weights at nearby lattice points using a density function; creating, for a lattice point, a directional association with at least one other lattice point using an association rule; following directional associations between lattice points to determine terminal states for one or more pointer paths; assigning each data item to a lattice point according to an assignment rule; and using terminal states of the pointer paths to determine a cluster for the data item.

According to one embodiment, the data items are groups of values, each associated with an individual cell and the cluster is a cell subpopulation. According to another embodiment, the data items each represent market participants in an economic market; the values represent obtainable characteristic measures of a market participant; and the clusters each represent a category of market participants. According to another embodiment, the one or more values are effectively continuous.

According to one embodiment, the identifying one or more clusters uses directional associations of a plurality of lattice points and a density estimated at each lattice point and does not use weights assigned to lattice points or original data values.

According to another aspect, the described invention provides an apparatus for creating groupings from data comprising: means for assigning each piece of data from the set of data to a point on a lattice; means for assigning weights to each lattice point based on the data near the lattice point; means for determining for each of the lattice points if each of the lattice points should be associated with one of its surrounding lattice points and if so, creating a pointer from the individual lattice point to the surrounding lattice point it is associated with; and means for creating clusterings of the lattice points.

According to another aspect, the described provides a set of application program interfaces embodied on a computer-readable medium for execution on a computer in conjunction with an application program that determines clusters within a set of data, comprising: a first interface that receives data; a second interface that receives parameters; and returns groupings of the data.

According to another aspect, the described invention provides a method of clustering data items, wherein a data item is associated with one or more semi-continuous values, using an information system comprising: creating a reduction data item set, each reduction data item associated with one or more quantized values correlated with the one or more semi-continuous values; assigning each data item to a reduction data item according to an assignment rule; calculating weights for the reduction data items using one or more data items according to a weighting rule; determining for a plurality of reduction data items if it should be associated with another reduction data item according to an association rule; for at least one reduction data item, creating a directional association with at least one other reduction data item; and identifying one or more clusters of the reduction data items using one or more directional associations and/or one or more of the weights.

According to another aspect, the described invention provides a method enabling analysis of large sets of data observation points, each point having multiple parameters comprising: performing a first automated clustering of data points using a subset of the parameters using an information system, the first clustering providing one or more data clusters; selecting a first selected cluster; successively performing subsequent automated child clusterings on selected clusters, while optionally choosing different parameters allowing for the clustering.

According to another aspect, the described invention provides a method enabling analysis of large sets of data observation points, each point having multiple parameters using an information system comprising: displaying to a user results of an automated clustering of data points using a subset of the parameters, the first clustering indicating one or more data clusters; registering an input from the user selecting a first selected cluster from which to generate children clusters; providing an interface allowing a user to optionally choose different parameters allowing for the children clusters; and displaying a hierarchy of clustering results.

According to one embodiment, the step of calculating weights includes linear binning in accordance with the formula:

$$w_m = \sum_{i=1}^{n} \prod_{j=1}^{d} \max(0, 1 - |x_{i,j} - y_{mj}|/\Delta_j).$$

According to one embodiment, the step of determining a density includes computing an estimate of a density surface $\hat{f}(y_m)$ wherein the Gausian kernel is denoted by $\phi(b)=1/\sqrt{2\pi} \exp(-b^2/2)$ and the estimated density $y_m$ is computed by the formula:

$$\hat{f}(y_m) = 1/n \sum_{l_1=-Z_1}^{Z_1} \ldots \sum_{l_d=-Z_d}^{Z_d} \omega_{m-1} \prod_{j=1}^{d} \phi(l_j \Delta_j / h_j)/h_j,$$

where $l=(l_1, \ldots, l_d), Z_j=\min(\lfloor 4h_j/\Delta_j \rfloor, M-1)$, and $h_j=SD(\{x_{i,j}, i=1, \ldots, n\})n^{-1/(d+4)}$, where SD denotes standard deviation.

According to one embodiment, the formula:

$$\hat{f}(y_m) = 1/n \sum_{l_1=-Z_1}^{Z_1} \ldots \sum_{l_d=-Z_d}^{Z_d} \omega_{m-1} \prod_{j=1}^{d} \phi(l_j \Delta_j / h_j)/h_j,$$

where $l=(l_1, \ldots, l_d), Z_j=\min(\lfloor 4h_j/\Delta_j \rfloor, M-1)$, and $h_j=SD(\{x_{i,j}, i=1, \ldots, n\})n^{-1/(d+4)}$ is computed by the Fast Fourier Transform (FFT).

According to one embodiment, the step of determining a density includes calculating an estimate of the standard deviation of the density estimate in accordance with the formula:

$$\hat{\sigma}_m^2 = \frac{1}{n(n-1)} \sum_{l_1=-Z_1}^{Z_1} \ldots \sum_{l_d=-Z_d}^{Z_d} w_{m-1} \prod_{j=1}^{d} \phi^2(l_j \Delta_j / h_j)/h_j^2 - \frac{1}{n-1}\hat{f}(y_m)^2$$

and $$S = \{m \in \{1, \ldots, M\}^d : \hat{f}(y_m) > 4.3 * \sqrt{\hat{\sigma}_m^2}\}$$

defining an index set.

According to one embodiment, the step of creating a directional association includes establishing and removing pointers between neighboring lattice points by successively executing a series of evaluations for all lattice points $y_m$, where m is an element of S, in turn: considering all neighboring lattice points $p_1, \ldots, p_{nm}$ which are defined as the set of all lattice points contained in a s-dimensional rectangular volume. Let p be an element of $\{p_1, \ldots, p_{n\,m}\}$ such that $\hat{f}(p)=\max_{k=1, \ldots, nm} \hat{f}(p_k)$, splitting ties in an arbitrary manner; then a pointer is established from $y_m$ to p provided:

$\hat{f}(p) > \hat{f}(y_m)$; and $$\frac{\partial}{\partial e} \hat{f}(y_m) > \lambda_m,$$

where $e=(p-y_m)/\|p-y_m\|$, $\|\cdot\|$ denotes Euclidean norm, and $$\frac{\partial}{\partial e} \hat{f}(y_m) = \sum_{a=1}^{d} e \frac{\partial}{\partial y_{m_a}} \hat{f}(y_m),$$

which indicates a gradient of the density estimate, $$\frac{\partial}{\partial y_{m_a}} \hat{f}(y_m) = 1/n \sum_{l_1=-Z_1}^{Z_1} \ldots \sum_{l_d=-Z_d}^{Z_d} w_{m-1} \frac{-l_a \Delta_a}{h_a^2} \prod_{j=1}^{d} \phi(l_j \Delta_j / h_j)/h_j$$

-continued $$\lambda_m = q(0.95^{1/\kappa})\sqrt{\hat{\Sigma}_m^2}$$

$$\kappa = \frac{\#S \sum_{m \in s} w_m}{n(2\pi)^{d/2} \sum_{j=1}^{d} h_j \sum_{m \in s} w_m \hat{f}(y_m)}$$

$$\hat{\sum}_m^2 = \frac{1}{n-1}\left(\sum_{a,b=1}^{d} e_a e_b \left[A - \frac{\partial}{\partial y_{m_a}}\hat{f}(y_m)\frac{\partial}{\partial y_{m_b}}\hat{f}(y_m)\right]\right)$$

$$A = 1/n \sum_{l_1=-Z_1}^{Z_1} \ldots \sum_{l_d=-Z_d}^{Z_d} w_{m-1} \frac{l_a l_b \Delta_a \Delta_b}{h_a^2 h_b^2} \prod_{\varphi=1}^{\delta} \phi^2(l_j \Delta_j/h_j)/h_j^2,$$

A being an estimate of $$\frac{\partial}{\partial y_{m_a}}f(y_m)\frac{\partial}{\partial y_{m_b}}f(y_m)$$

and q(x) denotes the 100*xth percentile of the standard normal distribution.

According to one embodiment, each lattice point $y_m$, where m is not an element of S, a pointer is established that points to a state representing background noise.

According to one embodiment, the step of following directional associations further includes the evaluation: for all lattice points $y_m$, where m is an element of S, in turn: if a pointer originates at $y_m$, then it will point to a different lattice point, which itself may have a pointer originating from it; following a succession of pointers until a lattice point $y_Z$ is reached that either (a) does not have any pointer originating from it or (b) has a pointer originating from it that points to a state representing a cluster or background noise; in the event (a) removing all pointers visited in the succession and establishing new pointers originating from each lattice point to the background noise state, provided $\hat{f}(y_z) < q(0.95^{1/\kappa})\sqrt{\hat{\sigma}_z^2}$, otherwise only the pointer originating from $y_Z$ is removed and a new pointer is established that originates from $y_Z$ (if any) is removed and a new pointer is establishes that originates from $y_Z$ and points to a new cluster state, in the event (b) no pointers are removed or established.

According to one embodiment, wherein the step of following directional associations further includes the following steps:

Let $\{y_{m(1)}, \ldots y_{m(k)}\}$ be the set of all lattice points which have a pointer originating from them to a dummy state representing a cluster, enumerated such that $\hat{f}(y_{m(1)}) \geq \ldots \geq \hat{f}(y_{m(k)})$ and for i=1, ..., k do: set A={m(i), and iterate the following loop until no more indices are added to A: (Begin loop) For each index a which is an element of A in turn, add all the indices p to A that satisfy: Yp is a neighbor or ya as defined in claim 15, and No pointer originates from yp, and $\hat{f}(y_p) + \hat{\sigma}_p \geq \hat{f}(y_{m(i)}) + \hat{\sigma}_{m(i)}$ (End loop) Denote by B the set of indices of lattice points from which a pointer originates to a cluster state and that also have some $y_p$, p being an element of as neighbor. If B is not empty, then do the following: Define q by $\hat{f}(y_q) = \max_{r \in B} \hat{f}(y_r)$, breaking ties arbitrarily; Establish a pointer from each $y_p$, p an element of A\{m(i)} to $y_q$; For each r which is an element of B, if r≠q, remove the pointer from $y_r$ to the state representing a cluster and establish a new pointer from $y_r$ to $y_q$.

According to one embodiment, the steps recited are repeated until there are no more additions or deletions of pointers to cluster state.

According to one embodiment, each lattice point that does not have a pointer originating from it, a pointer is established pointing to the background noise state.

According to one embodiment, a data set that has more than two dimensions, individual clusters can be subdivided according to values measured in dimensions other than those used to define the cluster.

According to one embodiment, the method is used recursively to create a tree structure comprising one or more successive nodes (child) in the tree obtained by clustering the preceding (parent) node.

According to another aspect, the described invention provides computer implemented method for guiding clustering strategy comprising: (a) calculating dimension pairs entropy-based ranking score; (b) displaying to a user results of an automated dimension pairs entropy-based ranking; and (c) receiving and implementing the user's dimension-pair choice.

According to one embodiment, the computer readable medium is a contained software environment.

Many variations according to the invention will be understood from the teachings herein to those of skill in the art.

BRIEF DESCRIPTIONS OF THE DRAWINGS

FIG. 1 illustrates an example of a portion of one type of data set that can be analyzed according to some embodiments of the invention.

FIGS. 15 and 16 are diagrammatic depictions of clusters from training data and test data respectively.

FIG. 17 is a diagram showing overlap between the clusters shown in FIGS. 15 and 16.

FIGS. 18 and 19 are screen shots showing a comparison of clusters between two successive samples of populations of cells and the detection of the clusters in each, representing the same types of cells.

FIGS. 20 and 21 are screen shots showing a comparison of clusters between two successive samples of populations of cells and the detection of a new cluster in FIG. 20 that was not present in FIG. 21.

FIGS. 22 and 23 are screen shots showing a comparison of clusters between two successive samples of populations of cells and the detection of new clusters in FIG. 22 that were split from a cluster present in FIG. 23.

FIGS. 24 and 25 are screen shots showing a comparison of clusters between two successive samples of populations of cells and the detection of a missing cluster that was previously present in a first sample.

FIG. 26 shows a series of screen shots of clusters identified by a sequence of different parameters leading to the identification of a specific subset of a population.

Figure 30:
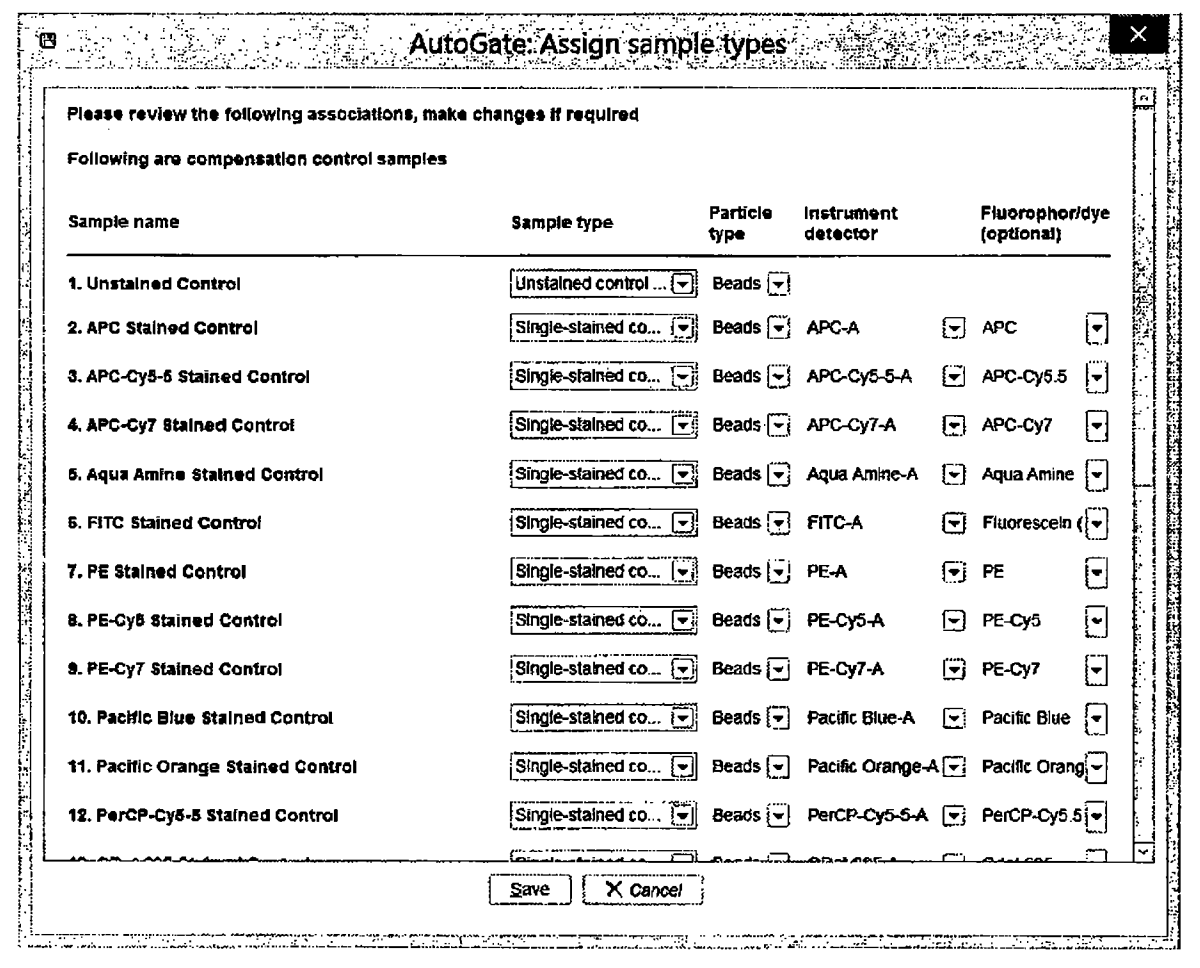

FIG. 30 shows screen shot for assigning sample types.

FIG. 31 shows screen shot for defining controls and labels for a stain set.

FIG. 32 shows a screen shot for associating stain sets with samples.

FIG. 38 shows screen shots of plots sorted by negative differential entropy.

FIG. 39 shows screen shots of plots sorted by shannon entropy.

Figure 40:
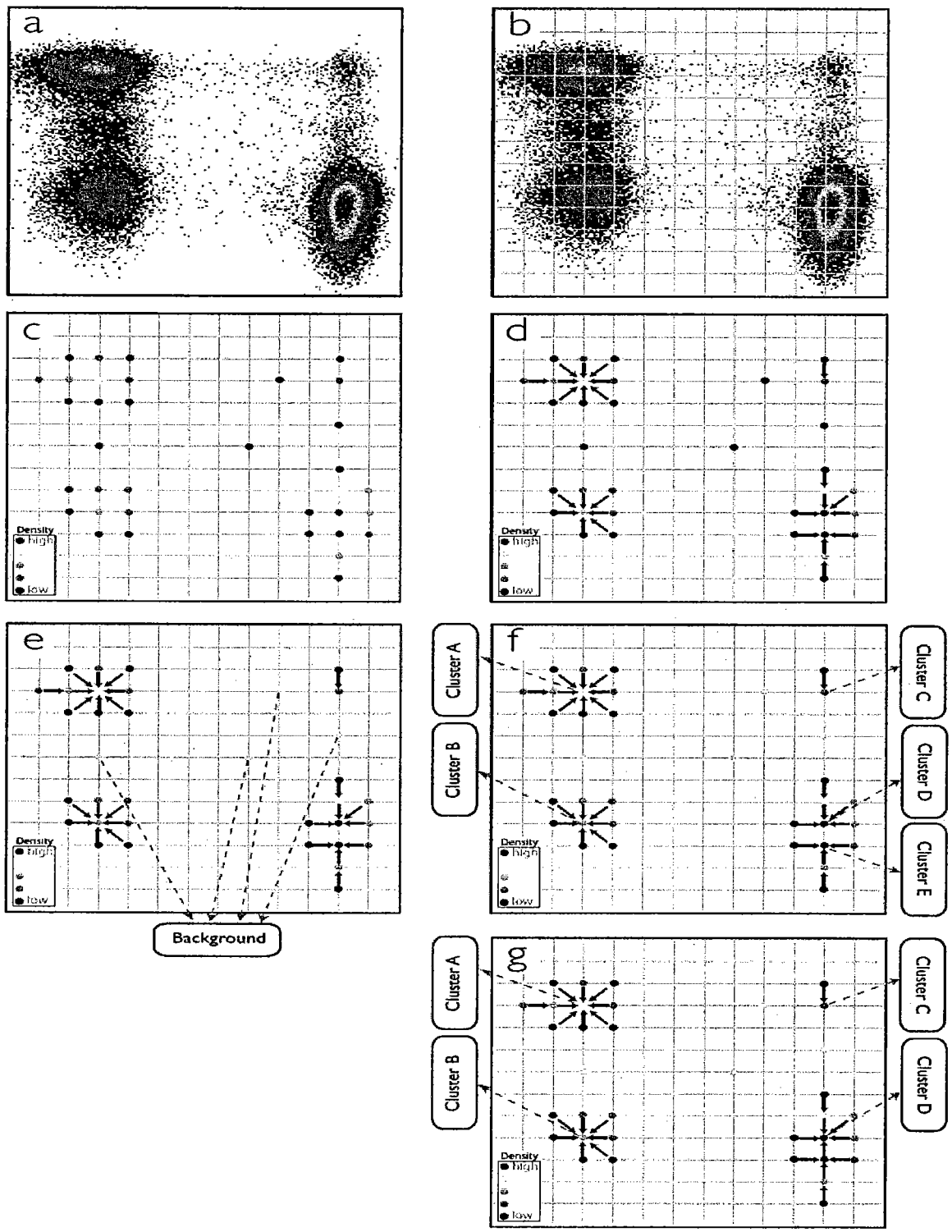

FIG. 40 shows the steps of the DBM algorithm as applied in one round of recursive DBM gating. Panel "a" depicts a distribution on a grid. Panels "b" and "c" depict the estimate of the density at each grid point. Panel "d" depicts construct association pointers between grid points that follow the gradient ascent. Panel "e" depicts a determination of background outliers. Panel "f" depicts the assignment of each grid point to a cluster or to background. Panel "g" depicts the merger of clusters that are not separated by a statistically significant through.

Figure 41:
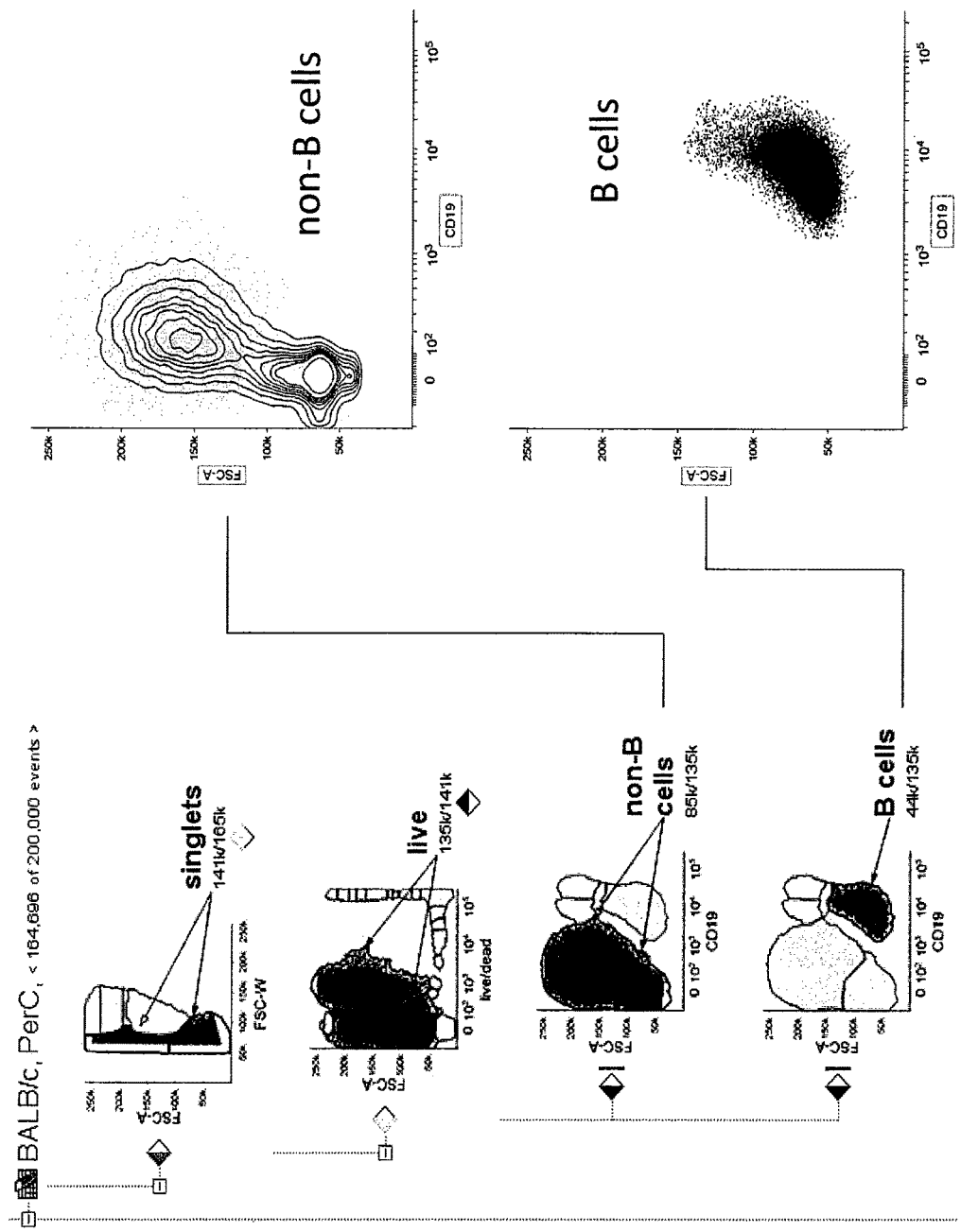

FIG. 41 shows sequential gating using DBM clustering (as implemented in AutoGate). Cells were obtained from the peritoneal cavity, stained for expression of the indicated determinants and analysed by flow cytometry. Colors distinguish subsets detected by AutoGate. Left: An AutoGate gating tree. Right: further AutoGate analysis of the indicated subset(s) to reveal "child" subset(s) identified by additional marker expression.

Figure 42A:
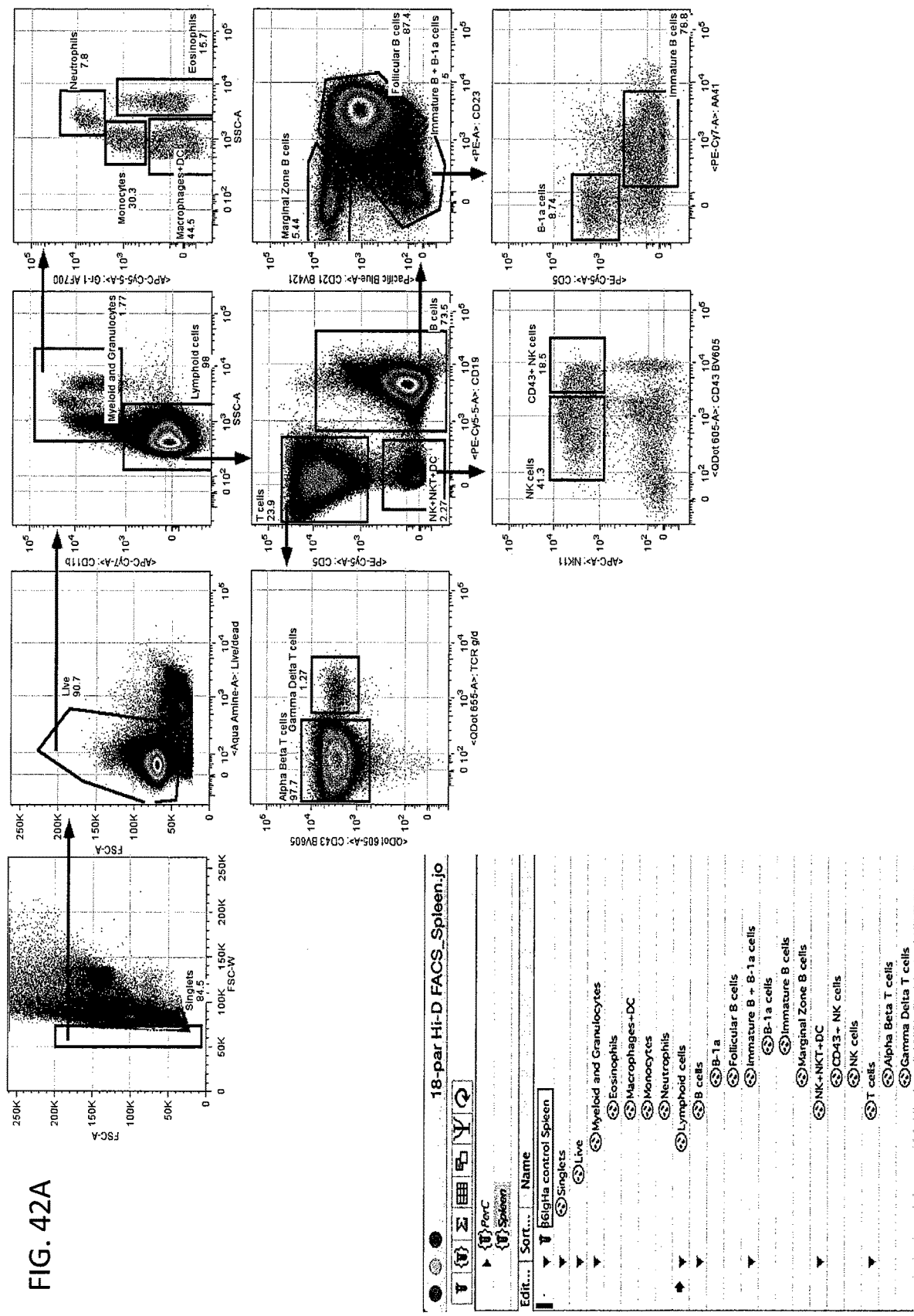
Figure 42B:
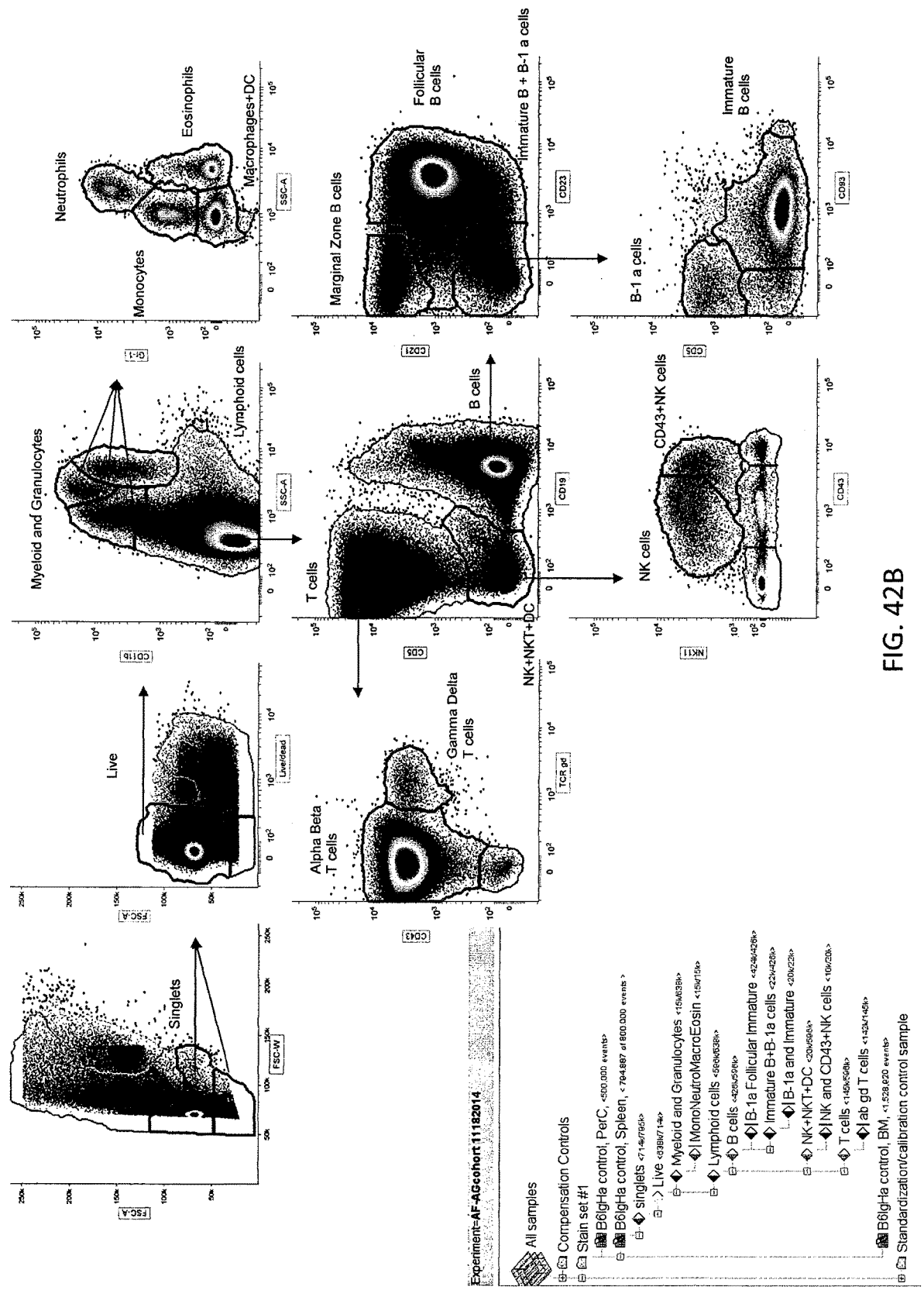
Figure 42C:
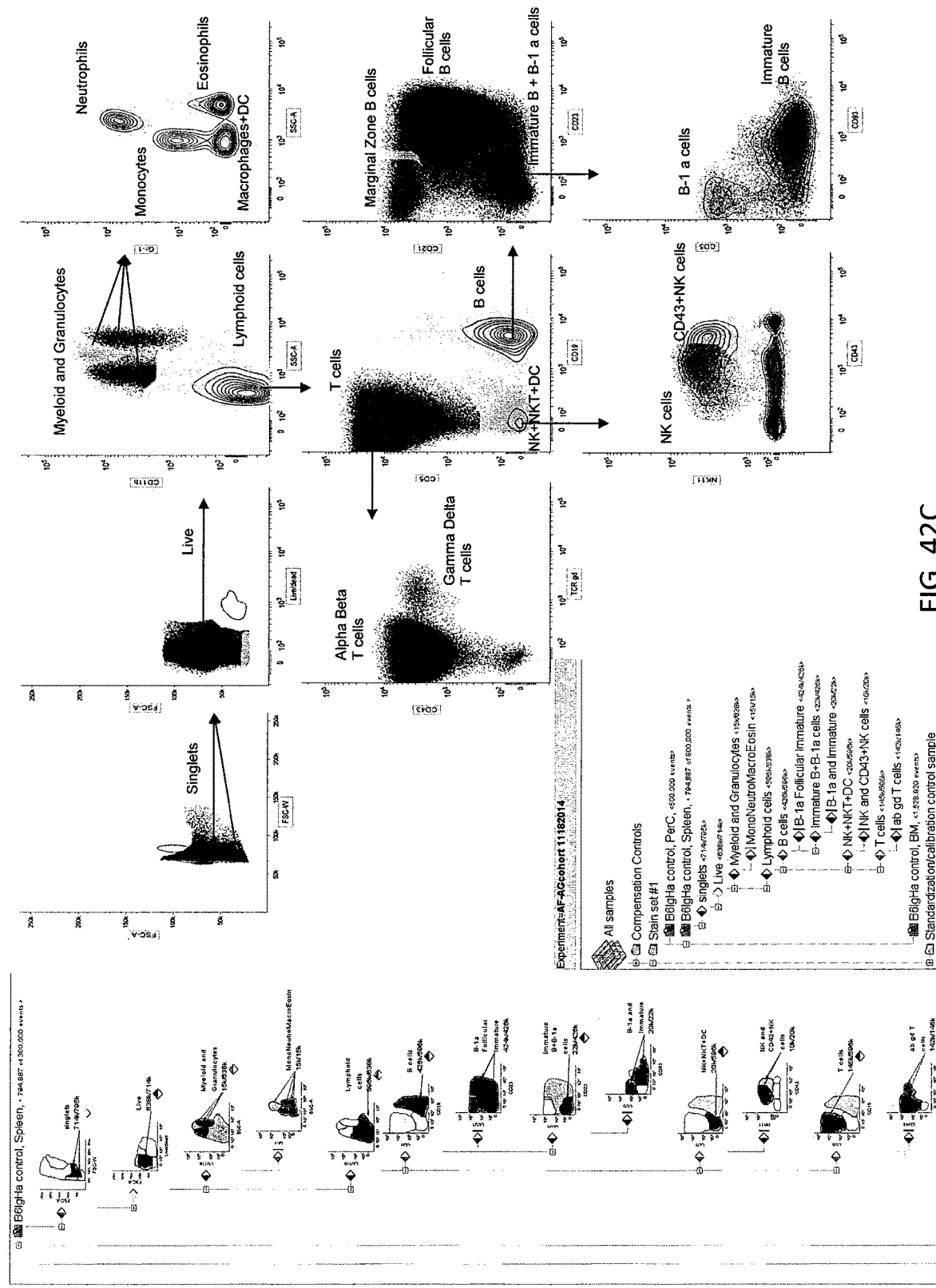

FIGS. 42A, 42B and 42C shows a comparison of manual (FlowJo) and automated (AutoGate) projection pursuit analysis of Hi-D (18 parameter) flow cytometry data. Spleen from wild-type B6-IgHa mice were processed into single cell suspensions and stained with fluorochrome-conjugated monoclonal antibodies in an 18-parameter Hi-D flow cytometry panel (16-color+Side and Forward Scatter) that identifies the following immune system subsets: lymphocytes (B, T, NK/NKT cells), myeloid cells (monocytes, macrophages, and dendritic cells), and granulocytes (neutrophils and eosinophils). Within the overall lymphocyte subset, the B cell subsets are further subdivided into four phenotypically distinct subsets: follicular B, marginal zone B, immature B, and B-1a; and the T cells into gamma/delta and alpha/beta T cells. Data were collected for 0.8-1×10$^6$ cells with Stanford Shared FACS Facility instruments (Becton Dickinson LSR-II). FIG. 42A depicts data analyzed with FlowJo software (v9.8.2, TreeStar.com). Top and Right: screen shots for clustered data. Bottom-left: screen shot of a FlowJo gating tree. FIG. 42B depicts data analyzed with AutoGate software (v1.165, CytoGenie.org). Top and Right: screen shots for clustered data. Bottom-left: screen shot of an AutoGate gating tree. FIG. 42C depicts data analyzed with AutoGate software (v1.165, CytoGenie.org). Left and Bottom-left: screen shots of AutoGate gating trees. Top and Right: screen shots for clustered data.

Figure 43:
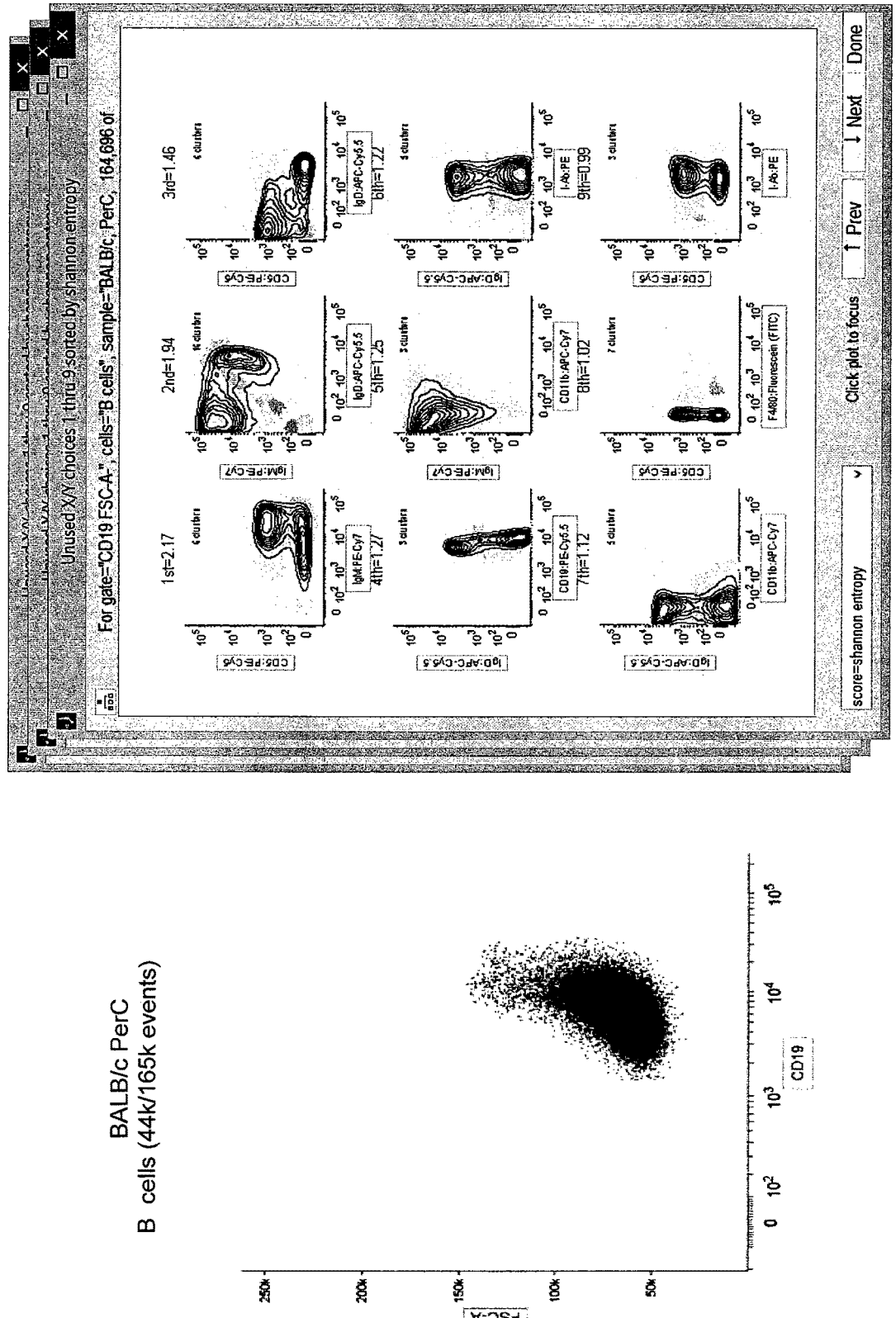

FIG. 43 shows an AutoGate "thumbnail" preview of clustered data. 9/36 pairs (9-color flow cytometry assay) are shown in descending order of Shannon entropy score.

Figure 44:
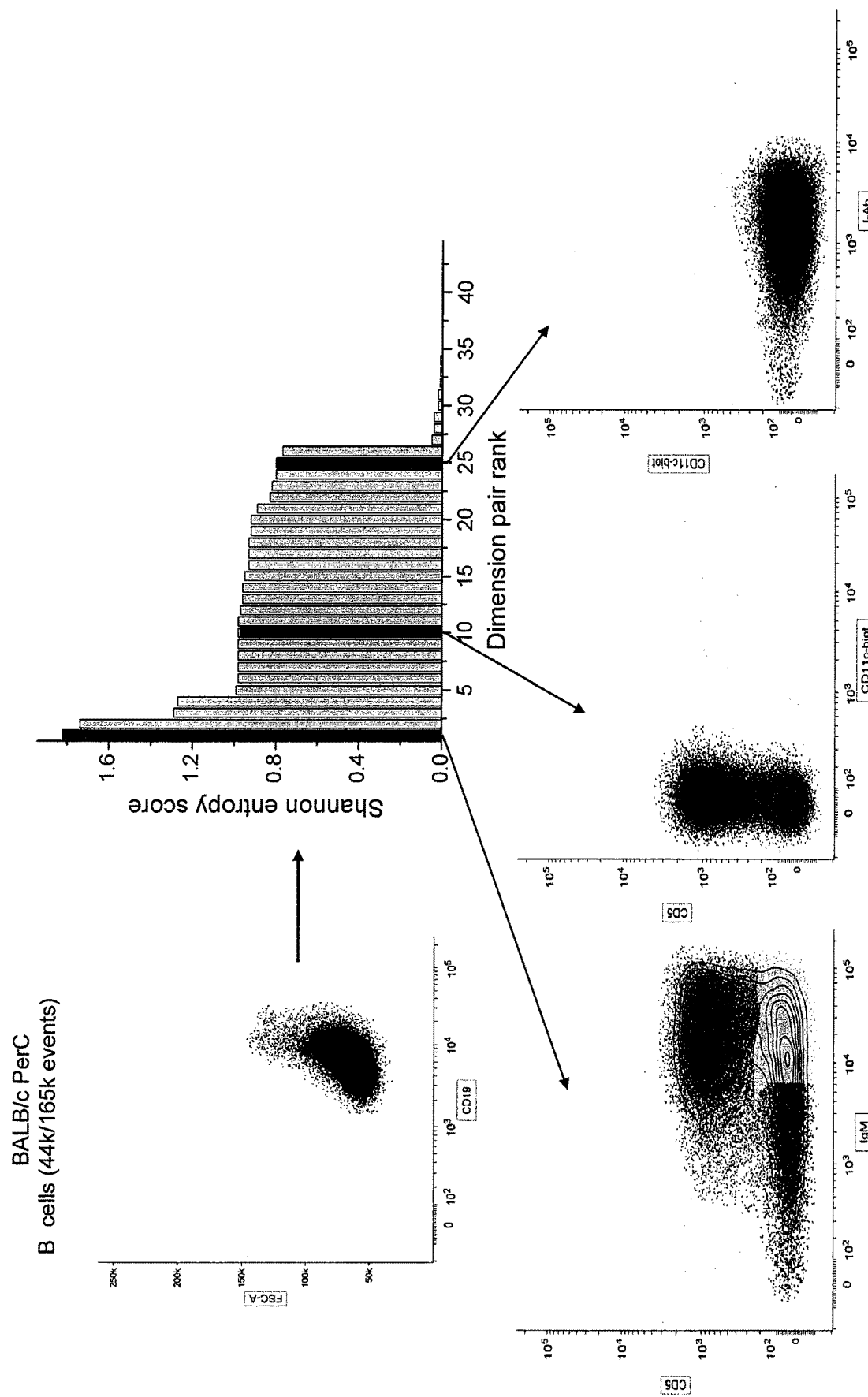

FIG. 44 shows all dimension pairs ranked according to Shannon Entropy score. The computed value reflects a combination of the uniformity of data distribution among clusters and the total number of clusters in the chosen pair of dimension. Shannon Entropy is maximal when the data is uniformly distributed among the highest possible number of clusters identified for a given dimension pair.

Figure 45:
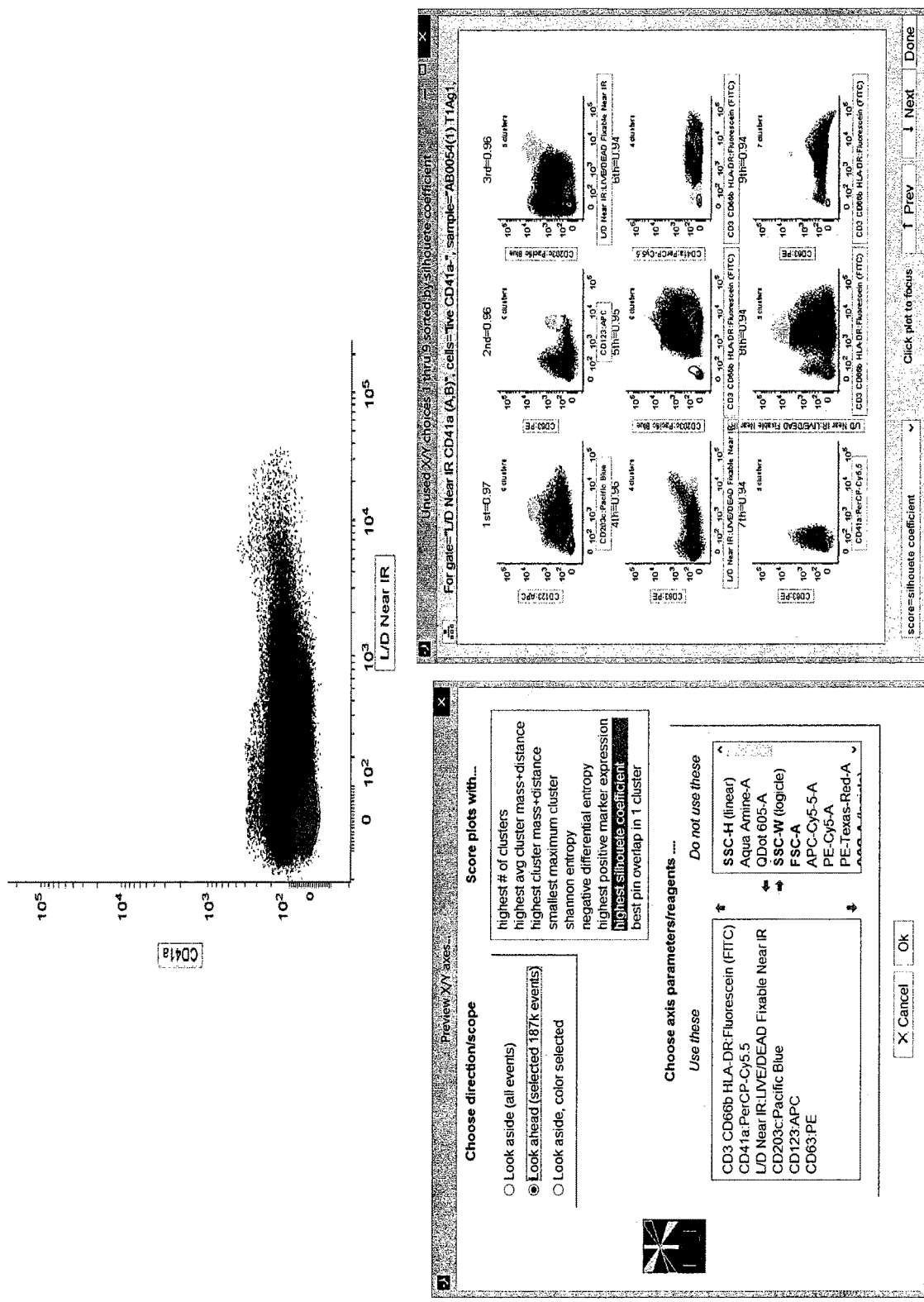

FIG. 45 shows the calculation of dimension pairs using Silhouette Coefficient-based ranking score.

DETAILED DESCRIPTION OF THE INVENTION

1. Definitions

The term "lattice" as used herein refers to a mathematically relationship relating to one or many dimensional analysis and represents a rules-based ordering of values used as a reference framework for performing analysis of various data-sets. Data analysis according to the present invention can be performed using reference values whether or not those values are described or describable as a lattice. For ease of illustration, a lattice herein may be drawn and discussed as comprising a two-dimensional, regular, finite and linear lattice. However, the present invention can be used with any system for determining coordinates in a data space, including lattices in three-dimensions, and higher dimensions, as well as non-linear regular lattices including logarithmic lattices, sinusoidal based lattices, etc., and rules-based lattices.

The term "lattice point" as used herein refers to a data reduction point or region in any data space in which a lattice is defined. Thus a lattice point can have one, two, three, sixteen or any number of coordinates as appropriate for a dataspace. Placement of a lattice point can be accomplished a number of ways, including a geometric center in the number of coordinates of the dataspace, at predefined interstitial points on the lattice in a data space, etc.

The term "DBM" as used herein refers to density based merging as described below and in U.S. patent application Ser. No. 10/832,992 (incorporated herein by reference). Density-based merging (DBM) is grounded in nonparametric statistical theory which allows for such subpopulations. DBM follows the paradigm that clusters of the data can be delineated by the contours of high-density regions. This also is the rationale that underlies manual gating. The paradigm is implemented algorithmically (Walther, G., et al., Advances in Bioinformatics, Vol. 2009, Article ID: 686759) by constructing a grid with associated weights that are derived by binning the data. This grid provides for a fast computation density estimated via the Fast Fourier Transform, and it provides for an economical but flexible representation of clusters. Each high-density region is modeled by a collection of grid points (Walther, G., et al., Advances in Bioinformatics, Vol. 2009, Article ID: 686759). This collection is determined as follows: 1) links are established between certain neighboring grid points based on statistical decisions regarding the gradient density estimate. The aim is to connect neighboring grid points by a chain of links that follow the density surface "uphill." The result is a number of chains that link certain grid points and which either terminate at the mode of a cluster or represent background that will not be assigned to a cluster; 2) the algorithm then will combine some of these chains if statistical procedures indicate that they represent the same cluster. The end result of the algorithm results in clusters that are represented by chains that link certain grid points. This representation provides an efficient data structure for visualizing and extracting the cells that belong to a cluster (Walther, G., et al., Advances in Bioinformatics, Vol. 2009, Article ID: 686759). The chains that link grid points in a cluster represent a tree structure which can be traversed backwards to efficiently enumerate all grid points in the cluster and hence to retrieve all cells in the cluster via their nearest neighbor grid point. Software implementation of DBM can allow for automatic 2D gating that is based on statistical theory and provide the information necessary to decide on the number of populations in the sample (Walther, G., et al., Advances in Bioinformatics, Vol. 2009, Article ID: 686759).

The term "dimensions-ranking score" as used herein refers to a mathematical relationship between plots defined by distinct dimension pairs (axes). Rank score can be calculated in a number of ways. Data analysis according to the present invention can be performed employing information theory, notably entropy theory, to rank dimension pairs with respect to cluster separation and/or shape.

Entropy in this method provides a measure of how far away from a normal/uniform distribution a data set is, where a normal/uniform distribution is a prototype for a simple cluster including all of the data in the data set being analyzed. A data set with a large standardized negative differential or Shannon entropy value will exhibit a large amount of 'structure', i.e., it will have two or more distinguishable clusters. Since we are interested discovering dimension pairs that reveal such structures, and we are interested in ranking dimension pairs according to how much structure they reveal, we can use standardized negative differential or Shannon entropy as a measure to rank the dimension pairs. We present methodology based on two variations of entropy theory: differential and Shannon entropy. Each of these can be applied to Big Data, for example, to flow data at different steps of DBM algorithm realization to enable a choice of the "best" dimension pairs to use at a given step. This readily automatable approach, we suggest, will offer users a promising guide to choices of dimension pairs as data analysis progresses.

2. Description of General Method

According to embodiments of the invention, a method of the invention can be understood within the art of data analysis, particularly statistical analysis and set analysis. The following description of general methods is presented in a particular order to facilitate understanding and it will be understood in the art that according to some embodiments of the invention various steps can be performed in different orders and can be organized in different ways. The contents of the following previously filed U.S. applications are incorporated by reference herein in their entirety: U.S. application Ser. No. 10/832,992, filed Apr. 26, 2004, entitled Population Clustering Through Density-Based Merging, which claims priority to U.S. provisional patent application No. 60/465,703, filed 25 Apr. 2003; U.S. application Ser. No. 13/342,722, filed 3 Jan. 2012, entitled, Quantitative Comparison of Sample Populations Using Earth Mover's Distance, which claims priority to U.S. provisional patent application No. 61/429,355, filed 3 Jan. 2011; and U.S. application Ser. No. 12/610,940, filed 2 Nov. 2009, entitled Methods and Assays for Detecting and Quantifying Pure Subpopulations of White Blood Cells in Immune System Disorders. A familiarity with the field of data set analysis and the reference mentioned herein will aid in understanding the invention.

Data Set

According to some embodiments of the invention, a data set of observations is analyzed to determine meaningful clusters. For purposes of understand the invention, consider a large data set of n observations, where n can be very large, such as n » $10^6$. FIG. 1 illustrates an example of a portion of one type of data set that can be analyzed according to some embodiments of the invention. In a variety of different fields, each observation of interest will have associated with it a number of parameters where each parameter (or dimension) can represent some observed or calculated or predicted parameter relative to observation and/or sample $x_i$. For example, with FACS data, dimensions may include intensities of light at various wavelengths measured for a particular cell and/or group and/or sample of cells. In market analysis, each dimension may be a measure of a characteristic and/or prediction and/or observation related to a market participant $x_i$. In genetic analysis, parameters can be different states that a specific DNA/RNA location can represent. In protein analysis, each observation could be an amino acid and each parameter an angle or folding configuration or other state of the amino acid in a protein.

The Cluster Model

According to specific embodiments of the invention, it is assumed that the observations can be clustered into at least two groups or clusters, with one of the clusters potentially being a background state or a cluster representing observations that are due to noise, etc. According to some embodiments of the invention, the invention uses a method that can be employed on an information system to automatically identify clusters of data points in a multidimensional data set.

In a data set that has more than two dimensions, individual clusters can be subdivided according to values measured in dimensions other than those used to define the cluster.

According to some embodiments, the described invention provides a method for displaying cluster results by drawing precise borders around the regions of the 2-dimensional (2D) plot that contain only data points for a single cluster. The method uses the cluster IDs associated with each grid point in the grid produced by DBM. The method isolates as edge grid points all grid points that have a neighboring grid point not associated with the same cluster ID. Then it orders the edge grid points and connects them with a line that does not cross itself. In some applications there may be more than one such border for a cluster. For example a large cluster envelopes other clusters.

According to some embodiments, a user can look at, for example, the outcome of each step, or between any two steps, before moving forward with the series of steps that can be performed. According to some embodiments, the series of steps that can be performed is conducted in a fully automatic mode, meaning that the system (a) uses an algorithm to make the choice of which parameters will be used next, starting at any step, (b) makes its own choices as to pathway, and (c) reports results. According to some embodiments, the described invention performs all clustering for a selected data set and selected dimensions without further user intervention. According to some embodiments, the described invention can process data obtained from a data source characterized by data that has been processed either manually or automatically by another system, and when complete, can transfer outcomes to another entity, instrument or program.

According to some embodiments, the described invention provides a method for fully clustering all of the data in all of the dimensions without requiring the user to do anything more than choose the sample that is to be clustered. For example, the user does not have to select dimensions (reagents) of a given 2D plot or select 1 or more clusters in that 2D plot for the next 2D plot. In one embodiment the method combines the DBM clustering with the ranking metrics (Shannon entropy, negative differential entropy and silhouette coefficient). In one embodiment the 2D plots that rank the best are used and each cluster or merger of neighboring cluster is chosen for the next data set. In one embodiment a given set or subset of data is clustered on all possible pairs of dimensions. In one embodiment a given set or subset of data is clustered on a given subset of possible dimension pairs.

The clustering model can be used recursively to create a tree structure in which each successive node (child) in the tree is obtained by clustering the preceding (parent) node Branching occurs when a clustered parent node gives rise to more than one child cluster.

The described invention employs novel methods to do so the above even in large data set environments.

Data Reduction

Lattice/Grid

According to some embodiments of the invention, a lattice or grid is determined in the data space according to a lattice rule. In generally terms, the lattice can be understood as simply a regular and normalized lattice in the number of dimensions and with normalization set to take account of a set of data points of interest. According to one embodiment, the lattice has the same number of intervals in all directions. In this case, a lattice with M intervals in each direction will define Md lattice points.

Weighting

According to some embodiments of the invention, each lattice point is assigned a weight that is based on one or more of the observed data points. Weights can be assigned in a number of fashions, but can be understood as the average of all the values in the data set near that point. According to some embodiments, the region of the average for determining weights may be reduced.

Density Estimate

With the lattice points defined and each point having a set of weighted parameter values associated with it, the described invention next determines an estimated density surface that allows lattice points to be compared.

Determining Pointers/Paths Between Lattice Points

Using the lattice points, weights, and surface, the described invention next traces out one or more paths between the lattice points. This analysis can be performed by beginning at any lattice point and making a directional connection to one of the surrounding lattice points following a rule based on the density surface, for example, a rule that seeks to follow the steepest path between points. Lattice points that do not have a surrounding point that meet the rule are referred to as terminal lattice points, and are either associated with a new cluster or with a default background cluster. One or more methods can be used to split paths that converge on a false maximum.

According to some embodiments of the invention, at the end of the analysis, each lattice point will have associated with it one or more directional pointers in one or more paths, with the paths defining one or more meaningful clusters.

According to further embodiments, a lattice point either has one directed pointer emanating from it or not. The pointer from a first lattice point to a second lattice point represents an association between the first lattice point and the second lattice point. The lattice points may be scanned in any direction or manner to determine whether each of the particular lattice points possesses a pointer to any of the other neighboring lattice points. According to some embodiments, the determination of whether there is a pointer and to which lattice point the pointer points to is as follows and can be performed for every lattice point or for some subset of lattice points.

Example of Determining Existence of Direction of a Pointer

For a given lattice point, the value of the density estimate at that given lattice point may be compared to the value of the density estimate of all of the neighboring lattice points. If the former is smaller than the maximum of the latter, a pointer from the given lattice point is established to the neighboring lattice point where the maximum is attained. If the former is larger than the maximum of the later, then no pointer is created and that lattice point can be understood as representing a local maximum. After doing this analysis at each lattice point, the result is one or more pointer chains, each consisting of a sequence of pointers that consecutively connect a number of lattice points. Several chains may end in the same lattice point.

According to some embodiments of the invention, an example method can be described as choosing a lattice point and traversing the sequence of pointers emanating from that lattice point to a peak lattice point. If the density estimate of the last lattice point is above a certain threshold (such as the 65th percentile of all density estimates on the lattice), then this lattice point is labeled as the root of a cluster; if not, then all lattice points along the chain are labeled as background noise. Then the algorithm proceeds to the next chain. If the last lattice point of that chain was already traversed before, i.e. it is also a member of an earlier chain, then the chain is merged with the earlier chain, i.e. it points to the same root, or is assigned to background noise. Otherwise, this chain is dealt with as the first chain, resulting in a new root of a cluster or in an assignment to background noise. After the algorithm has dealt with all chains, each lattice point is assigned via a sequence of pointers to either a root of a cluster, or to background noise. Next, the algorithm determines whether some roots need to be merged.

Merging

If the distance of two roots is below a threshold (such as 3 lattice points), then the two roots will be merged by giving them the same identifier. Two roots will also be merged if there is a path of consecutive lattice points along which the values of the density estimates (described in the previous paragraph) do not fall more than a certain amount below the minimum values of the two roots. For instance the minimum chosen may be 5% of the square root of the minimum value of the two roots. After each pair of roots has been considered, the algorithm iterates the procedure on the new roots until no more changes are made.

Thus, each resulting root represents a cluster. The cluster membership of each data point can be determined as follows. First one may find the nearest lattice point and then follow the chain of pointers to a root, which represents the cluster, or to a label assigning it to background noise. A list is established, which notes for each lattice point the pertaining cluster number, or notes that it is background noise.

For each cluster, all pertaining data points can be retrieved as follows: Going through the above list delivers all lattice points pertaining to that cluster, and the data points pertaining to each lattice point can be accessed e.g. via a Voronoi diagram.

Assigning Observed Points to Lattice Points

With the lattice points each assigned to a cluster or to background noise, the observations are assigned to clusters by relating each observation to a lattice point and then using the cluster assignment of the lattice point. This is accomplished by an assignment rule. One assignment rule that can be used according to some embodiments of the invention is to assign each data point to the nearest (in Euclidean metric) lattice point, as described below.

Sequential Clustering

In a data set that has more than two dimensions, individual clusters can be subdivided according to values expressed in dimensions other than those used to define the cluster. Recursive application of this process can create a tree structure in which the nodes are subdivided by pairs (or greater numbers) of dimensions. At each subdivision, dimensions other than the set used to define the immediate parent can be used to define the child cluster. However, previous dimensions used prior to the penultimate pair can be reused.

Ranking of Dimensions

Information theory methods can be applied to clustered data to rank all possible dimension pairs within the data according their ability to subdivide the data. Two such methods are differential and Shannon entropy, which enable ranking of possible dimension pairs usable in a clustered dataset. In a sequential clustering application, this ranking can be used to inform the choice of the next axes to be used for clustering.

3. Example User Interface

Figure 2:
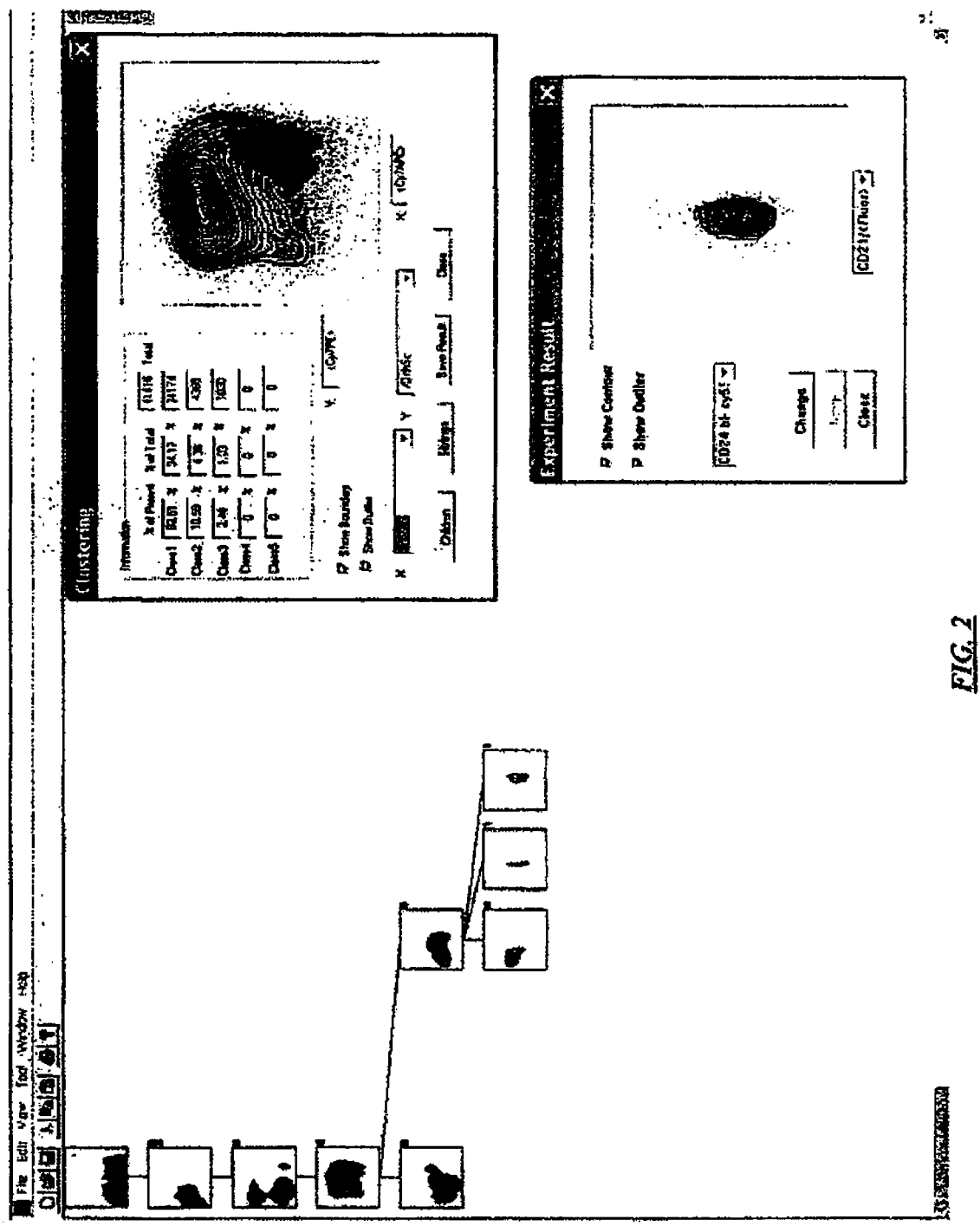
FIG. 2 illustrates an example user interface according to some embodiments of the invention.
Figure 3:
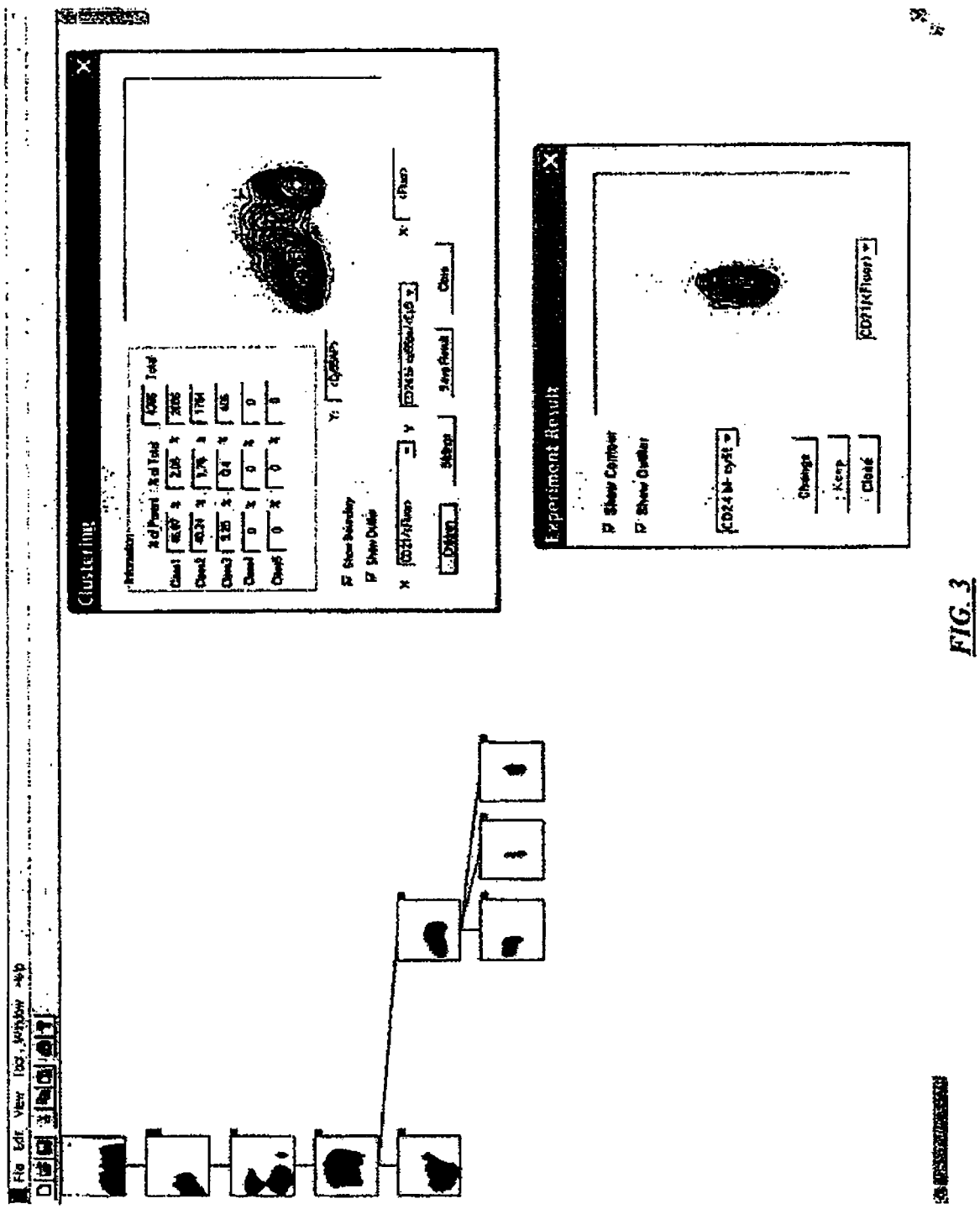
FIG. 3 illustrates an example user interface according to some embodiments of the invention.

The algorithm may be executed through a web-page and web-server. An exemplary display will appear as shown in FIG. 2 or FIG. 3. An alternative embodiment may be the use of the present algorithm with a command line interface instead of a GUI interface.

Figure 28:
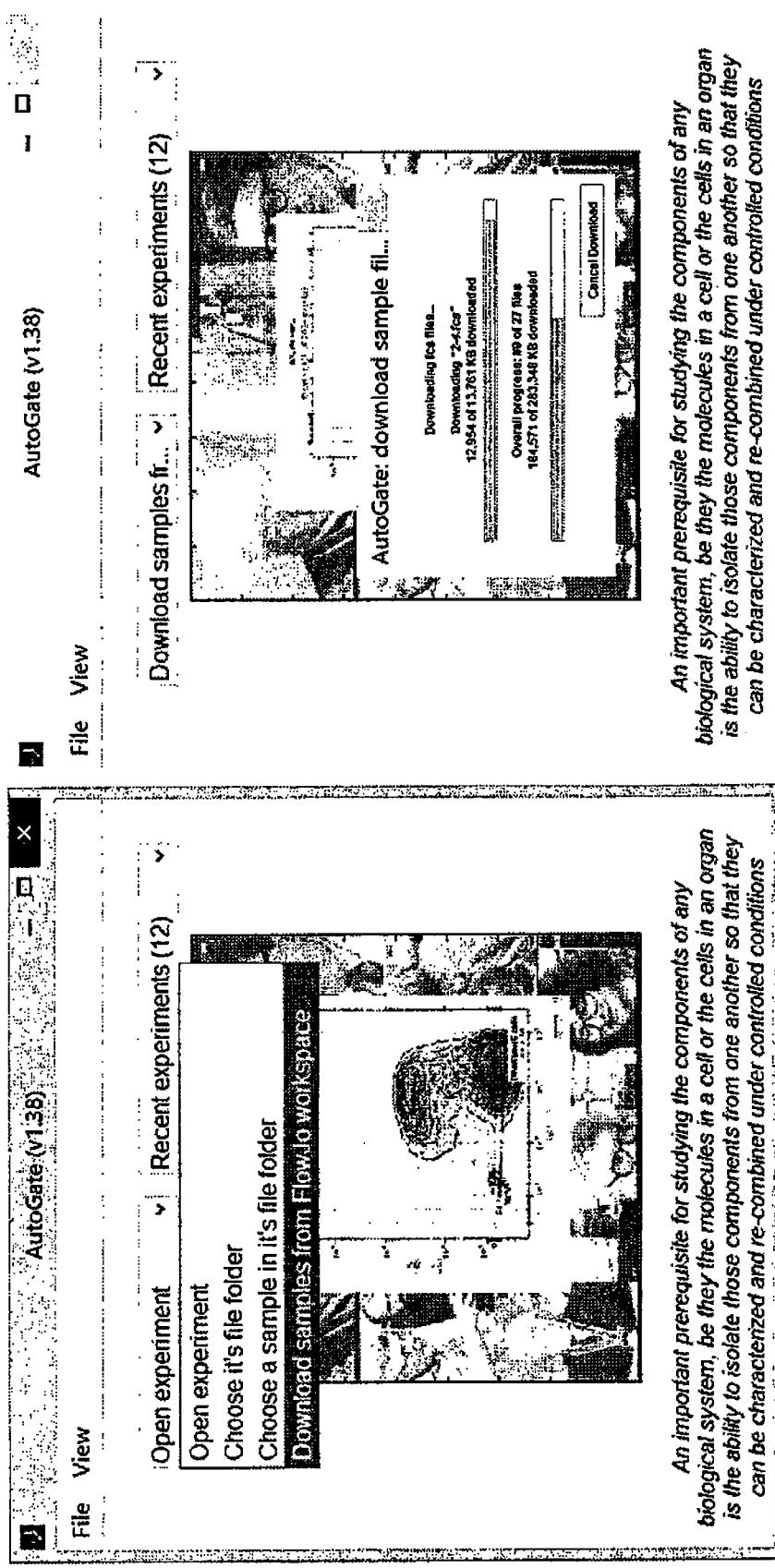
FIG. 28 shows screen shots for downloading samples from FlowJo workspace.
Figure 29:
FIG. 29 shows screen shot for configuring an experiment.
Figure 33:
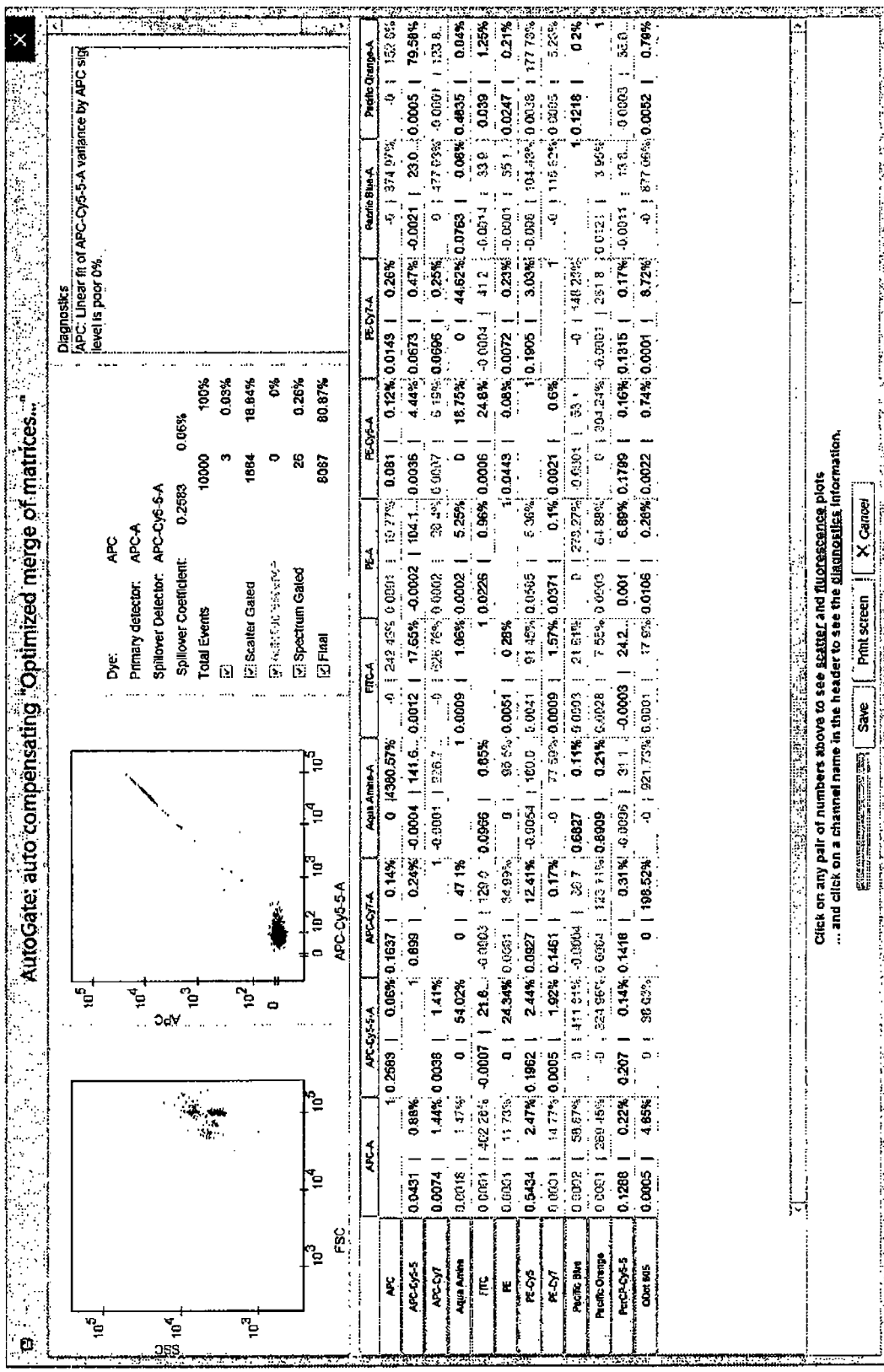
FIG. 33 shows a screen shot of flow cytometry data.
Figure 34:
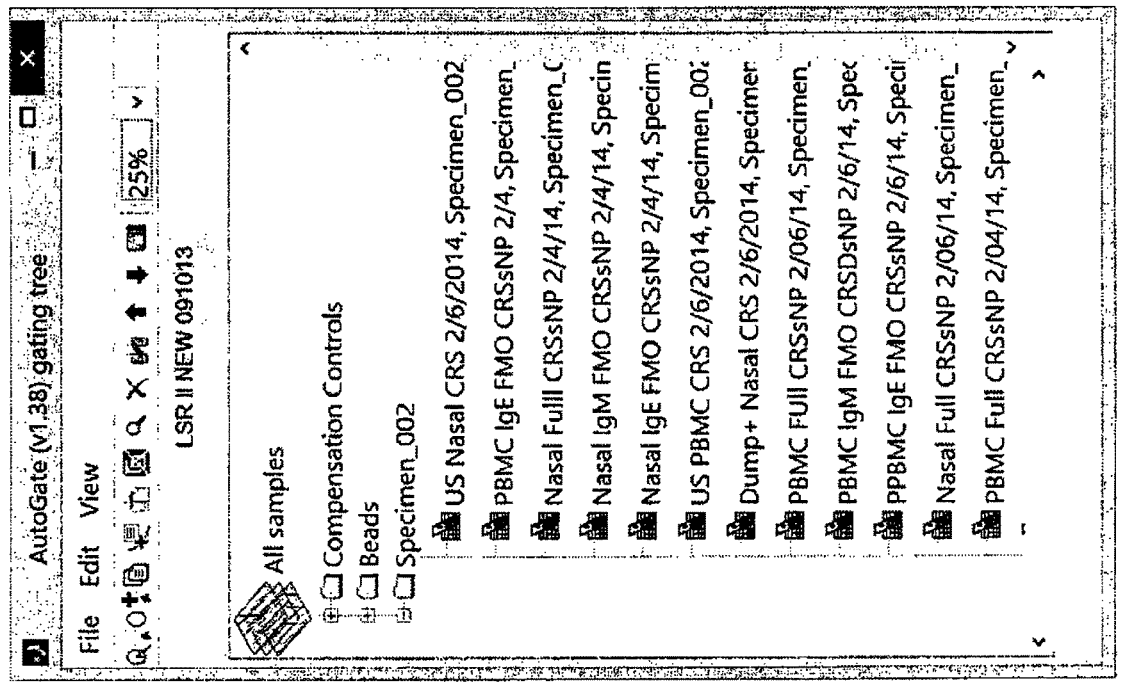
FIG. 34 shows a screen shot of a gating tree.
Figure 35:
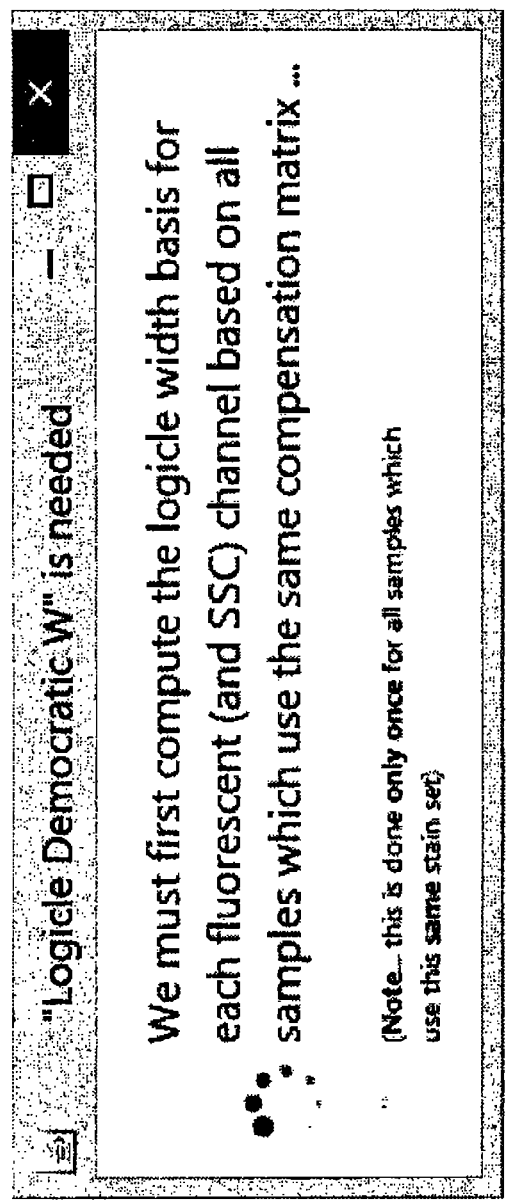
FIG. 35 shows a screen shot indicating that the logicle width basis for each fluorescent channel must be computed.
Figure 36:
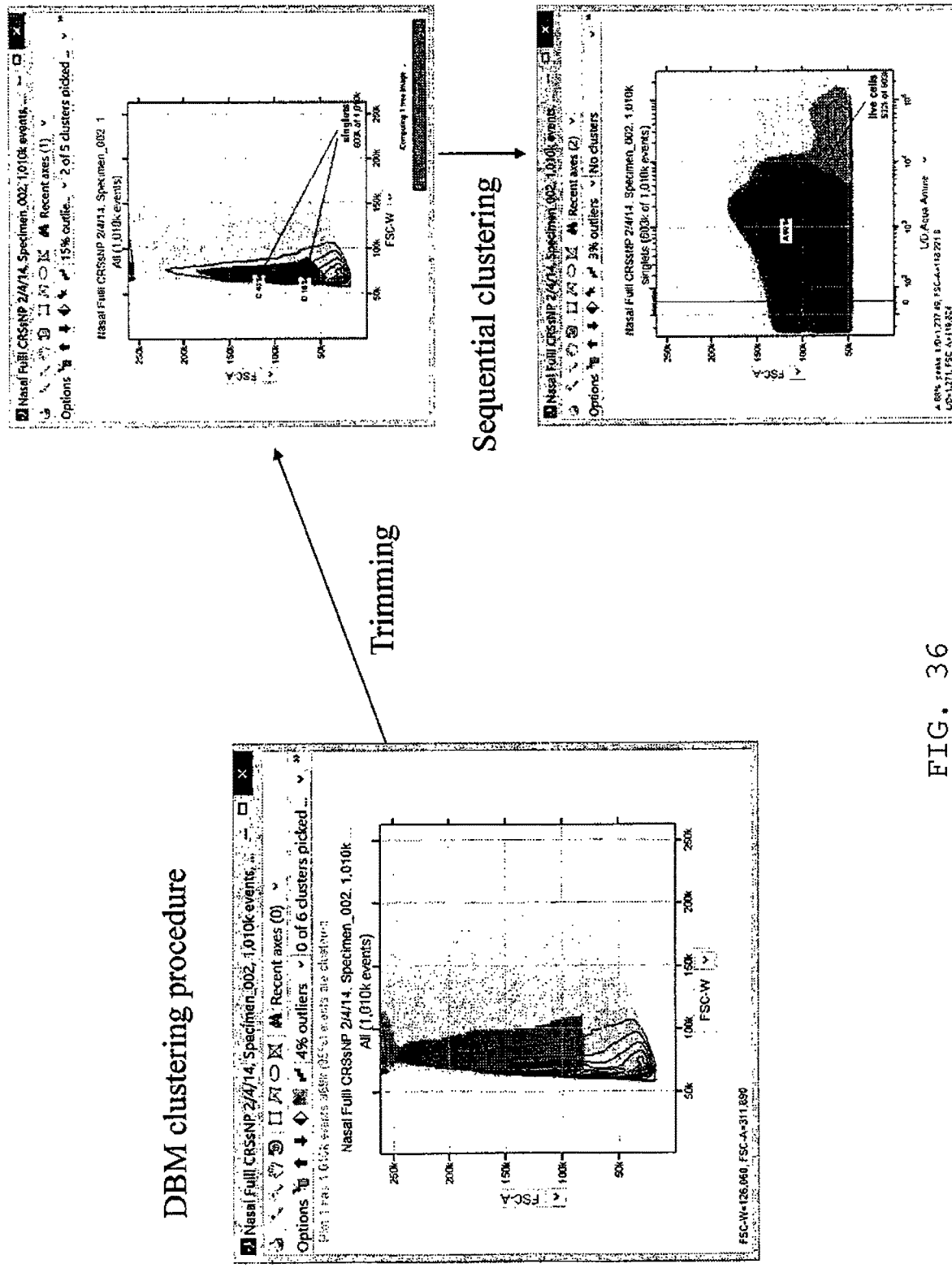
FIG. 36 shows screen shots for DBM clustering, trimming and sequential clustering.
Figure 37:
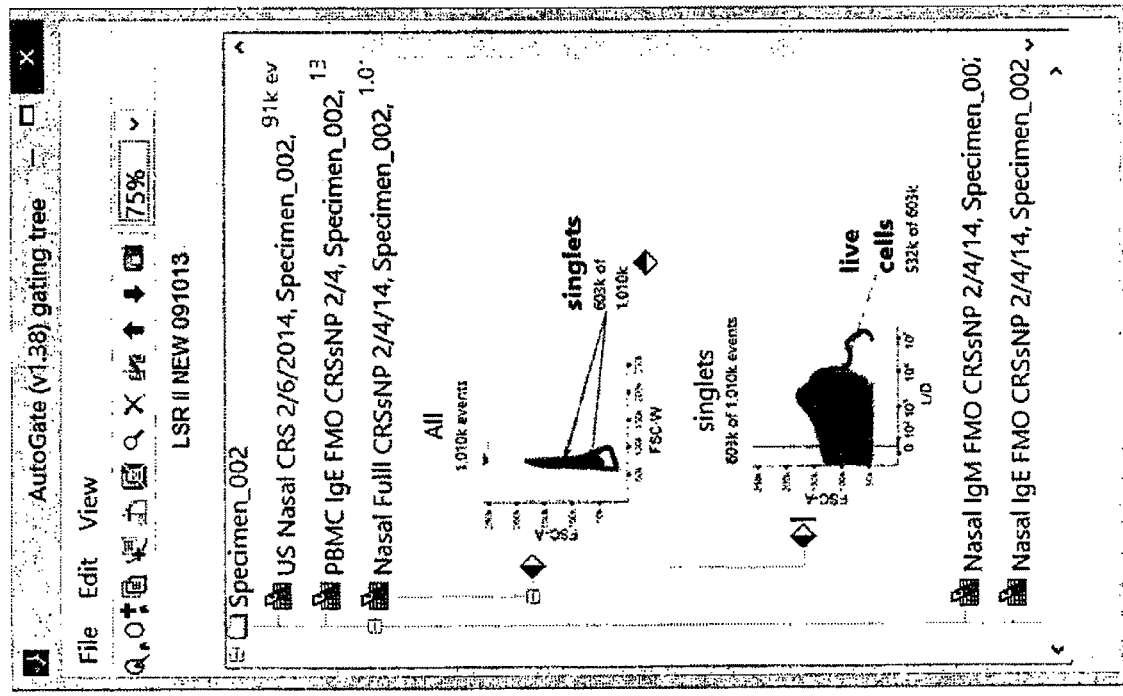
FIG. 37 shows a screen of a gating tree in the sequential clustering procedure.

The algorithm may be contained in an overall user interface that provides full processing capability for a specific application, such as flow cytometry. FIG. 28 et seq contain an example of such an interface subsumed under the name "AutoGate".

Example Execution Environment

According to one embodiment, the present invention is executed by a computer as software stored in a storage medium. The present invention may be executed as an application resident on the hard disk of a PC computer with an Intel Pentium or other microprocessor and displayed with a monitor. The processing device may also be a multiprocessor. The computer may be connected to a mouse or any other equivalent manipulation device. The computer may also be connected to a view screen or any other equivalent display device.

4. Example Detailed Description

The present invention can also be described using terms and mathematically notation that are generally familiar in the field of statistical analysis. It would be a straightforward endeavor using the description provided below to configure and/or program an information processing system to perform in accordance with this mathematically description.

Data Set

Consider a data set of n observations $x_1, \ldots, x_n$, where n can be very large, such as n » $10^6$ (for example for FACS analysis, for a large scale population, or for market analysis). Each observation $x_i$ has d dimensions, where each dimension can represent some observed or calculated or predicted parameter relative to observation and/or sample $x_i$. For example, in FACS, a number of dimensions may be a light intensity measured for a particular cell and/or group and/or sample of cells; in market analysis each dimension may be a measure of different characteristics and/or predictions and/or observations related to a market participant $x_i$. In some FACS applications, for example, d~10. Thus, in some embodiments, each $x_i$ can be understood to denote an ordered set of values, representing the dimensions 1 to d, e.g., $x_i = \{d_1, d_2, d_3 \ldots, d_d\}$. or, using notation that will allow individual dimensions to be indicated for specific observations $x_i = \{x_{i,1}, x_{i,2}, x_{i,3} \ldots, x_{i,d}\}$.

In some implementations, an implementation of the invention (e.g., a software implementation) according to some embodiments uses d=2 and can, for example examine 2-dimensional projections and/or two-dimensional samples of higher-dimensional data. A method according to some embodiments of the invention can further successively and/or selectively and/or interactively use various sets of 2 or more dimensions to perform clustering and can further select and/or combine results for different 2 or more dimensional analysis. The detailed interface example shows one example of an interactive two-dimensional analysis system allowing for successive analyses.

According to further embodiments of the invention, in selecting a cluster for further analysis, the invention may use extrinsic information either to enhance an interactive selecting or to perform an automatic selection of a cluster for further analysis. This intrinsic information can include information in a database, knowledge base or any other externally supplied information.

Furthermore, in the present discussion, assume that one or more dimensions/coordinates of observations x; are continuous for some given decimal precision.

For example, for FACS data, each observation $x_i$ could represent one cell and/or sample measured and each parameter and/or coordinate and/or dimensional value represents a measured characteristic of the cell. According to some such embodiments, one or more parameters of an observed cell $x_i$ will represent a florescence color detected for a cell. As a further example, for marketing data, each observation $x_i$ can represent a market participant with each coordinate representing a certain characteristic and/or prediction and/or observation of the market participant such as income, confidence, buying characteristics, market power, etc.

The Cluster Model

According to some embodiments of the invention, it is assumed that the observations $x_1, \ldots, x_n$ are drawn from (or generated by) a density $$f(x) = \sum_{k=1}^{K} a_K g_K(x), \; a_K > 0, \sum_K a_K = 1. \tag{1}$$

where $g_k$ represent one of a number of clusters/components 1 through K and $a_k$ represents a percentage coefficient value that each cluster contributes to the total set of observed data. Thus, k represents a cluster index. In the art, it is sometimes said that the densities $g_k(x)$ are the component densities that represent the populations (or clusters).

Furthermore, according to some embodiments of the invention from experience in the case of example FACS data, assume for the component densities $g_k$ that all level sets $L(t)=\{x \in R^d : g_K(x) \geq t\}$, $t \geq 0$, are path connected, that is for every $t \geq 0$ and every $x, y \in L(t)$ there exists a continuous function $p:[0,1] \rightarrow R^d$ such that $p(0)=x, p(1)=y$ and $p(u) \in L(t)$ for all $u \in [0,1]$.

Thus, according to the example model shown in Eq. (1), each observation $x_i$ arises from one of the components/clusters $g_k$, $k=1, \ldots, K$, where $g_1$ is a cluster that is understood or assigned to model 'background noise' (e.g., $g_1$ is understood as the source of all observations $x_i$ that are not related to, or grouped by any of the clusters $g_2, \ldots, g_k$).

An aspect of an example clustering procedure is to determine, based on $x_1, \ldots, x_n$, a value for K (e.g., how many components/clusters there are) and to determine a rule that assigns each observation $x_i$ and or each region of the relevant data space (to provide assignment for future observations not yet available) to one of the components/clusters $g_k$.

Example Data Reduction

Example Lattice/Grid Use

According to one embodiment, $x_i$ can represent very large sets of data, include sets where the number of observations $x_i$ are much greater than $10^6$. Thus, to reduce the data set both to allow for easier computation and to provide other inferences, a data reduction technique using a lattice is used as described in detail below.

According to some embodiments of the invention, a lattice L is constructed and/or assumed and/or defined in $R^d$ space consisting of $M^d$ points, where M is generally a positive integer; for example for FACS applications M can be, for example, 64 or 128. Such a lattice can be understood as simply a regular and normalized lattice in d dimensions where the normalization is set to take account of all or some subset of the observed data. Stated more formally, set $\Delta_j = \max_i x_{i,j} - \min_i x_{i,j}/(M-1)$, $j=1, \ldots$, in other words, the size of a d-dimensional unit area or volume is set to be $\Delta_j$. Define the jth coordinate of lattice points $y_{(m1, \ldots, md)}$ to be $y_{mj} = \min_i x_{i,j} + (m_j-1) \Delta_j$, $m_j=1, \ldots, M$. Then the lattice L is defined as $L=\{y_{(m_1, \ldots, m_d)}:(m_1, \ldots, m_d) \in \{1, \ldots, M\}^d\}$.

Example Weighting Assignment

Next, each lattice point $y_m$ is assigned a weight $w_m$ that, for example, is derived in part from one or more of the observed data points $x_i$ in the data space. One exemplary weight assignment according to some embodiments of the present invention is to use a linear binning technique such as:

$$w_m = \sum_{i=1}^{n} \prod_{j=1}^{d} \max(0, 1 - |x_{i,j} - y_{mj}|/\Delta_j).$$

While this particular example formally uses all of the observations $x_i$ in calculating each weighting faction, in fact very distant points usually are not included in the weight for a particular $y_m$. Various other weighting functions, including functions that eliminate outlying points, etc., can be used to assign weights according to some embodiments of the invention. Examples of such methods that can be employed according to some embodiments of the invention are as described in Fan, Jianqing and Marron, James S. "Fast implementations of nonparametric curve estimators". Journal of Computational and Graphical Statistics. 1994, Vol. 3, 35-56, which is incorporated herein by reference.

Computing the Density Estimate

According to some embodiments of the invention, at each lattice point $y_m$ a calculation is performed allowing the contours of the $y_m$ lattice points based on weights to be analyzed. One method for doing this is to compute an estimate of a density surface $\hat{f}(y_m)$. According to some embodiments of the invention, this can be performed as follows. The Gaussian kernel is denoted by $\phi(b)=1/\sqrt{2\pi} \exp(-b^2/2)$. Then the estimated density at $y_m$ can be computed by:

$$\hat{f}(y_m) = 1/n \sum_{l_1=-Z_1}^{Z_1} \ldots \sum_{l_d=-Z_d}^{Z_d} \omega_{m-1} \prod_{j=1}^{d} \phi(l_j \Delta_j/h_j)/h_j,$$

where $l=(l_1, \ldots, l_d), Z_j = \min(\lfloor 4h_j/\Delta_j \rfloor, M-1)$, and
$h_j = SD(\{x_{i,j}, i=1, \ldots, n\}) n^{-1/(d+4)})$ where SD denotes standard deviation. The sum as indicated in the above formula can be computed quickly with the Fast Fourier Transform (FFT) in a well-known way, for example as discussed in Wand (1994). It can also be computed directly using the above formula without the FFT. Note that while this expression has been written for clarity in terms of the observations $x_{ij}$, it could equivalently be written in terms of $y_m$ and the weights.

Clustering by Associating Pointers Between Lattice Points

According to some embodiments of the invention, clusters are determined in the lattice space defined by lattice points $y_m$ using a correlation between the lattice points, such as the density surface. In order to make associations between the lattice points, considering each lattice point $y_m$ in turn, according to specific embodiments, the invention computes $$\hat{\sigma}_m^2 = \frac{1}{n(n-1)} \sum_{l_1=-Z_1}^{Z_1} \cdots \sum_{l_d=-Z_d}^{Z_d} w_{m-1} \prod_{j=1}^{d} \phi^2(l_j \Delta_j / h_j) / h_j^2 - \frac{1}{n-1} \hat{f}(y_m)^2,$$

which can be generally understood as an estimate of the standard deviation of the density estimate. The sum can be computed with the FFT as above. The index set is defined:

$$S = \{m \in \{1, \ldots M\}^d : \hat{f}(y_m) > 4.3 * \sqrt{\hat{\sigma}_m^2}\}.$$

According to some embodiments of the invention, association pointers are used to determine clusters. These pointers can be understood as pointing from a lattice point to a neighboring lattice point. In some embodiments, these pointers are established or removed by successively executing a series of evaluations, such as described in steps 1-6 below.

Step 1

For all lattice points $y_m$ where $m \in S_1'$, in turn:

Consider all the neighboring lattice points $p_1, \ldots, p_{nm}$ which are defined as the set of all lattice points contained in a d-dimensional rectangular volume. Let $p \in \{p_1, \ldots, p_{n\,m}\}$ such that $\hat{f}(p) = \max_{k=1, \ldots, nm} \hat{f}(p_k)$, splitting ties in an arbitrary manner. Then step 1 establishes an association pointer from $y_m$ top provided the following two conditions hold:

$$\hat{f}(p) > \hat{f}(y_m); \text{ and}$$

$$\frac{\partial}{\partial e} \hat{f}(y_m) > \lambda_m,$$

where $e = (p - y_m)/\|p - y_m\|$, $\|\cdot\|$ denotes Euclidean norm, and $$\frac{\partial}{\partial e} \hat{f}(y_m) = \sum_{a=1}^{d} e \frac{\partial}{\partial y_{m_a}} \hat{f}(y_m),$$

which indicates a gradient of the density estimate, $$\frac{\partial}{\partial y_{m_a}} \hat{f}(y_m) = 1/n \sum_{l_1=-Z_1}^{Z_1} \cdots \sum_{l_d=-Z_d}^{Z_d} w_{m-1} \frac{-l_a \Delta_a}{h_a^2} \prod_{j=1}^{d} \phi(l_j \Delta_j / h_j) / h_j$$

$$\lambda_m = q(0.95^{1/\kappa}) \sqrt{\hat{\Sigma}_m^2}$$

$$\kappa = \frac{\# S \Sigma_{m \in S} w_m}{n(2\pi)^{d/2} \prod_{j=1}^{d} h_j \Sigma_{m \in S} w_m \hat{f}(y_m)}$$

$$\hat{\Sigma}_m^2 = \frac{1}{n-1} \left( \sum_{a,b=1}^{d} e_a e_b \left[ A - \frac{\partial}{\partial y_{m_a}} \hat{f}(y_m) \frac{\partial}{\partial y_{m_b}} \hat{f}(y_m) \right] \right)$$

-continued $$A = \frac{1}{n} \sum_{l_1=-Z_1}^{Z_1} \cdots \sum_{l_d=-Z_d}^{Z_d} w_{m-1} \frac{l_a l_b \Delta_a \Delta_b}{h_a^2 h_b^2} \prod_{\varphi=1}^{\delta} \phi^2(l_j \Delta_j / h_j) / h_j^2$$

(A is an estimate of $$\frac{\partial}{\partial y_{m_a}} f(y_m) \frac{\partial}{\partial y_{m_b}} f(y_m).$$

q(x) denotes the 100xth percentile of the standard normal distribution. All the sums can be computed with the FFT as above.

Step 2

From each lattice point $y_m$, $m \notin S$; a pointer is established that points to a state representing the background noise.

Step 3

For all lattice points $y_m$, $m \notin S$, in turn:

If a pointer originates at $y_m$ then it will point to a different lattice point, which itself may have a pointer originating from it. A succession of pointers is followed until one arrives at a lattice point $y_z$ is reached that either (a) does not have any pointer originating from it, or (b) has a pointer originating from it that points to a state representing a cluster or background noise.

In case (a), all the pointers visited in the succession will be removed and new pointers originating from each lattice point visited in the succession will be established to the background noise state, provided that: $\hat{f}(y_z) < q(0.95^{1/\kappa}) \sqrt{\hat{\sigma}_z^2}$. Otherwise, only the pointer originating from $y_z$ (if any) will be removed, and a new pointer will be established that originates from $y_z$ and points to a newly cluster state. In case (b) above, no pointers are removed or established.

Step 4

Let $\{y_{m(1)}, \ldots y_{m(k)}\}$ be the set of all lattice points which have a pointer originating from them to a dummy state representing a cluster, enumerated such that $$\hat{f}(y_{m(1)}) \geq \ldots \geq \hat{f}(y_{m(k)}), \text{ and for } i = 1 \ldots k \text{ do:}$$

Set $A = \{m(i)\}$. Iterate the following loop until no more indices are added to A: (Begin loop)

For each index $a \in A$ in turn, add all the indices p to A that satisfy:

$y_p$ is a neighbor or $y_a$ as defined in step 1, and no pointer originates from $y_p$, and $$\hat{f}(y_p) + \hat{\sigma}_p \geq \hat{f}(y_{m(i)}) + \hat{\sigma}_{m(i)}$$

(End loop)

Denote by B the set of indices of lattice points from which a pointer originates to a cluster state and that also have some $y_{p'}$ p E as neighbor. If B is not empty, then do the following:

Define q by $\hat{f}(y_q) = \max_{r \in B} \hat{f}(y_r)$, breaking ties arbitrarily. Establish a pointer from each $y_p$, $p \in A \setminus \{m(i)\}$, to $y_q$ For each r∈B, r≠q: remove the pointer from $y_r$ to the state representing a cluster, and establish a new pointer from $y_r$ to $y_q$.
(End loop over i)

Step 5

Repeat step 4 until there are no more additions or deletions of pointers to cluster state.

Step 6

From each lattice point that does not have pointer originating from it, establish a pointer pointing to the background noise state.

Lattice Point Results

With the above described procedure, according to some embodiments of the invention, every lattice point has a pointer originating from it. Following the succession of pointers leads to a state outside of the lattice point space which either represents a background noise or a cluster. All lattice points that are linked pertain to the same cluster or to background noise.

Assigning Observed Points to Lattice Points

With the lattice points each assigned to a cluster or to background noise, observations $x_i$ are assigned to clusters by relating each observation to a lattice point and then using the cluster assignment of the lattice point. This is accomplished by an assignment rule. In some embodiments, each observation $x_i$ is assigned to the lattice point $y_m$ that is closest to $x_i$ in Euclidean norm. Then $x_i$ is assigned to the same cluster to which its associated lattice point ym is assigned. Likewise, all observations assigned to a certain cluster can be found as follows: Find all lattice points $y_m$ that the algorithm assigns to the given cluster, then find all observations $x_i$ that are assigned to these lattice points.

Dimension Pair Ranking

According to some embodiments of the invention, two variations of the entropy theory (differential and Shannon entropy) can be implemented together with the above described procedure in order to estimate scores for dimension pair ranking. As described below, the entropy scores of each of the dimension pairs (X and Y parameters) can be estimated during DBM algorithm realization over data sets.

Differential Entropy

For each dimension pair, a standard negative differential entropy Q(f) is computed; then the dimension pairs are ranked according to the value of Q(f), which serves as scoring metric. An approximation to standard negative differential entropy is computed by summing over the lattice/grid points together with their weights:

$$Q(f) = \sum_m \ln(f(y_m))w_m + \frac{1}{2}\ln(\det(\sum))$$

Where Σ is the covariance matrix of cell density $f(y_m)$. The general idea for standard negative differential entropy is that a normal distribution (Q(f)=0) is "uninteresting" because it represents one nice cluster. Dimension pairs where $f(y_m)$ far from normal, i.e. Q(f) is large, are more informative.

Shannon Entropy

Shannon entropy score $H(P_i)$ for each possible dimension pair is computed by summing over weights associated with each lattice/grid point: for clusters $C_i=1, \ldots, n$ $$H(P_i) = -\sum_i P_i \log_2 P_i$$

$$P_i = \sum_{j \in C_i=} w_j$$

Where $w_j$ is a matrix of associated weights. The idea behind the Shannon entropy score is that it is minimized by the uniform distribution, not by the normal distribution as in the case of a standard negative differential entropy score. Dimension pairs where $w_m$ far from uniform, i.e. $H(P_i)$ is large, are more informative.

5. Example Interface

FIG. 2 illustrates an example user interface according to some embodiments of the invention. FIG. 3 illustrates an example user interface according to some embodiments of the invention. From the left is illustrated a tree that shows parent-children relationships of clustering results.

In the upper right window is illustrated detailed information regarding three identified clusters (Class1, Class2, and Class3) at a particular iteration of the cluster selection. The details shown in this example, interface include, for each cluster/class, the % of the selected parent cluster that is in this identified cluster (e.g., 82.51 for Class1), the % of the total population that is in this identified cluster (e.g., 34.17 for Class1), and the total number of observations in that class (e.g., 34174). In this example, the total number of observations being analyzed in these displayed clusters is as indicated in the figure. (e.g., 41416).

According to some embodiments of the invention, an interface such as that shown can also include labels indicating X and Y parameters, option inputs to show boundaries and/or contours and/or outliers, and inputs to save results.

From this window, clustering of other regions can be performed by selecting children to indicate a sub region or selecting siblings to indicate a different clustering to be performed from the parent and further inputting the desired clustering parameters using the drop down X and Y inputs shown. FIG. 3, for example, shows a three children clusters identified from class 2 of FIG. 1.

According to some embodiments of the invention, the right-bottom window is a window to allow a user to try different clustering parameters. The results in this window are not kept until a user chooses to do this by clicking the "keep" button.

Thus, according to some embodiments of the invention, the invention automatically finds clusterings for a user that they otherwise must find manually. The interface provides a clear and hierarchical display to indicate the clusterings results.

6. Embodiment in a Programmed Information Appliance

Figure 4:
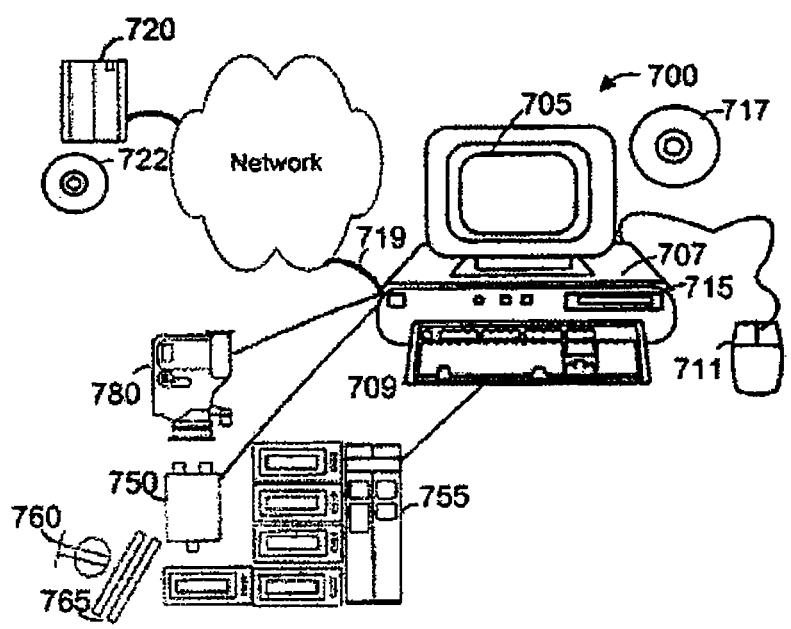
FIG. 4 is a block diagram showing a representative example logic device in which various aspects of the present invention may be embodied.

FIG. 4 is a block diagram showing a representative example logic device in which various aspects of the present invention may be embodied. As will be understood from the teachings provided herein, the invention can be implemented in hardware and/or software. In some embodiments, different aspects of the invention can be implemented in either client-side logic or server-side logic. Moreover, the invention or components thereof may be embodied in a fixed media program component containing logic instructions and/or data that when loaded into an appropriately configured computing device cause that device to perform according to the invention. A fixed media containing logic instructions may be delivered to a viewer on a fixed media for physically loading into a viewer's computer or a fixed media containing logic instructions may reside on a remote server that a viewer accesses through a communication medium in order to download a program component.

FIG. 4 shows an information appliance or digital device 700 that may be understood as a logical apparatus that can perform logical operations regarding image display and/or analysis as described herein. Such a device can be embodied as a general purpose computer system or workstation running logical instructions to perform according to some embodiments of the present invention. Such a device can also be custom and/or specialized laboratory or scientific hardware that integrates logic processing into a machine for performing various sample handling operations. In general, the logic processing components of a device according to some embodiments of the present invention is able to read instructions from media 717 and/or network port 719, which can optionally be connected to server 720 having fixed media 722. Apparatus 700 can thereafter use those instructions to direct actions or perform analysis as understood in the art and described herein. One type of logical apparatus that may embody the invention is a computer system as illustrated in 700, containing CPU 707, optional input devices 709 and 711, storage media (such as disk drives) 715 and optional monitor 705. Fixed media 717, or fixed media 722 over port 719, may be used to program such a system and may represent a disk-type optical or magnetic media, magnetic tape, solid state dynamic or static memory, etc. The invention may also be embodied in whole or in part as software recorded on this fixed media. Communication port 719 may also be used to initially receive instructions that are used to program such a system and may represent any type of communication connection.

FIG. 4 shows additional components that can be part of a diagnostic system in some embodiments. These components include a microscope or viewer or detector 750, sampling handling 755, light source 760 and filters 765, and a CCD camera or capture device 780 for capturing digital images for analysis as described herein for luminance detection. It will be understood to those of skill in the art that these additional components can be components of a single system that includes logic analysis and/or control. These devices also may be essentially stand-alone devices that are in digital communication with an information appliance such as 700 via a network, bus, wireless communication, etc., as will be understood in the art. It will be understood that components of such a system can have any convenient physical configuration and/or appear and can all be combined into a single integrated system. Thus, the individual components shown in FIG. 4 represent just one example system.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

7. Other Embodiments

Other embodiments will be apparent to those of skill in the art. In particular, a viewer digital information appliance has generally been illustrated as a personal computer. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to some embodiments of the present invention. For example, a voice command may be spoken by an operator, a key may be depressed by an operator, a button on a client-side scientific device may be depressed by an operator, or selection using any pointing device may be effected by the user.

Logic systems and methods such as described herein can include a variety of different components and different functions in a modular fashion. Different embodiments of the invention can include different mixtures of elements and functions and may group various functions as parts of various elements. For purposes of clarity, the invention is described in terms of systems and/or methods that include many different innovative components and innovative combinations of innovative components and known components.

No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Java-script, HTML, XML, dHTML, assembly or machine code programming, etc. and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and sub goals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Variations on Clustering Methodology

The above-described density based merging approach to clustering assigns data (measured from individuals, e.g., cells) that occurs on regions with a density below a given threshold to the background. Assigning data to the background adjudges those data points to be irrelevant to any cluster and therefore does not plot them in a graphical display or categorize them in a cluster set. The counting/plotting or discounting/not plotting of data points impacts the visual display of the clusters and determines the shape of the resultant observable clusters. It may be known in a given field, e.g., cell biology, that the threshold of density that provides the most insightful cluster patterns differs depending on the parameters selected (for the x and y axis of a given 2D plot). In accordance with one aspect of the present disclosure, the density threshold may be adjustable to widen or narrow the boundaries of the clusters.

Referring to the above-described mathematical description of the density based clustering methodology, in defining the index set $$S = \{m \in \{1, \ldots, M\}^d : \hat{f}(y_m) > 4.3 * \sqrt{\hat{\sigma}_m^2}\},$$

the constant 4.3 can be adjusted to set the density threshold in order to change the boundaries of the clusters. This constant may be referred to as $q(\alpha)$, where a fraction $\alpha$ of the data points associated with individuals of a population, e.g., cells in a sample, are below the threshold and are therefore excluded from index set S. In one approach, instead of computing $q(\alpha)$, the set S is built by adding data points in order of descending density values $\hat{f}(Y_m)$ until the fraction of individuals (cells) in S exceeds $(1-\alpha)$. The fraction of individuals (cells) pertaining to grid point M is given by $W_M$ in equation $$w_m = \sum_{i=1}^{n} \prod_{j=1}^{d} \max(0, 1 - |x_{i,j} - y_{mj}|/\Delta_j).$$

Since $W_M$ may not sum exactly to 1, it is better to refer to $\tilde{W}_M = W_{M/\Sigma Wi}$; $i \in \{1, \ldots, M\}^2$ As a further alternative, the condition $$\frac{\partial}{\partial e}\hat{f}(y_m) > \lambda_m,$$

where $e = (p - y_m)/\|p - y_m\|, \|\cdot\|$ may be eliminated in establishing an association pointer from $y_m$ to p. Furthermore, the quantities $$\frac{\partial}{\partial y_{m_a}} \hat{f}(y_m) = 1/n \sum_{l_1=-Z_1}^{Z_1} \cdots \sum_{l_d=-Z_d}^{Z_d} w_{m-1} \frac{-l_a \Delta_a}{h_a^2} \prod_{j=1}^{d} \phi(l_j \Delta_j / h_j)/h_j$$

$$\lambda_m = q(0.95^{1/\kappa})\sqrt{\hat{\Sigma}_m^2}$$

$$\kappa = \frac{\# S \Sigma_{m \in S} w_m}{n(2\pi)^{d/2} \prod_{j=1}^{d} h_j \Sigma_{m \in S} w_m \hat{f}(y_m)}$$

$$\hat{\Sigma}_m^2 = \frac{1}{n-1}\left(\sum_{a,b=1}^{d} e_a e_b \left[A - \frac{\partial}{\partial y_{m_a}}\hat{f}(y_m)\frac{\partial}{\partial y_{m_b}}\hat{f}(y_m)\right]\right)$$

$$A = \frac{1}{n}\sum_{l_1=-Z_1}^{Z_1} \cdots \sum_{l_d=-Z_d}^{Z_d} w_{m-1}\frac{l_a l_b \Delta_a \Delta_b}{h_a^2 h_b^2}\prod_{\varphi=1}^{\delta} \phi^2(l_j\Delta_j/h_j)/h_j^2$$

do not need to be computed

Trimming

Figure 5:
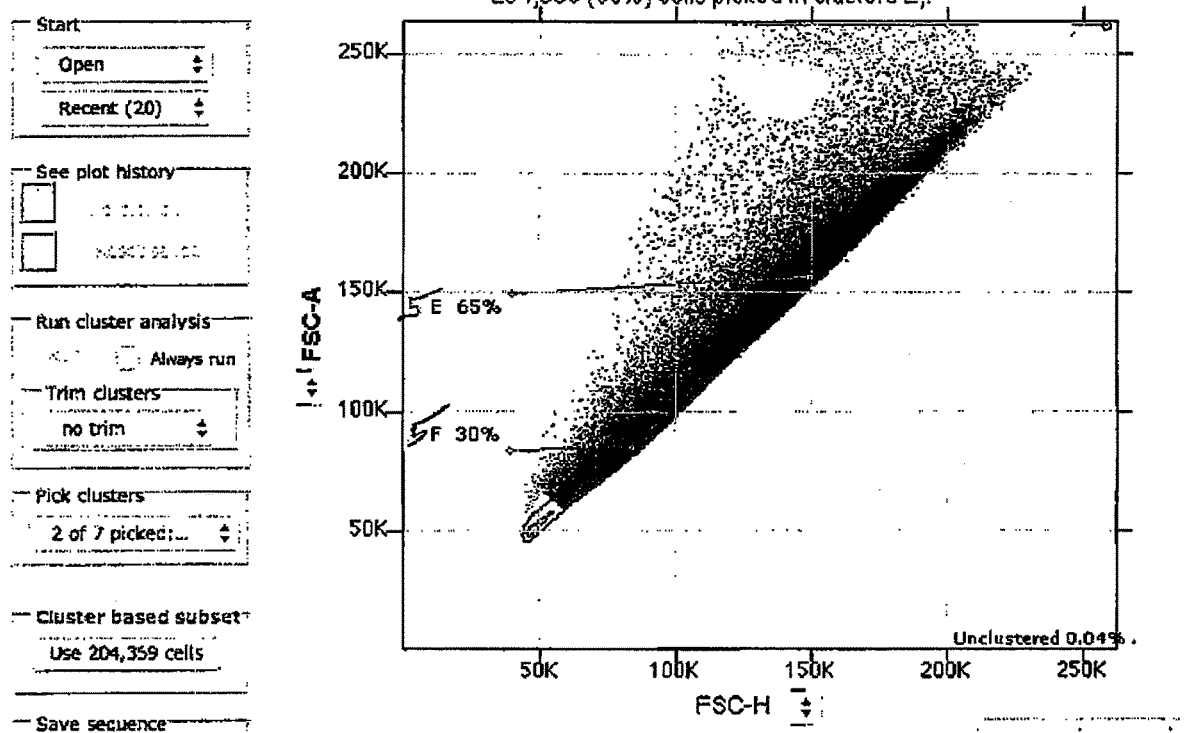
FIGS. 5-8 are screen shots graphically depicting clusters with varying percentages of trim.
Figure 6:
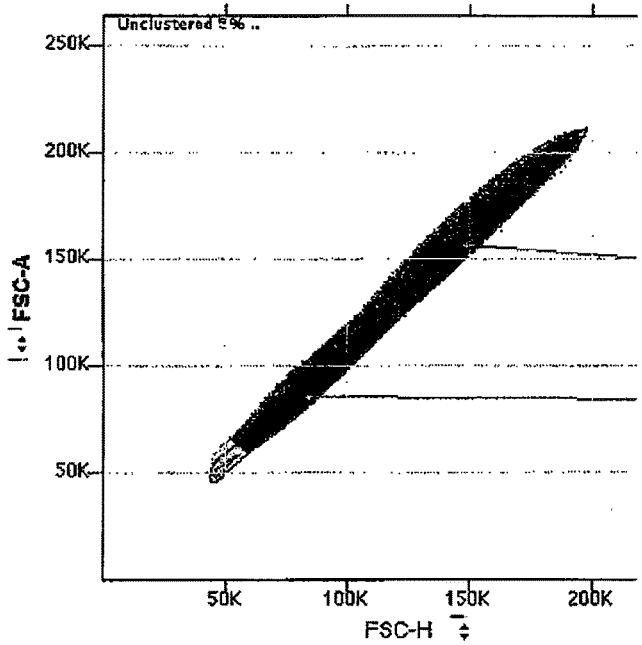
Figure 7:
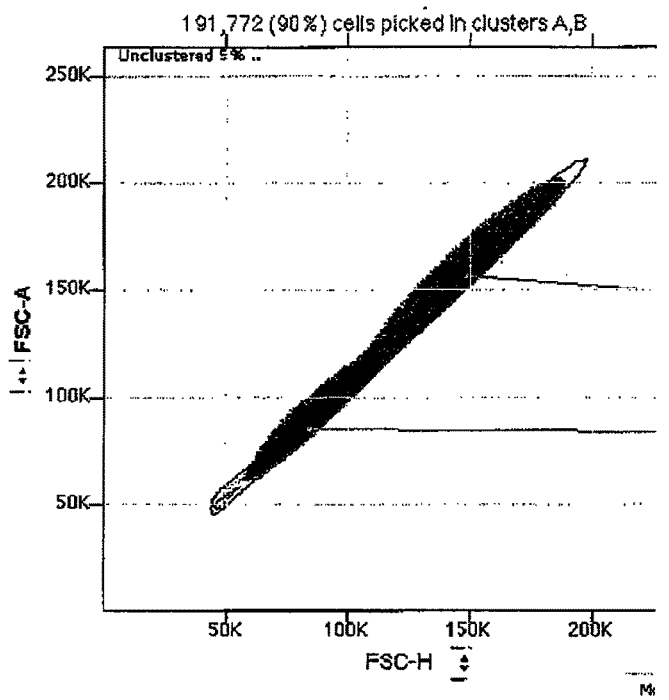
Figure 8:
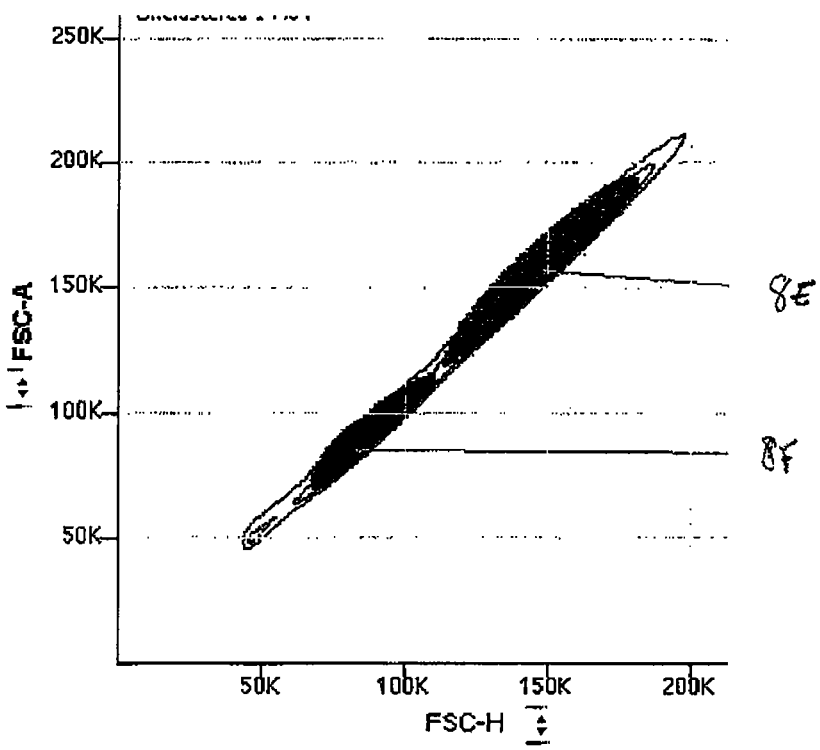

FIG. 5 shows a 2D plot of data FSC-H vs. FSC-A readings obtained by testing a cell sample (population) having 211, 500 cells using a flow cytometer. The plot shows two clusters 5E and 5F that have been discerned by the DBM method described above. The clusters 5E, 5F may be attributable to the existence of at least two types of cells present in the population that are distinguishable with respect to the combination of FSC-H and FSC-A readings achieved when illuminated by a laser at 0 and 90 degrees orientation, respectively. An option box presented on the screen permits the operator to set the amount of "Trim," which corresponds to setting the constant $q(\alpha)$, as described above. In FIG. 5, the selected setting "No Trim", which corresponds to a $q(\alpha)$ of 4.3. This generates the results shown. Namely, cluster 5E includes 65% of the cells and cluster 5F includes 30% of the cells. In FIGS. 6, 7, and 8, increasing degrees of trim, viz., 5%, 9% and 15%, respectively, are utilized in the DBM process, generating the results shown. The percentages of cells in all defined clusters, plus absolute numbers of cells in the cluster and other relevant statistics are shown for each node in the tree in the user interface(s).

Trimming can be utilized to tailor the inclusiveness of a cluster in response to observed cluster patterns and known marker expression patterns. In the instance where a cluster is over-inclusive, trimming can be used to eliminate members of the population that can be observed to be or are thought not to belong to a cluster to which they have been assigned. Trimming, which is readily reversible in the interface, is a way of setting cluster boundaries. If the margins are narrowed, the cluster becomes less inclusive and if broadened, the cluster becomes more inclusive. Adjustments to cluster boundaries may be made in pursuit of meaningful clusters. When rare cells are to be visualized, trimming often needs to be decreased (see "Cluster Boundary Expansion" below). In the area of cell analysis, e.g., meaningful clusters are representations of cells expressing markers defined by the analysis the user is doing. The expansion or retraction of cluster borders (trimming) may be used to make a given cluster more or less inclusive without any alteration (loss or gain) of the original data set.

Cluster Boundary Expansion

Figure 9:
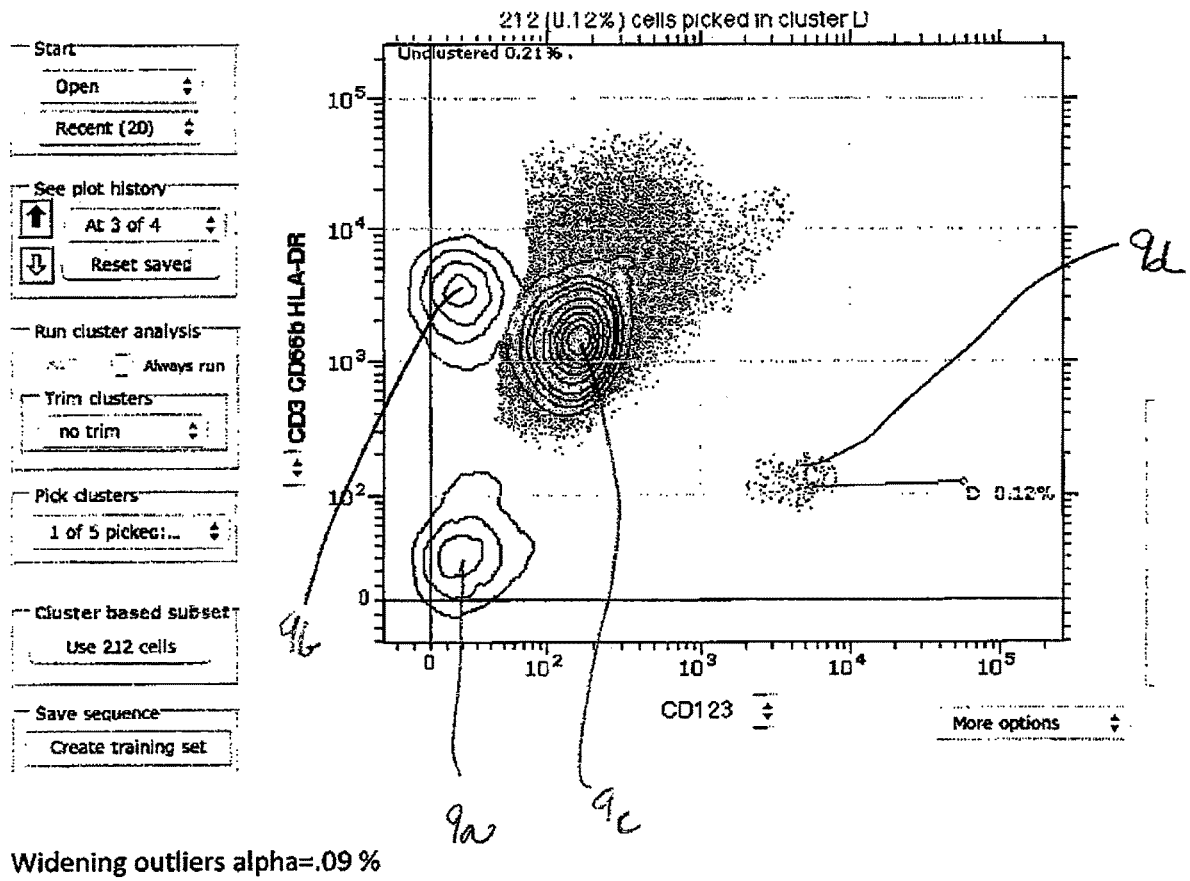
FIGS. 9-12 are screen shots depicting varying percentages of cluster boundary expansion.
Figure 10:
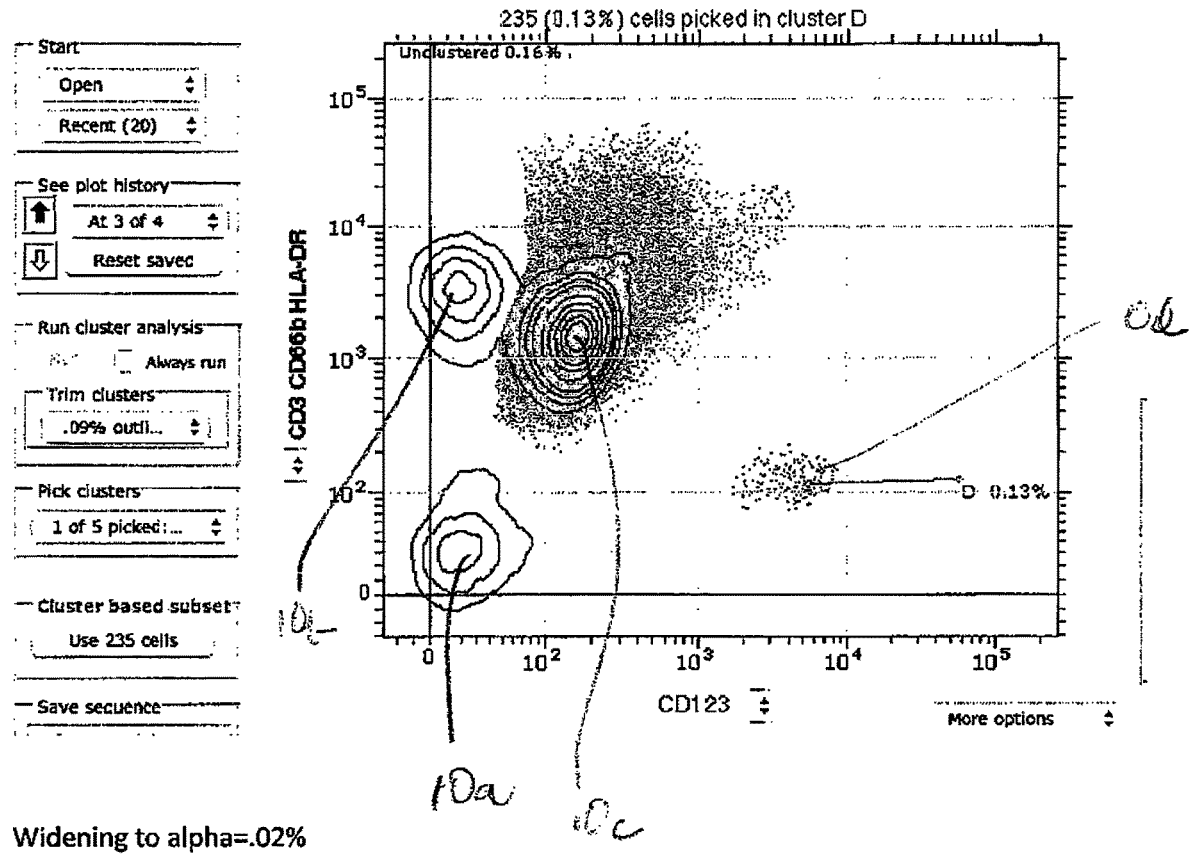
Figure 11:
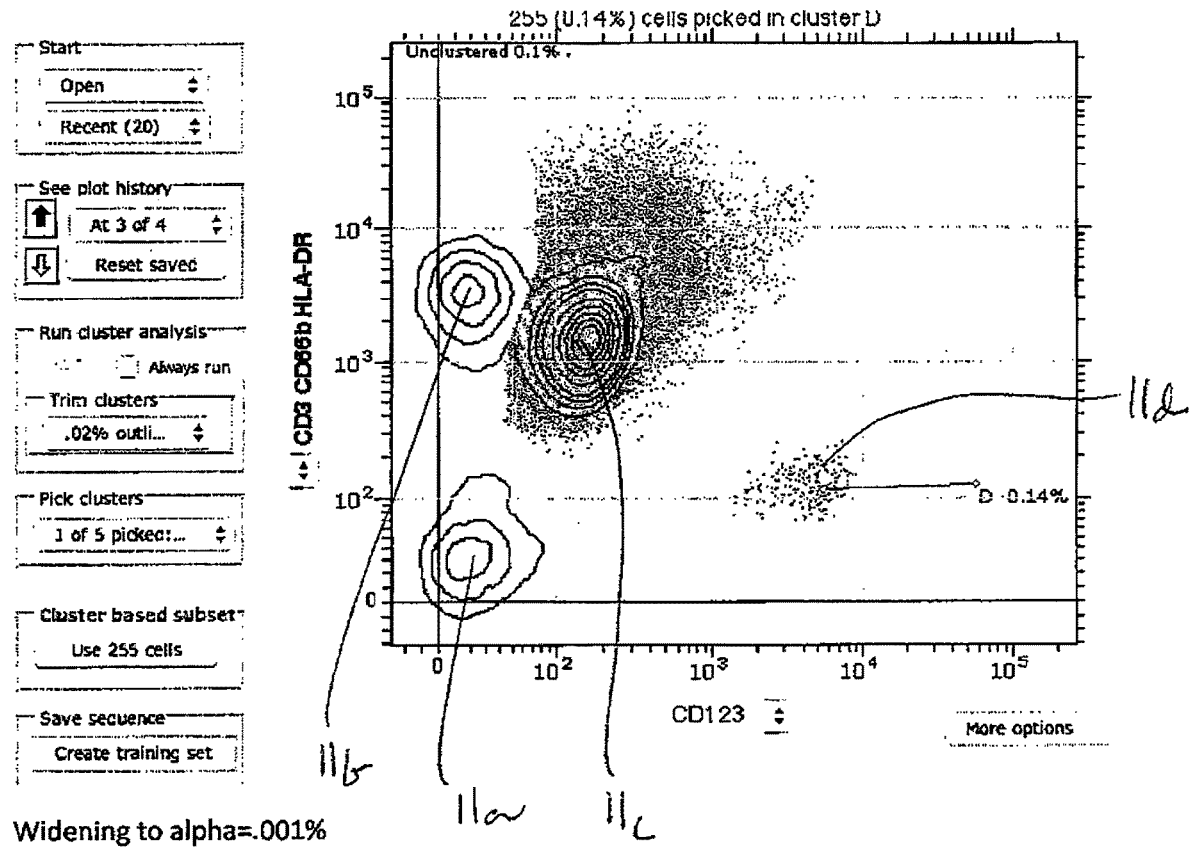
Figure 12:
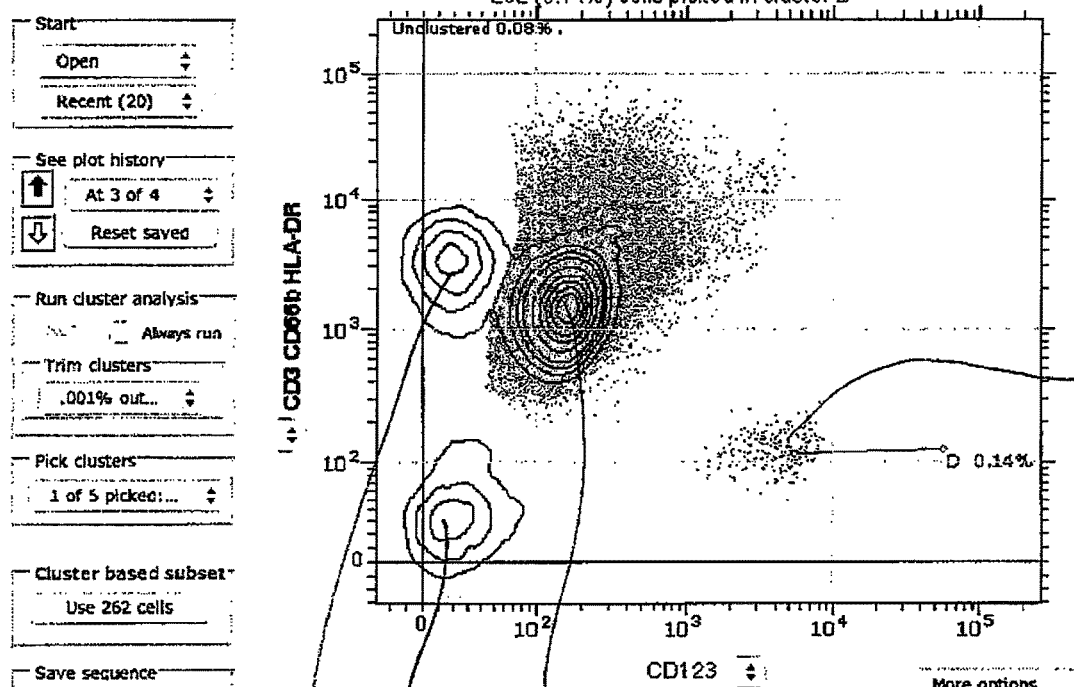

FIG. 9 shows a 2D plot of CD 123, a granulocyte marker vs. an exclusionary (dump) channel used to remove unwanted cells expressing the CD3, CD66b, and HLA-DR markers. The plot shows four clusters 9a, 9b, 9c and 9d that have been discerned by the DBM method described above. The clusters may be attributable to the existence of at least four types of cells present in the population. In this case, the population of interest (lower right in the figure) contains rare cells (granulocytes) that represent less than ~1% of the total number of cells in the analysis. This rare population is excluded by the usual outlier trimming process. However, decreasing percentage of cells trimmed clearly reveals the population (see FIG. 9)

Cluster Matching Between Different Samples

An aspect of the present disclosure that shall be described more fully below is to record a sequence of clustering steps that result in a meaningful clustering of the data taken from individuals in a population and then to apply that same sequence of clustering to another sample population from which like individuals can be discerned. In accordance with one aspect of the present disclosure, the efficacy of a given clustering sequence in isolating individuals of a common type or having common measurable attributes, e.g., cells of the same type, is tested by measuring the degree of matching of the clusters produced by a first clustering operation with the clusters that are indicated as the same in some respect in a second clustering operation. This measurement of degree of matching can be useful in confirming the existence of expected subsets of the population, observing when an expected subset is missing, identifying new/unexpected subsets and observing subsets that are subdividable into distinguishable clusters.

Figures 13, 14:
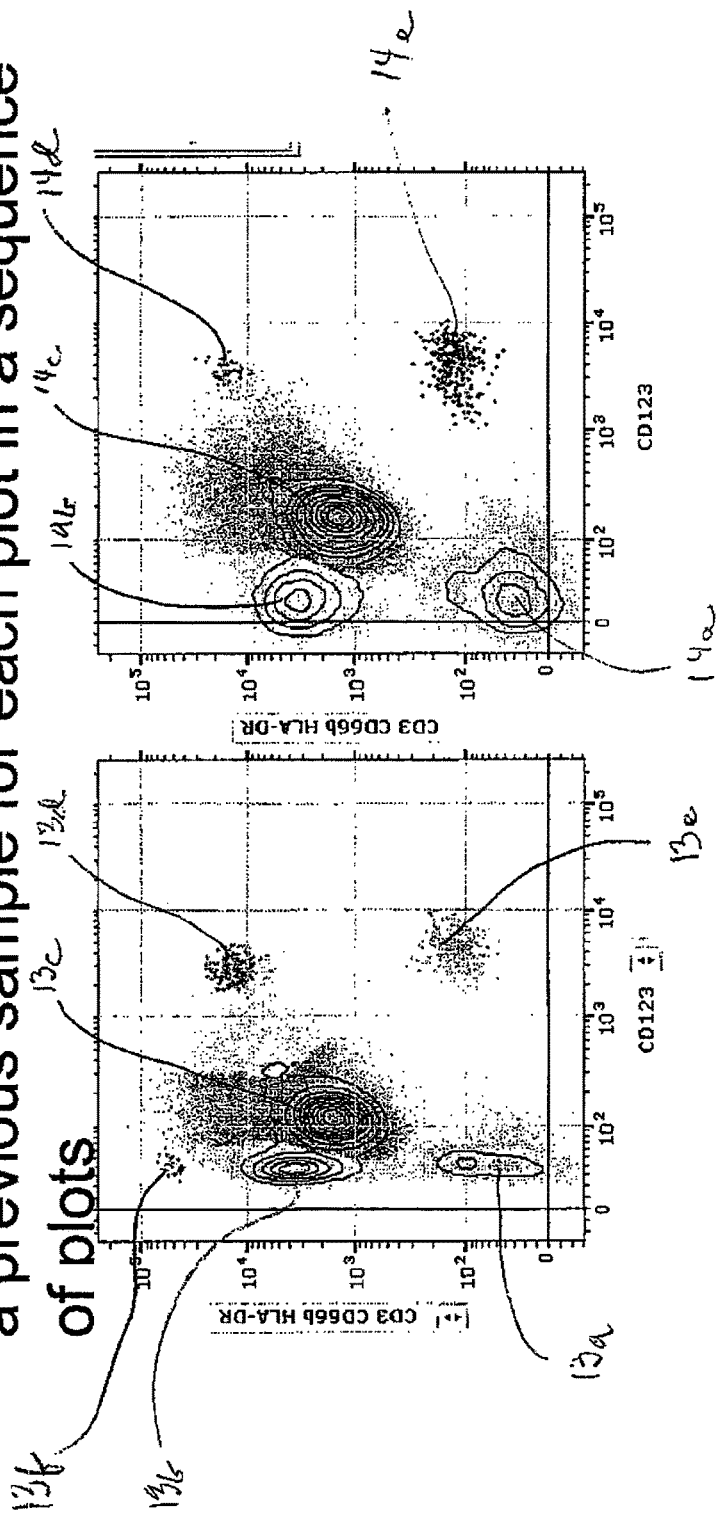
FIGS. 13, 14 are screen shots showing a comparison of clusters of the same type from different samples.

FIGS. 13, 14 are screen shots showing a comparison of clusters of the same type from different samples. The clusters 13a, 13b, 13c, 13d, 13e appear to be similar to 14a, 14b, 14c, 14d, 14e, respectively. 13f does not appear to have an analogous cluster in FIG. 14. In addition, there are differences in shape and size of the clusters shown in FIGS. 13 and 14. In accordance with an aspect of the present disclosure, the similarity or dissimilarity of two clusters may be objectively measured and quantified. In conducting this comparison, there are four different approaches that may be utilized, viz., i) calculating the median for each cluster to be compared and comparing the respective medians; ii) comparing peaks of each cluster to be compared; iii) using an Earth Mover Distance calculation to convert one cluster to the other cluster to which it is compared; and iv) weighted overlap.

With respect to use of the Earth Mover Distance approach, matching implies matching both distance and mass, with mass potentially causing an inappropriate assignment In contrast, a comparison of peak values is not affected by cluster mass.

FIG. 15 diagrammatically depicts a cluster grid 15a (red) having a plurality of grid points 15p derived from a cell sample of unknown composition, which could be described as a student population. FIG. 16 diagrammatically depicts a cluster grid 16b (blue) having a plurality of grid points 16p derived from DBM clustering of a training population, e.g., a cell sample of known composition, showing density values at a plurality of grid points, i.e., those density values which exceed zero. The values ascribed to the grid points are derived from the data discerned from testing the cells of both populations using a form of measurement of two parameters of the cells, e.g., the reflectance or absorption of laser light projected at each individual cell as it passes through a flow cytometer, a subset of which measurements define the grid space or layout in two dimensions. In accordance with an aspect of the present disclosure, the clusters 15a, 16a may be automatically and quantitatively compared by observing where the respective grid points 15, 16p with non-zero values overlap or intersect. FIG. 17 shows a concatenation grid 17a of the cluster grids 15a, 16a of FIGS. 15 and 16. The concatenation grid 17a has a plurality of grid points 17p with the associated values of the grid points 15p, 16p shown and the origin of each value indicated by color. Where there is no overlap, the grid points retain their original color. Where there is an overlap, a new color is assigned to the grid points 17p. The weight for the teacher grid points 16p that intersect are summed and the weight of the student grid points 15p that intersect are summed. The higher weight of the sum of the teacher grid point 16p or the sum of the student grid points 15p, may be used as the measure of overlap. In the example shown the teacher overlap is 24.6 and the student overlap is 12, so the measured overlap may be taken as 26.4.

The foregoing method of observing the degree of overlap between any given cluster may be utilized to identify maximum cluster to cluster correspondence, viz., by comparing every student cluster to every trainer cluster and assigning a cluster-to-cluster correspondence that yields the largest overlap, thereby identifying optimal cluster matching.

FIGS. 18 and 19 show screen shots 18s, 19s showing a comparison of clusters between two successive sample populations of cells from similar but distinct sources. FACS analysis reveals similar clusters in each. This determination can be automatically conducted using the measurement of overlap method described above. The method identifies matched clusters where they occur and reports new or missing clusters.

FIGS. 20 and 21 show screen shots 20s, 21s illustrating a comparison of clusters 20a, 20b, 20c and 20d with 21a, 21b, 21c, representing two successive samples of populations of cells and the detection of new cluster 20d in FIG. 20, which was not present in FIG. 21. In the event that a comparison of clusters present in compared 2D grids indicates that there is no overlap or an insufficient overlap relative to a given threshold, between a first cluster 20d present in a first cluster grid, e.g., that of a student population and the clusters present on a second cluster grid, e.g., that of a training population, then the system in accordance with an aspect of the present disclosure may automatically conclude that the non-matching cluster is a unique or "new" cluster relative to the comparative population. In the instance of cell samples, a "new" cluster may be attributable to a new type of cell subgroup that is present in the student population that is not present in the teacher sample.

FIGS. 22 and 23 are screen shots 22s, 23s showing a comparison of clusters 22a . . . 22f with clusters 23a . . . 23e, i.e., between two successive samples of populations of cells and the detection of the splitting of cluster 23e into two differentiable clusters 22e, 22f one of which was not present in FIG. 23. In the event that a comparison of clusters present in compared 2D grids indicates that for a given cluster in the first population there is more than one corresponding cluster in a second population and that the more than one cluster is divided into differentiable clusters one from another (having a significantly different measure of overlap relative to, then in accordance with an aspect of the present disclosure, the system of the present disclosure may automatically recognize and classify the plural clusters as clusters split from the larger, more cohesive cluster to which it is compared. As an example of an instance when splitting may occur, FIGS. 24 and 25 are screen shots 24s, 25s showing a comparison of clusters 24a, 24b, 24c with clusters 25a . . . 25d between data for two successive samples of populations of cells and the detection of a missing cluster 25c in FIG. 24 that was previously present in FIG. 25.

In the event that a comparison of clusters present in compared 2D grids indicates that there is no overlap or an insufficient measure of overlap between a first cluster present in a first cluster grid, e.g., that of a teaching population and the clusters present on a second cluster grid, e.g., that of a student population, then the system in accordance with an aspect of the present disclosure may automatically conclude that the non-matching cluster previously present is missing or absent relative to the cluster that was previously present in the teaching population. In the instance of cell samples, a "missing" cluster may be attributable to a type of cell subgroup that is present in the teaching population that is not present in the student sample. In the example shown, the training set had 136,179 cells of which 29,999 (22% were clustered in cluster 25c, corresponding to lymphocyte cells. The test sample of cells in FIG. 24 had 138,057 cells from a RAG knockout mouse from which a cluster attributable to lymphocytes was absent. The system may utilize a message displayed to the operator to note the absence of a cluster previously present.

Recording Probative Clustering Sequences

FIG. 26 shows a series of screen shots 26s of clusters 26a . . . 26d identified by a sequence of pairs of 2D parameters 26p and clustered using DBM, leading to the identification of a cluster 26d corresponding to a specific subset of a population. For many population samples, such as the constituents of a blood sample, there may be many subgroups, e.g., erythrocytes, leucocytes, platelets, etc., each of which has measurable properties. Some of the measurable properties of the subgroups are shared or in common with other subgroups and some properties or groups of properties may be used to distinguish one subgroup from another. In some instances, populations such as cells of a blood sample may be classified and characterized by a tree structure where differentiable branches extend from roots of commonality based upon origin, function and measurable properties. For example, items found in the human blood stream may include cells, indigenous components and foreign bodies/compounds. The cells can be subdivided into living cells and dead cells and the living cells can be further subdivided into erythrocytes, leucocytes, including neutrophils, eosinophils, basophils, lymphocytes (B cells and T cells) monocytes, macrophages, dendritic cells and platelets. The cells are suspended in plasma, which is predominantly water, but also contains proteins, glucose, hormones and gases like $CO_2$. Many of the cells in blood can be further subdivided into various states of development and states of being depending upon their experience, e.g., due to exposure to an environmental factor, such as an allergen, a toxin, or a given concentration of a normal environmental element or compound, such as Oxygen. A sensing/measuring apparatus, such as a flow cytometer, may be able to measure properties, e.g. responses to exposure to laser light, which may comprise a signature of a particular type of blood component, e.g., a given type of cell and/or a particular state, when considered as a group. Given the large number of possible types of components in a given sample, the large number of components, the large number of possible states that may be of interest and the large number of measurable parameters (which provide information that is not directly indicative, but merely provides the basis for inference or hypothesis) it is not necessarily obvious at the outset which properties are indicative of a certain group or subset, e.g., of cells or constituents in a blood sample.

One approach to identifying subgroups in a sample is to sequentially execute a series of clustering processes in accordance with the present disclosure in a manner guided by knowledge and insight/hypothesis, with the system of the present disclosure, recording each 2D clustering result in the sequence 26sq of "views" 26s on the data of the sample. In the instance where a given sequence of views 26sq of clusters, e.g., 26a, 26b, 26c, 26d, results in the identification of the subgroup of interest 26d (isolating it from a large population having other subgroups), then that particular recorded sequence 26sq of clustering steps may be identified as being probative/effective for identifying that particular subgroup. The effective sequence 26sq of clustering may then be applied to another sample set, e.g., another human blood sample for the purpose of identifying the same subgroup 26d in that different sample, which may then be counted or physically isolated for further testing/analysis.

Guiding Clustering Strategy

Figure 27:
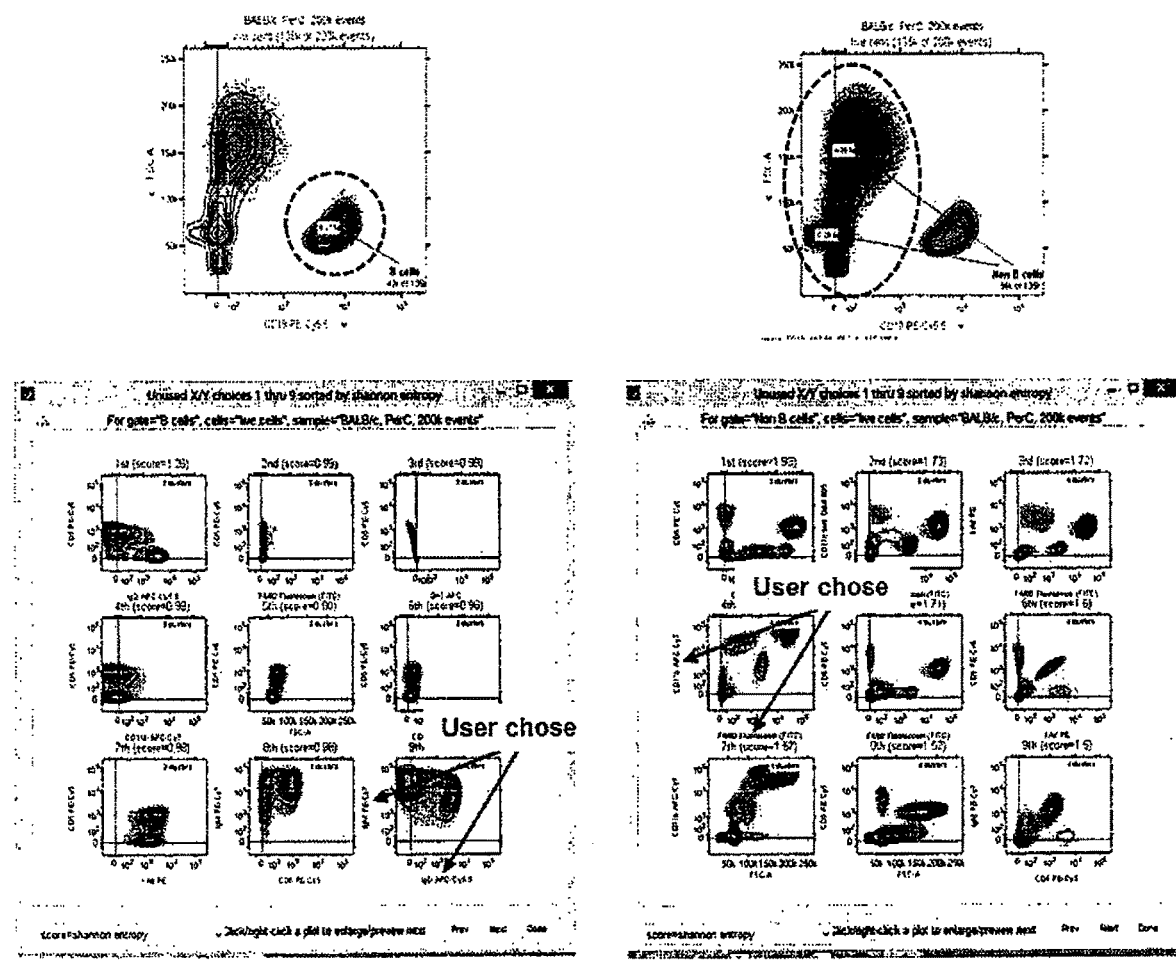
FIG. 27 shows screen shots for clustered data for dimension pairs advised as a next step (axis choice) in clustering process based on "dimensions-ranking score".

FIG. 27 shows screen shots for dimension pairs advised as a next step in the clustering process based on "dimensions-ranking score". This is an objective way to choose a clustering strategy based on highest/lowest scoring metric. It is a useful tool to explore new clustering strategies in comparison with well beaten paths. This embodiment uniquely combines objective and reliable statistical approaches together with an option to take the prior information into account and control clustering process step by step.

Marketing Example

While the invention has been explained largely in reference to its application to the study of cells in the context of the measurement of cell properties using cytometry, the clustering analysis and other techniques described herein can readily be applied to other populations with other measurable properties. For example, in the area of marketing one could study populations of people to ascertain which persons would be likely consumers of a given product. For example, with respect to the marketing of diapers, consumers who are identified as likely buyers may be sent coupons or emails providing incentives to purchase diapers. Since unsolicited, inappropriate offers and communications are both wasteful and annoying to consumers, it is generally preferred to send such communications only to persons with a reasonably high likelihood of purchasing the product promoted. With the advancement of data collection from use of the Internet, through records collected of purchases made in stores and from publically available information, such as voting and property ownership records, substantial quantities of data are available to merchants by which targeted advertising may be guided. In accordance with the present disclosure, such data may be processed similarly to the measured property data garnered about cells by a cytometry device.

With respect to the purchase of diapers, a merchant entity may have data concerning an individual's: age, sex, citizenship, driver status, voting registration, surname, given name, physical attributes, such as height, weight, eye color, hair color, marital status, interests, shopping habits, geographic location and all associated information relative to the geographic area such as the presence and location of drug stores, outlets, discount stores, the demography of the area including national origin, religious affiliations, economic status, crime statistics, home ownership rate, value of homes, etc.

An effort may be made to obtain information concerning persons who have previously purchased the merchant's product (diapers) in the past and that data may be entered into a system like system 700 described above and the data subjected to a DBM clustering analysis. The data clusters may be displayed in 2D displays in a similar manner to the display of clusters of cells as described and illustrated herein, such that trends may be displayed graphically and the attributes of groups of diaper purchasers may be observed and recorded. This population may function as the training population. A sequence of 2D clustering measures may be observed which is probative of whether a given individual may be likely to purchase diapers. For example, a measurement of age and sex of diaper purchasers may reveal clusters of women 18-30 representing young mothers and women 45-55 representing care giving grandmothers that have a higher propensity to purchase diapers than females of other ages and of males. In considering a given market, knowledge or hunches may provide a predictive hypothesis, e.g., that areas with high income and marriage rates will have fewer grandmothers with principle day-to-day infant caregiving roles. Based on this hypothesis, a clustering analysis using the dimensions income and marriage rates may be conducted on the subgroup of women aged 45-55 who purchase diapers. In the event that a large portion of this subgroup forms a cluster of low income persons in a low marriage rate geographic area, this would seem to confirm the hypothesis that women aged 45-55 in low income areas with low marriage rates have a higher likelihood of purchasing diapers than similarly aged women with higher income and higher marriage rates. Taking this example further, the foregoing 2D clustering approach may reveal a small cluster of women aged 45-55 who have medium income in high marriage rate areas who purchase many diapers. This group may have no obvious logical foundation until that group is further decomposed by presence of religious affiliation/membership in charitable organizations and a geographic location proximate to a institution for the charitable support of mothers needing charitable support, revealing a cluster of middle-aged, middle income women with religious affiliations/charitable intentions that encourage the purchase of diapers for the support of young mothers needing charitable support. As can be appreciated by the foregoing, a population may be sequentially analyzed/decomposed/partitioned via sequential invocations of clustering applied in two measurement dimensions. As noted, the sequence of clustering analysis can be recorded and applied to another population's data (a student population) and may progressively focus/filter subgroups based upon differentiating data, effectively traversing a tree structure of subgroups. In the foregoing example, the trends and predictive measures may be operational over a range, e.g., within a given country or culture having common cultural values and expectations, but inoperable in another cultural setting or country, since the behavior of persons is strongly effected by culture, such that a new sequence of clustering may be required to predict diaper purchasing propensity in another setting.

Manual Gating

Besides imposing guidance on the sequence of clustering analysis based upon expert knowledge, hunches, rules of thumb or logically-based hypotheses that impact the selection of the next set of dimensions to further decompose the population, the automated analysis by sequential DBM clustering can also be guided by manually "gating" displayed clusters. Manual gating or the proposed identification of clusters or patterns of groups of individuals in a population by marking a boundary around the display of data points associated with those individuals displayed on a 2D grid (e.g., using a drawing tool or a stylus applied to a touch or capacitance sensitive screen) is known.

An attribute of the present disclosure is the optional guidance of a clustering sequence by including at least one manual imposition of gating on the displayed clusters e.g., via a human operator drawing on a touch sensitive screen displaying clusters. In this manner, human insight/intuition may be incorporated with an automated gating process, e.g., using DBM. The individuals of the population, which may be designated the "manually gated cluster" may then be decomposed and analyzed by subsequent applications of automated density based merging clustering using additional 2D dimensions. This process of manual gating can be interspersed in a series or sequence of recorded clustering steps that can include any given number of DBM and manual gating in any given combination and order.

Repeated DBM

In yet another alternative, the clustering sequence may include a re-imposition of a clustering step on a data set (subpopulation) already parsed by a prior clustering using the same 2d measurements by DBM. In this manner, clusters may be refined. In response to a first clustering step, a first cluster is identified. Upon reclustering using the identified cluster and the same parameters, the cluster is narrowed to a smaller subset of members to improve resolution. Improvements in resolution can lead to the detection of additional clusters, which may be confirmed to be new by an earth mover distance calculation and/or by measuring the overlap as described above in reference to FIGS. 15-17.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the described invention has been described with reference to the some embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed:
1. A computer implemented method for identifying clusters of data items in a set of multi-dimensional data items corresponding to flow cytometry data of individuals, the computer implemented method comprising:

obtaining or accessing the set of data items corresponding to flow cytometry data of individuals with each data item corresponding to an observation of an individual and each observation having d dimensions where each dimension represents a value relative to the observation;

defining a plurality of lattice points in a data space able to contain at least some of the set of data items, the lattice points spaced according to a lattice rule and used as data reduction points in the data space;

calculating weights for the lattice points, each calculation of a weight for a lattice point using one or more of the data items according to a weighting rule;

determining an estimated density surface relating a weight at a lattice point to weights at nearby lattice points using a density function;

creating, for each lattice point in at least a subset of the lattice points, a directional association with at least one other lattice point using an association rule based, at least in part, the estimated density surface at the lattice point;

following directional associations between lattice points and determining a terminal state for each of one or more pointer paths formed by the directional associations between lattice points by identifying a last lattice point in the pointer path that does not have a pointer to another lattice point originating from it as a cluster root or as background noise based on a comparison between a density estimate for the last lattice point and a density estimate threshold;

assigning each lattice point in the pointer path to a cluster corresponding to the cluster root or to background noise based on the determined terminal state of the pointer path;

assigning each data item contained in the data space to a lattice point according to an assignment rule; and assigning each data item contained in the data space to a cluster or to background noise based on the assignment of the corresponding lattice point.

2. The method of claim 1, wherein the individuals are individual cells, and wherein the data items are groups of values, each associated with an individual cell and the cluster is a cell subpopulation.

3. The method of claim 1, wherein for at least two of the dimensions of an observation, the value for the dimension represents an effectively continuous data value, where an effectively continuous data value is a data value corresponding to a variable that is not discrete and can take any value between its minimum value and its maximum value down to a limit of resolution.

4. The method of claim 1, wherein the assignment of lattice points to one or more clusters or to background is based on directional associations of a plurality of lattice points and a density estimated at each lattice point and not weights assigned to lattice points or values of the data items.

5. The method of claim 1, wherein d is greater than two, wherein the data items are clustered based on a subset of the d dimensions, and wherein the method further comprises performing additional clustering on one or more individual clusters to subdivide the individual cluster based on values measured in a different subset of the d dimensions than the subset used to define the individual cluster.

6. The method according to claim 5, wherein the method is used recursively to perform sequential clustering on identified clusters, and wherein the method further comprises generating a graphical display of the result of the sequential clustering as a tree structure comprising one or more successive child nodes in the tree corresponding to clusters obtained by clustering the parent preceding node.

7. The method according to claim 5, wherein the method is used recursively to perform sequential clustering on identified clusters;

saving information regarding which subset of the d dimensions was used to perform clustering at each stage in the sequence as a sequence of clustering; and applying the saved sequence of clustering to identify clusters of data items in a second set of multi-dimensional data items corresponding to flow cytometry data of a second set of individuals.

8. The method of claim 1, further comprising, providing a graphical user interface for receiving information regarding a density estimate threshold to employ for distinguishing between a cluster root and background noise.

9. The method of claim 8, further comprising, adjusting cluster boundaries by trimming to include or eliminate data items from the cluster based on user input, the adjusting including modifying the density estimate threshold employed for distinguishing between a cluster root and background noise based on information received via the graphical user interface.

10. A method of using an information system to cluster data items in a set of multi-dimensional data items corresponding to flow cytometry data of individuals, wherein a data item is associated with one or more semi-continuous values, the method comprising:

obtaining or accessing the set of data items corresponding to flow cytometry data of individuals with each data item corresponding to an observation of an individual and each observation having d dimensions, where each dimension represents a semi-continuous value relative to the observation, a semi-continuous value being a value of a variable that can take the value zero or any value above a positive threshold;

creating a reduction data item set, each reduction data item in the reduction data item set associated with one or more quantized values correlated with the one or more semi-continuous values for one or more data items;

assigning each data item to a reduction data item according to an assignment rule;

calculating weights for the reduction data items using one or more data items assigned to the reduction data item according to a weighting rule;

determining an estimated density surface based on the weights assigned to each reduction data item;

determining for each of a plurality of reduction data items if the reduction data item should be associated with another reduction data item according to an association rule based on the estimated density surface, and if so, creating a directional association of the reduction data item with the other reduction data item; and following directional associations between reduction data items and determining a terminal state for each of one or more pointer paths formed by the directional associations between reduction data items by identifying a last reduction data item in the pointer path that does not have a pointer to another reduction data item originating from it as a cluster root or as background noise based on a comparison between a density estimate for the last reduction data item and a density estimate threshold;

identifying one or more clusters of the reduction data items using one or more directional associations and/or one or more of the weights, thereby identifying clusters of the data items based on the identification of the associated reduction data items.

11. The method of claim 10, wherein the step of calculating weights includes linear binning in accordance with the formula:

$$w_m = \sum_{i=1}^{n} \prod_{j=1}^{d} \max(0, 1 - |x_{i,j} - y_{mj}|/\Delta_j)$$

where the data items include a set of n observations $x_1, \ldots x_n$ for each dimension, where j is a dimension of the lattice and of the observations, where $y_{mj}$ is a lattice point, and where $\Delta_j$ is a lattice spacing in the j dimension.

12. The method of claim 11, wherein determining an estimated density surface includes computing an estimate of a density surface $\hat{f}(y_m)$ wherein the Gaussian kernel is denoted by $\phi(b) = 1/\sqrt{2\pi} \exp(-b^2/2)$ and the estimated density $y_m$ is computed by the formula:

$$\hat{f}(y_m) = 1/n \sum_{l_1=-Z_1}^{Z_1} \cdots \sum_{l_d=-Z_d}^{Z_d} \omega_{m-1} \prod_{j=1}^{d} \phi(l_j \Delta_j / h_j)/h_j,$$

where $l=(l_1, \ldots, l_d)$, $Z_j = \min(\lfloor 4h_j/\Delta_j \rfloor, M-1)$, and $h_j = SD(\{x_{i,j}, i=1, \ldots, n\}) n^{-1/(d+4)}$, where SD denotes standard deviation, n denotes number of observations, l denotes iterative position of the grid that navigates from z to −z, and $l_{1-d}$ denotes a relative offset of the grid position referred to by the term m for each 1–d dimensions of the grid, and d denotes the total number of dimensions.

13. The method of claim 12, wherein the formula:

$$\hat{f}(y_m) = 1/n \sum_{l_1=-Z_1}^{Z_1} \cdots \sum_{l_d=-Z_d}^{Z_d} \omega_{m-1} \prod_{j=1}^{d} \phi(l_j \Delta_j / h_j)/h_j,$$

where $l=(l_1, \ldots, l_d)$, $Z_j = \min(\lfloor 4h_j/\Delta_j \rfloor, M-1)$, and $h_j = SD(\{x_{i,j}, i=1, \ldots, n\}) n^{-1/(d+4)}$ is computed by the Fast Fourier Transform (FFT).

14. The method of claim 11, wherein determining an estimated density surface includes calculating an estimate of the standard deviation of the density estimate in accordance with the formula:

$$\hat{\sigma}_m^2 = \frac{1}{n(n-1)} \sum_{l_1=-Z_1}^{Z_1} \cdots \sum_{l_d=-Z_d}^{Z_d} w_{m-1} \prod_{j=1}^{d} \phi^2(l_j \Delta_j / h_j)/h_j^2 - \frac{1}{n-1} \hat{f}(y_m)^2$$

and defining an index set $S = \{m \in \{1, \ldots M\}^d : \hat{f}(y_m) > 4.3 * \sqrt{\hat{\sigma}_m^2}\}$ wherein n denotes number of observations, and l denotes iterative position of the grid that navigates from z to −z.

15. The method of claim 14, wherein the step of creating a directional association includes establishing and removing pointers between neighboring lattice points by successively executing a series of evaluations for all lattice points $y_m$, where m is an element of S, in turn:

considering all neighboring lattice points $p_1, \ldots, p_{nm}$ which are defined as the set of all lattice points contained in a s-dimensional rectangular volume, letting p be an element of $\{p_1, \ldots, p_{nm}\}$ such that $\hat{f}(p) = \max_{k=1,\ldots,nm} \hat{f}(p_k)$, splitting ties in an arbitrary manner; then a pointer is established from $y_m$ to p provided:

$$\hat{f}(p) > \hat{f}(y_m); \text{ and}$$

$$\frac{\partial}{\partial e} \hat{f}(y_m) > \lambda_m,$$

where $e = (p - y_m)/\|p - y_m\|$, $\|\cdot\|$ denotes Euclidean norm, and $$\frac{\partial}{\partial e} \hat{f}(y_m) = \sum_{a=1}^{d} e_a \frac{\partial}{\partial y_{m_a}} \hat{f}(y_m),$$

which indicates a gradient of the density estimate, $$\frac{\partial}{\partial y_{m_a}} \hat{f}(y_m) =$$

$$1/n \sum_{l_1=-Z_1}^{Z_1} \cdots \sum_{l_d=-Z_d}^{Z_d} w_{m-1} \frac{-l_a \Delta_a}{h_a^2} \prod_{j=1}^{d} \phi(l_j \Delta_j / h_j)/h_j$$

$$\lambda_m = q(0.95^{1/\kappa}) \sqrt{\hat{\Sigma}_m^2}$$

$$\kappa = \frac{\# S \Sigma_{m \in S} w_m}{n(2\pi)^{d/2} \prod_{j=1}^{d} h_j \Sigma_{m \in S} w_m \hat{f}(y_m)}$$

$$\hat{\Sigma}_m^2 = \frac{1}{n-1} \left( \sum_{a,b=1}^{d} e_a e_b \left[ A - \frac{\partial}{\partial y_{m_a}} \hat{f}(y_m) \frac{\partial}{\partial y_{m_b}} \hat{f}(y_m) \right] \right)$$

$$A = \frac{1}{n} \sum_{l_1=-Z_1}^{Z_1} \cdots \sum_{l_d=-Z_d}^{Z_d} w_{m-1} \frac{l_a l_b \Delta_a \Delta_b}{h_a^2 h_b^2} \prod_{\varphi=1}^{\delta} \phi^2(l_j \Delta_j / h_j)/h_j^2$$

A being an estimate of $$\frac{\partial}{\partial y_{m_a}} f(y_m) \frac{\partial}{\partial y_{m_b}} f(y_m)$$

and q(x) denotes the 100*xth percentile of the standard normal distribution.

16. The method of claim 15, wherein from each lattice point $y_m$, where m is not an element of S, a pointer is established that points to a state representing background noise.

17. The method of claim 16, wherein the step of following directional associations further includes the evaluation: for all lattice points $y_m$, where m is an element of S, in turn: if a pointer originates at $y_m$, then it will point to a different lattice point, which itself may have a pointer originating from it; following a succession of pointers until a lattice point $y_z$ is reached that either (a) does not have any pointer originating from it or (b) has a pointer originating from it that points to a state representing a cluster or background noise; in the event (a) removing all pointers visited in the succession and establishing new pointers originating from each lattice point to the background noise state, provided $\hat{f}(y_z)>q(0.95^{1/\kappa})\sqrt{\hat{\sigma}_z^2}$, otherwise only the pointer originating from $y_z$ is removed and a new pointer is established that originates from $y_z$ (if any) is removed and a new pointer is establishes that originates from $y_z$ and points to a new cluster state, in the event (b) no pointers are removed or established.

18. The method of claim 17, wherein the step of following directional associations further includes the following steps:
Let $\{y_{m(1)}, \ldots y_{m(k)}\}$ be the set of all lattice points which have a pointer originating from them to a dummy state representing a cluster, enumerated such that $\hat{f}(y_{m(1)}) \leq \ldots \leq \hat{f}(y_{m(k)})$ and for $i=1, \ldots, k$ do:
Set A={m(i), and iterate the following loop until no more indices are added to A:
(Begin loop)
For each index a which is an element of A in turn, add all the indices p to A that satisfy:
$y_p$ is a neighbor of $y_a$ as defined in claim 15, and
No pointer originates from $y_p$, and $$\hat{f}(y_p)+\hat{\sigma}_p \geq \hat{f}(y_{m(i)})+\hat{\sigma}_{m(i)}$$

(End loop)
Denote by B the set of indices of lattice points from which a pointer originates to a cluster state and that also have some $y_p$, p being an element of as neighbor, If B is not empty, then do the following:
Define q by $\hat{f}(y_q)=\max_{r \in B}\hat{f}(y_r)$, breaking ties arbitrarily;
Establish a pointer from each $y_p$, p being an element of A\{m(i)} to $y_q$;
For each r which is an element of B, if r≠q, remove the pointer from $y_r$ to the state representing a cluster and establish a new pointer from $y_r$ to $y_q$.

19. The method of claim 18, wherein the steps recited in claim 18 are repeated until there are no more additions or deletions of pointers to cluster state.

20. The method of claim 19, wherein from each lattice point that does not have a pointer originating from it, a pointer is established pointing to the background noise state.

21. An apparatus for creating groupings of data items in a set of multi-dimensional data items corresponding to flow cytometry data of individuals, the apparatus comprising:
storage configured to store the set of multi-dimensional data items corresponding to flow cytometry data of individuals with each data item corresponding to an observation of an individual and each observation having d dimensions where each dimension represents a value relative to the observation; and
one or more processors configured to execute instructions, that, when executed by the processor, cause the apparatus to:
define a plurality of lattice points in a data space able to contain at least some of the set of data items, the lattice points spaced according to a lattice rule and used as data reduction points in the data space;
assign each data item from the set of data items to a point on a lattice;
assign a weight to each lattice point based on one or more data items near the lattice point;
determine an estimated density surface based on the weights assigned to each lattice point;
determine, for each of the lattice points, if the lattice point should be associated with one of its surrounding lattice points based on the estimated density surface, and, if so, associate the lattice point with the one of its surrounding lattice points by creating a pointer from the individual lattice point to the surrounding lattice point;
follow directional associations between lattice points and determine a terminal state for each of one or more pointer paths formed by the directional associations between lattice points by identifying a last lattice point in the pointer path that does not have a pointer to another lattice point originating from it as a cluster root or as background noise based on a comparison between a density estimate for the last lattice point and a density estimate threshold;
assign each lattice point to a cluster or to background noise based on associations between the lattice points and a values of the estimated density surface at lattice points; and
assign each data item contained in the data space to a cluster or to background noise based on the assignment of the corresponding lattice point.

22. A computer implemented method for guiding clustering strategy in identifying clusters of data items in a set of multi-dimensional data items corresponding to flow cytometry data of individuals, the method comprising:
obtaining or accessing the set of data items corresponding to flow cytometry data of individuals with each data item corresponding to an observation of an individual and each observation having d dimensions where each dimension represents a value relative to the observation and where d is greater than two;
clustering the data items based on a first pair of the d dimensions, the clustering the data items based on the first pair of the d dimensions comprising:
defining a plurality of lattice points in a data space able to contain at least some of the set of data items;
calculating weights for the lattice points;
determining an estimated density surface relating a weight at a lattice point to weights at nearby lattice points using a density function;
creating, for each lattice point in at least a subset of the lattice points, a directional association with at least one other lattice point using an association rule based, at least in part, the estimated density surface at the lattice point;
following directional associations between lattice points and determining a terminal state for each of one or more pointer paths formed by the directional associations between lattice points by identifying a last lattice point in the pointer path that does not have a pointer to another lattice point originating from it as a cluster root or as background noise based on a comparison between a density estimate for the last lattice point and a density estimate threshold;
assigning each lattice point in the pointer path to a cluster corresponding to the cluster root or to background noise based on the determined terminal state of the pointer path;
clustering the data items based on a second pair of the d dimensions, the second pair not identical to the first pair;
for each clustering of the data items based on a dimension pair, calculating an associated dimension pair entropy-based ranking score;
displaying to a user results of an automated dimension pair entropy-based ranking based on the calculated dimension pair entropy-based ranking score for each dimension pair used for clustering; and receiving a selection of a dimension pair from the user and implementing the user's selection of the dimension pair to be employed for clustering.

23. The method of claim 22, wherein calculating an associated dimension pair entropy-based ranking score comprises determining a standard negative differential entropy for the dimension pair.

24. The method of claim 22, wherein calculating an associated dimension pair entropy-based ranking score comprises determining a Shannon entropy score for the dimension pair.

* * * * *